US006339062B1

(12) United States Patent
Williams et al.

(10) Patent No.: US 6,339,062 B1
(45) Date of Patent: Jan. 15, 2002

(54) RETROINVERSO POLYPEPTIDES THAT MIMIC OR INHIBIT THROMBOSPONDIN ACTIVITY

(75) Inventors: Taffy Williams, Lansdale, PA (US); George Tuszynski, Pittsgrove, NJ (US); Paul Actor, Phoenixville, PA (US)

(73) Assignee: Inkine Pharmaceutical Company, Inc., Blue Bell, PA (US)

( * ) Notice: Subject to any disclaimer, the term of this patent is extended or adjusted under 35 U.S.C. 154(b) by 0 days.

(21) Appl. No.: 09/197,770

(22) Filed: Nov. 23, 1998

(51) Int. Cl.$^7$ .............................................. A61K 38/00
(52) U.S. Cl. ............................ 514/15; 514/16; 514/17; 530/300; 530/328; 530/329; 530/330; 424/185.1
(58) Field of Search .............................. 514/15, 16, 17; 530/300, 328, 329, 330; 424/185.1

(56) References Cited

U.S. PATENT DOCUMENTS

| | | | |
|---|---|---|---|
| 3,842,067 A | 10/1974 | Sarantakis et al. | 260/112.5 |
| 3,862,925 A | 1/1975 | Sarantakis et al. | 260/112.5 |
| 3,972,859 A | 8/1976 | Fujino et al. | 260/112.5 |
| 4,105,602 A | 8/1978 | Colescott et al. | 260/8 |
| 4,244,946 A | 1/1981 | Rivier et al. | 424/177 |
| 4,305,872 A | 12/1981 | Johnston et al. | 260/112.5 |
| 4,683,291 A | 7/1987 | Zimmerman et al. | 530/324 |
| 5,190,918 A | 3/1993 | Deutch et al. | 514/15 |
| 5,192,744 A | 3/1993 | Bouck et al. | 514/8 |
| 5,426,100 A | 6/1995 | Deutch et al. | 514/15 |
| 5,721,210 A | * 2/1998 | Loblet et al. | 514/11 |
| 5,753,230 A | * 5/1998 | Brooks et al. | 424/158.1 |
| 5,766,591 A | * 6/1998 | Brooks et al. | 424/184.1 |
| 5,770,563 A | * 6/1998 | Roberts et al. | 514/8 |

FOREIGN PATENT DOCUMENTS

| | | |
|---|---|---|
| EP | 0263 608 | 4/1988 |
| WO | WO 90/01496 | 2/1990 |
| WO | WO 92/17499 | 10/1992 |

OTHER PUBLICATIONS

Arap et al, "Cancer Treatment by Targeted Drug Delivery to Tumor Vasculature in a Mouse Model," *Science*, 279:377–380 (1998).
Crombie, Identification of a CD36–related Thrombospondin 1–binding Domain in HIV–1 Envelope Glycoprotein gp120: Relationship to HIV–1–specific Inhibitory Factors in Human Saliva, *J. Exp. Med.*, 187:25–35 (1998).
Yamashita Plamsa Thrombospondin Levels In Patients with Colorectal Carcinoma, *Cancer*, 82:632–638 (1998).
Albo, Thrombospondin–1 and transforming growth factor–beta1 promote breast tumor cell invasion through up–regulation of the plasminogen/plasmin system, *Surgery*, 122:493–500 (1997).
Qian, Thrombospondin–1 Modulates Angiogenesis in Vitro by Up–Regulation of Matrix Metalloproteinase–9 in Endothelial Cells, *Exp. Cell Res.*, 235:403–412 (1997).

Roth, Histopathology and clinical assessment correlate with the cysteine–serine–valine–threonine–systein–glycine (CSVTCG) receptor of thrombospondin–1 in breat tumors, *Histology & Histopathology*, 12:1013–1018 (1997).
Wang, Thrombospondin–1 (TSP–1) Promotes the Invasive Properties of Human Breast Cancer, *J. Surgical Res.*, 63:39–43 (1996).
Wang, Inhibition of Breast Cancer Progression by an Antibody to a Thrombospondin–1 Receptor, *Surgery*, 120:449–454 (1996).
Connors, Prodrugs in Cancer Chemotherapy, *Stem Cells*, 13:501–511 (1995).
Arnoletti, Computer–Assisted Image Analysis of Tumor Sections for a New Thrombospondin Receptor, *The American Journal of Surgery*, 168:433–436 (1994).
Nathan, Plasma Thrombospondin Levels in Patients with Gynecologic Malignancies, *Cancer*, 73:2853–2858 (1994).
Nicosia, Matrix–Bound Thrombospondin Promotes Angiogenesis In Vitro, *J. Cell Biol.*, 124:183–193 (1994).
Tuszynski, Localization of Thrombospondin and Its Cysteine–Serine–Valine–Threonine–Systeine–Glycine–Specific Receptor in Human Breast Carcinoma, *Lab. Invest.*, 70:228–233 (1994).
Adams, The Thrombospondin Family, *Current biology*, 3:188–190 (1993).
Clezardin, Expression of Thrombospondin (TSP1) and Its Receptors (CD36 and CD51) in Normal, Hyperplastic, and Neoplastic Human Breast, *Cancer Res.*, 53:1421–1430 (1993).
Tuszynski, Identification and Characterization of a Tumor Cell Receptor for CSVTCG, a Thrombospondin Adhesive Domain, *J. Cell Biol.*, 120:513–521 (1993).
Asch, Thrombospondin Sequence Motif (CSVTCG) is Responsible for CD36 Binding, *Biochem. Biophys. Res. Commun.*, 182:1208–1217 (1992).
Sugihara, Thrombospondin Mediates Adherence of CD36+ Sickle Reticulocytes to Endothelial Cells, *Blood*, 80(10):2634–2642 (1992).
Nusrat, A Role for Urokinase in Mediating Phorbol Ester Induced Macrophage–like Maturation and Adhesion of U937 and Other Myeloid Cells, *Fibrinolysis*, 6:71–76 (1992).

(List continued on next page.)

*Primary Examiner*—Avis M. Davenport
(74) *Attorney, Agent, or Firm*—Finnegan, Henderson, Farabow, Garrett & Dunner, L.L.P.

(57) ABSTRACT

The present invention relates generally to polypeptides that mimic or inhibit the biological activity of thrombospondin, and particularly to polypeptides in retroinverso form. These polypeptides may be used for their biological and pharmaceutical applications such as: (a) inhibiting the invasive and metastatic activity of melanoma cells, (b) promoting and inhibiting cellular attachment to tissue culture flacks, (c) promoting wound healing, angiogenesis, and implant acceptance, (d) agents for anti-platelet aggregation, (e) agents for antimalarial activity, and (f) diagnostic reagents in different therapeutic applications, as well as other related areas.

14 Claims, 23 Drawing Sheets

OTHER PUBLICATIONS

Tusynski, Thrombospondin Levels in Patients with Malignancy, *Thromb. and Haemost.,* 67:607–611 (1992).

Tuszynski, Biological Activities of Peptides and Peptide Analogues Derived from Common Sequences Present in Thrombospondin, Properdin, and Malarial Proteins, *J. Cell Biol.,* 116:209–217 (1992).

Wong, Thrombospondin and Other Possible Related Matrix Proteins in Malignant and Benign Breast Disease, *Am. J. Pathol.,* 140:1473–1482 (1992).

Davis, The vaso–occlusive crisis of sickle cell disease, *BMJ,* 302:1551–52 (1991).

Fields, Virus Interactions with Cell Uptake Mechanisms, Fundamental Virology, $2^{nd}$ Ed., 269–270 (1991).

Prater, The Properdin–like Type I Repeats of Human Thrombospondin Contain a Cell Attachment Site, *J. Cell Biol.,* 112:1031–1040 (1991).

Mosher, Physiology of Thrombospondin, *Annu. Rev. Med.,* 41:85–97 (1990).

Rich, Cell–Adhesive Motif in Region II of Malarial Circumsporozoite Protein, *Science,* 249:1574–1577 (1990).

Tuszynski, Spectrophotometric Quantitation of Anchorage–Dependent Cell Number Using the Bicinchoninic Acid Protein Assay Reagent, *Anal. Bio.,* 84:189–91 (1990).

Kanemoto, Identification of an Amino Acid Sequence from the Laminin A Chain that Stimulates Metastasis and Collagenase IV Production, *Proc. Natl. Acad. Sci.,* 87:2279–83 (1990).

Depoli, Thrombospondin Interation with Plasminogen, Evidence for Binding to a Specific Region of the Kringle Structure of Plasminogen, *Blood,* 73:976–982 (1989).

Dunwiddie, Antistasin, a Leech–derived Inhibitor of Facor Xa, *J. Biol. Chem.,* 264:16694–99 (1989).

Holt, Antistasin, an Inhibitor of Coagulation and Metastasis, Binds to Sulfatide (Gal(3–$SO_4$) (Beta–1 Cer) and Has a Sequence Homology with Other Proteins that Bind Sulfated Glycoconjugates, *J. Biol. Chem.,* 264:12138–40 (1989).

Han, Cloning and Expression of cDNA Encoding Antistasin, a Leech–derived Protein Having Anti–coagulant and Anti–metastatic Properties, *Gene,* 75:47–57 (1989).

Hennessy, Complete Thrombospondin mRNA Sequence Includes Potential Regulatory Sites in the 3' Untranlated Region, *J. Cell. Biol.,* 108:729–36 (1989).

J. Varani, Characterization of Thrombospondin Synthesis, Secretion and Cell Surface Expression by Human Tumor Cells, *Clin. Expl. Metastasis,* 7:265–76 (1989).

Pratt, Thrombospondin in Malignant and Non–Malignant Breast Tissue, *Eur. J. Cancer Clin. Oncol.* 25:343–350 (1989).

Yabkowitz, Expression and Initial Characterization of a Recombinant Human Thrombospondin Heparin Binding Domain, *J. Biol. Chem.,* 264:10888–96 (1989).

Goundis, Properdin, the Terminal Complement Components, Thrombospondin and the Circumsporozoite protein of Malaria Parasites Contain Similar Sequence Motifs, *Nature,* 335:82–85 (1988).

Herbst, Differential Effects of Laminin, Intact Type IV Collagen, and Specific Domains of Type IV Collagen on Endothelial Cell Adhesion and Migration, *J. Cell. Biol.,* 106:1365–1373 (1988).

Majack, Cell Surface Thrombospondin is Functionally Essential for Vascular Smooth Muscle Cell Proliferation, *J. Biol. Chem.,* 106:415–422 (1988).

Riser, Thrombospondin Binding by Human Squamous Carcinoma and Melanoma Cells: Relationship to Biological Activity, *Exp. Cell Res.,* 174:319–329 (1988).

Robson, A Highly Conserved Amino–Acid Sequence in Thrombospondin, Properdin and in Proteins from Sporozoites and Blood Stages of a Human Malaria Parasite, *Nature,* 335:79–82 (1988).

Tuszynski Thrombospondin Promotes Platelet Aggregation, *Blood,* 72:109–115 (1988).

Varani, Thrombospondin–induced Adhesion of Human Keratinocytes, *J. Clin. Invest.,* 81:1537–44 (1988).

Tuszynski, Isolation and Characterization of Antistasin, *J. Biol. Chem.,* 262:9718–9723 (1987).

Iwamoto, YIGSR, A Synthetic Laminin Pentapeptide, Inhibits Experimental Metastasis Formation, *Science,* 238:1132–34 (1987).

Lawler, Structural Organization of the Thrmpospondin Molecule, *Seminars in Thrombosis & Hemostasis,* 13:245–254 (1987).

Sasaki, Sequence of the cDNA Encoding the Laminin B1 Chain Reveals a Multidomin Protein Containing Cysteine–Rich Repeats, *Proc. Natl. Acad. Sci,* 84:935–39 (1987).

Tuszynski, Thrombospondin, a Potentiator of Tumor Cell Metastasis, *Cancer Res.,* 47:4130–4133 (1987).

Tuszynski, Thrombospondin Promotes Cell–Substratum Adhesion, *Science,* 236:1570–1573 (1987).

Tuszynski, Role of Thrombospondin in Hemostasis and Cell Adhesion, *Seminars in Thrombosis & Hemostasis,* 13:361–68 (1987).

Aiken, Isolation and Identification of a 23,000–Dalton Heparin Binding Fragment from the Amino Terminus of Bovine Thrombospondin, *Ach. Bio. Biophsy.,* 250:257–262 (1986).

Dixit et al., Characterization of a cDNA Encoding the Heparin and Collagen Binding Domains of Human Thrombospondin, *Proc. Natl. Acad. Sci.,* 83:5449–53 (1986).

Humphries, A Synthetic Peptide from Fibronectin Inhibitors Experimental Metastasis of Murine Melanoma Cells, *Science,* 233:467–70 (1986).

Kobayashi, Partial Amino Acid Sequence of Human Thrombospondin as Determined by Analysis of cDNA Clones: Homology to Malarial Circumsporozoite Proteins, *Biochemistry,* 25:8418–25 (1986).

Lawler, The Structural and Functional Properties of Thrombospondin, *Blood,* 67:1197–1209 (1986).

Lawler, Thrombospondin in Essential Thrombocythemia, *Blood,* 67:555–558 (1986).

Lawler, The Structure of Human Thrombospondin, an Adhesive Glycoprotein with Multiple Calcium–Binding Sites and Homologies with Several Different Positions, *J. Cell Biol.,* 103:1635–48 (1986).

Majack, Control of Smooth Muscle Cell Growth by Components of the Extracellular Matrix: Autocrine Role for Thrombosponsin, *Proc. Natl. Acad. Sci.,* 83:9050–54 (1986).

Dixit, A Monoclonal Antibody Against Human Thrombospondin Inhibits Platelet Aggregation, *Proc. Natl. Acad. Sci.,* 82:3472–76 (1985).

Majack, Platelet–derived Growth Factor and Heparin–like Glycosaminoglycans Regulate Thrombospondin Synthesis and Deposition in the Matrix by Smooth Muscle Cells, *J. Cell Biol.,* 101:1059–1070 (1985).

Schiller, Synthesis of Side–chain to Side–chain Cyclized Peptide Analogs on Solid Supports, *Int. J. Peptide Protein Res.*, 25:171–177 (1985).

Switalska, Radioimmunoassay of Human Platelet Thrombospondin: Different Patterns of Thrombospondin and Beta–Thromboglobulin Antigen Secretion and Celarance from the Circulation, *J. Lab. Clin. Med.*, 106:690–700 (1985).

Tuszynski, The Interaction of Human Platelet Thrombospondin with Fibrinogen: Thrombospondin Purification and specificity of Interaction, *J. Biol. Chem.*, 260:12240–5 (1985).

Houghton, General Method for the Rapid Solid–Phase Synthesis of Large Numbers of Peptides: Specificity of Antigen–antibody Interaction at the Level of Individual Amino Acids, *Proc. Natl. Acad. Sci.*, 82:5131–5135 (1985).

Alexander, Quantitative Adsorption of Platelet Glycoprotein G. (Thrombin–Sensitive Protein, Thrombospondin) to Barium Citrate, *Biochem. J.*, 217–71 (1984).

Barsky, Laminin Molecular Domains which Alter Metastasis in a Murine Model, *J. Clin. Inv.*, 74:843–48 (1984).

Clezardin, Isolation of Thrombospondin Released from Thrombin–Stimulated Human Platelets by Fast Protein Liquid Chromatography on an Anion–Exchange Mono–Q Column, *J. Chromatog.* 296:249–56 (1984).

Gasic, Role of Plasma, Platelets, and Endothelial Cells in Tumor Metastasis, *Cancer Metastasis Rev.*, 3:99–116 (1984).

Leung, Role of Thrombospondin in Platelet Aggregation, *J. Clin. Invest.*, 74:1764–1772 (1984).

Mumby, Interactions of Thrombospondin with Extracellular Matrix Proteins: Selective Binding to Type V Collagen, *J. Cell Biol.*, 98:646–52 (1984).

Pierschbacher, Cell Attachment Activity of Fibronectin can be Duplicated by Small Synthetic Fragments of the Molecule, *Nature*, 309:30–33 (1984).

Terranova, Modulation of the Metastatic Activity of Melanoma Cells by Laminin and Fibronectin, *Science*, 226:982–85 (1984).

Tam, $S_N1$ and $S_N2$ Mechamisms for the Deprotection of Synthetic Peptides by Hydrogen Fluoride, Int. J. Pept. Prot. Res., 21:57–65 (1983).

Jaffe, Cultured Human Fibroblasts Synthesize and Secrete Thrombospondin and Incorporate it into Extracellular Matrix, *Proc. Natl. Acad. Sci.*, 80:998–1002 (1983).

Raugi, Thrombospondin Synthesis and Secretion by Cells in Culture, *J. Cell Biol.* 95:351–354 (1982).

Geiger, Amine Protecting Groups, *The Peptides*, 3:3–88 (1981).

Lawler, The Release of Heparin Binding Peptides from Platelet Thrombospondin by Proteolytic Action of Thrombin, Plasmin and Trypsin, *Thromb. Res.*, 22:267–79 (1981).

Märki, Total Solid–Phase Synthesis of Porcine Gut Gastrin Releasing Peptide (GRP), a Mammalian Bombesin, *J. Am Chem. Soc.*, 103, 3178–85 (1981).

McPherson, Isolation and Characterization of a Glycoprotein Secreted by Aortic Endothelial Cells in Culture, *J. Biol. Chem.*, 256:11330–36 (1981).

Vale, Characterization of a 41–Residue Ovine Hypothalamic Peptide that Stimulates Secretion of Corticotropin and β–Endorphin, *Science,* 213:1394–1397 (1981).

Lawler, Isolation and Characterization of a High Molecular Weight Glycoprotein from Human Blood Platelets, *J. Biol. Chem.*, 253:8609–16 (1978).

Stewart, *Solid–Phase Peptide Synthesis*, The Chemistry of Solid Phase Peptide Synthesis, 1–26 (1969).

Gasic, Antimetastatic Effects Associated with Platelet Reduction, *Proc. Natl. Acad. Sci.*, 61:46–52 (1968).

Merrifield, Solid Phase Peptide Synthesis: I. The Synthesis of a Tetrapeptide, *J. Am. Chem. Soc.*, 85:2149–2154 (1963).

Dixit, Isolation and Characterization of a Heparin–binding Domain from the Amino Terminus of Platelet Thrombospondin, *J. Biol. Chem.* 259:10100–105 (1954).

* cited by examiner

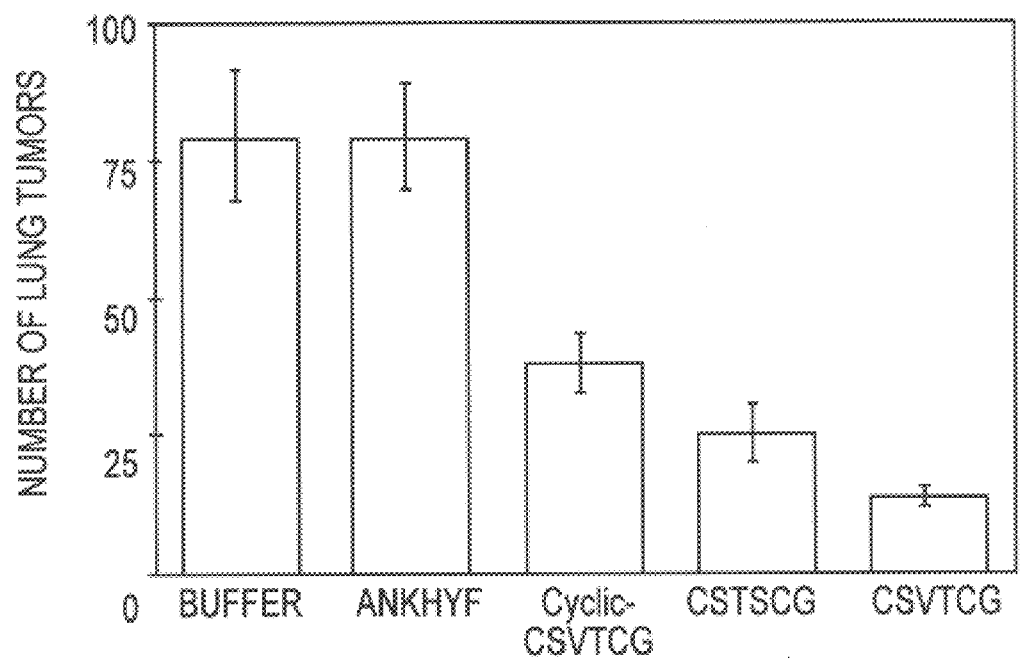
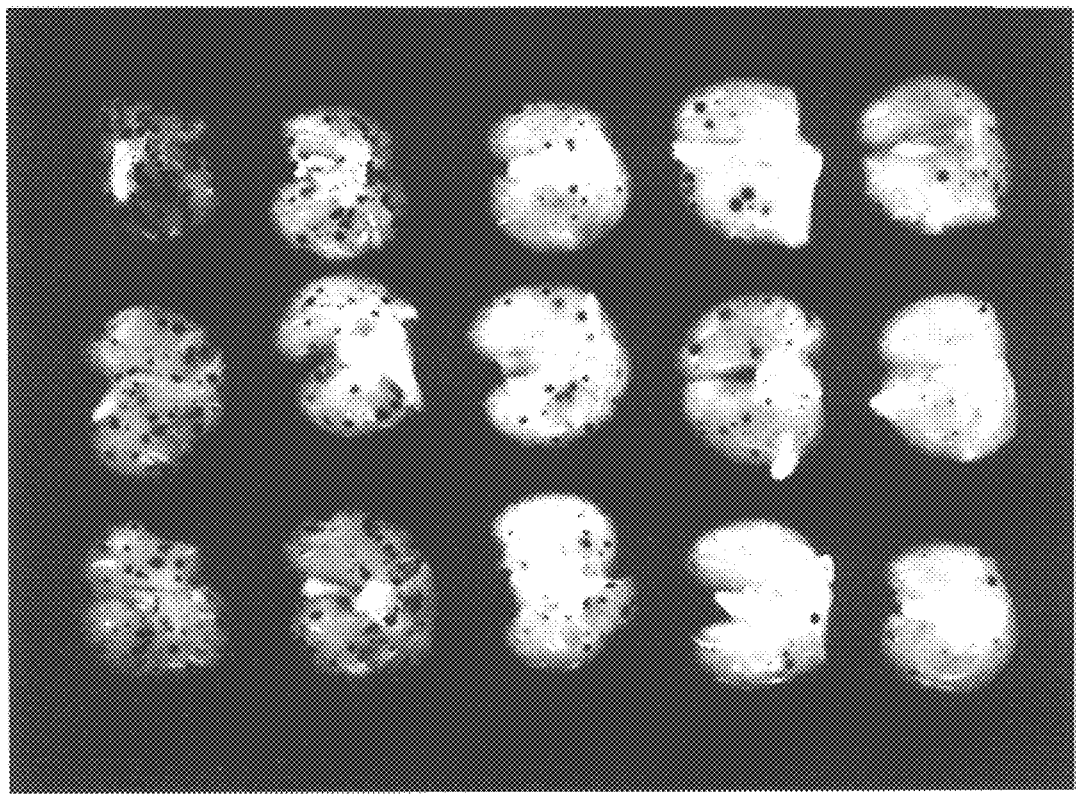
FIG. 12

THE EFFECT OF TSP-1 PEPTIDES ON
MELANOMA METASTASIS

A — SALINE

B — VC (A cm) TGSC (A cm) [ 1 mg IV ]

C — C (A cm) SVTC (A cm)G [ 1 mg IV ]

D — C (A cm) SVTC (A cm)G [ 5 mg IP ]

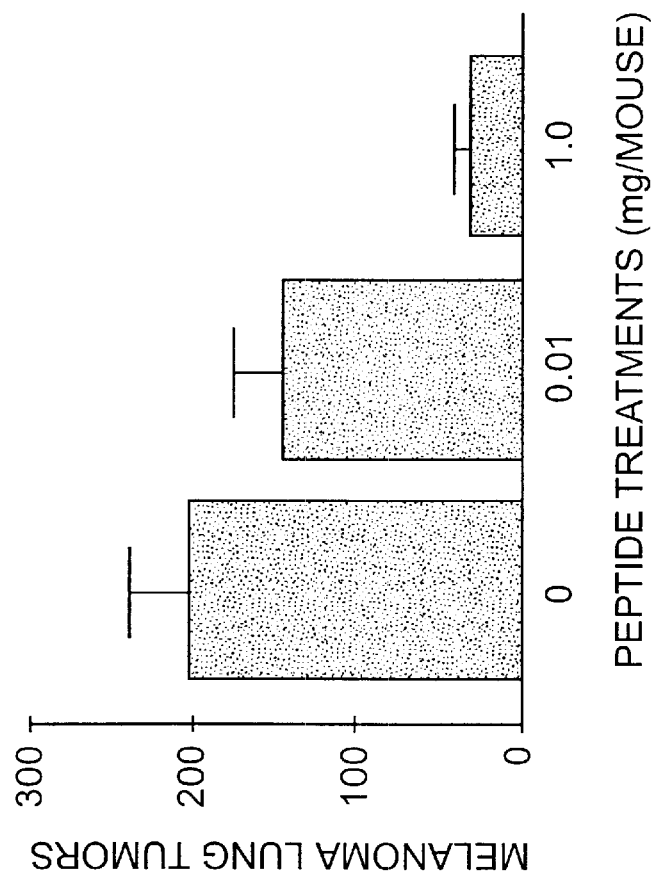

RETROINVERSO POLYPEPTIDES THAT MIMIC OR INHIBIT THROMBOSPONDIN ACTIVITY

This is a division of application Ser. No. 09/197,770, filed Nov. 23,1998, which is incorporated herein by reference.

FIELD OF THE INVENTION

The present invention relates generally to peptide fragments and synthetic analogs of thrombospondin (also known as thrombin sensitive protein or TSP) with thrombospondin-like activity. The peptides mimic or inhibit the biological activity of TSP. These peptides may be used in biological and pharmaceutical applications such as: (a) inhibiting the invasive and metastatic activity of melanoma cells, (b) promoting and inhibiting cellular attachment to tissue culture flasks, (c) promoting wound healing, angiogenesis, and implant acceptance, (d) agents for anti-platelet aggregation, (e) agents for antimalarial activity, and (f) diagnostic reagents in different therapeutic applications, as well as other related areas.

BACKGROUND

Thrombospondin (TSP) is secreted by platelets in response to physiological activators such as thrombin and collagen (Lawler, *Blood*, 67:112–123 (1986)). Other cells also synthesize TSP including fibroblasts (E. A. Jaffe et al., *Proc. Natl. Acad. Sci.*, 80:999–1002 (1983)), smooth muscle cells (Raugi, G. J. et al., *J. Cell Biol.* 95:351–354 (1982)), and endothelial cells (J. McPhearson et al., *J. Biol. Chem.*, 256:11330–11336). TSP has been found in certain tumor tissues, such as melanoma cells (J. Varani et al., *Clin. Expl. Metastais*, 7:265–76 (1989)), squamous lung carcinoma (B. L. Riser et al., *Exp. Cell Res.*, 174:319–329 (1988)) and breast carcinoma (D. A. Pratt et al., *Eur. Nl. Cancer Clin. Oncol.* 25:343–350 (1989)). In addition, certain tumor cells in culture, such as, fibrosarcoma, rhabdomyosarcoma, glioblastoma, Wilm's tumor, neuroblastoma, teratocarcinoma, choriocarcinoma, melanoma, and lung carcinoma have been shown to synthesize TSP (D. F. Mosher, *Annu. Rev. Med.*, 41:85–97 (1990)).

TSP has been shown to play a role in many diverse and clinically important processes, such as: cell migration, wound healing, nerve regeneration, and tumor cell metastasis. TSP has been purified by a number or procedures including exclusion chromatography (Lawler et al., *J. Cell Biol.*, 103:1635–48 (1986)). The complete amino acid sequence of TSP has been deduced from DNA clones prepared by various groups including Lawler et al., *J. Cell Biol.*, 103:1635–48 (1986); Kobayashi et al., *Biochemistry*, 25:8418–25 (1986); Dixit et al., *Proc. Ntl. Acad. Sci.*, 83:5449–53 (1986); and Hennessy et al., *J. Cell Biol.*, 108:729–36 (1989). The structure of TSP is conserved among various animal species as indicated by the fact that the antibody against the human protein cross-reacts with TSP from mouse, rat, pig, cow, sheep, dog, and turkey (H. I. Switalska et al., *J. Lab Clin. Med;* 106:690–700). It is now known that TSP, originally characterized from platelet released proteins, is only one member of a family of structurally related proteins encoded by different genes which include at least four new members designated TSP-2, TSP-3, TSP-4, and TSP-5/COMP (cartilage oligomeric matrix protein). Adams and Lawler, *Current Biology*, 3: 188–190 (1993).

TSP-1 is composed of three identical disulfide-linked chains each consisting of 1,152 amino acids (MW 145,000), and each polypeptide chain is composed primarily of domains consisting of repeating homologous amino acid sequences. Adams and Lawler, *Current Biology*, 3: 188–190 (1993). These domains are a) $NH_2$-terminal globular domain; b) a procollagen homology domain; c) the type 1 or properdin repeat domain, consisting of three repeating sequences homologous to sequences found in properdin; d) the type 2 repeat domain, consisting of three repeating sequences homologous to those in epidermal growth factor; e) the type 3 repeat domain, consisting of seven repeating $Ca^{2+}$-binding sequences, and f) a COOH-terminal globular domain. These distinct domains interact with different cell surface receptors and mediate a variety of cellular processes including cell attachment, migration, proliferation and differentiation. For example, the Cys-Ser-Val-Thr-Cys-Gly (SEQ ID NO: 1) sequence within the type 1 repeats binds the Cys-Ser-Val-Thr-Cys-Gly (SEQ ID NO: 1) receptor, recently identified and isolated from tumor and endothelial cells (Tuszynski et al., *J. Cell Biol.*, 116:209–217 (1992) and Prater et al., *J. Cell Biol.*, 112: 1031–1040 (1991) and is part of the central stalk or protease resistant region of TSP-1.

SUMMARY OF THE INVENTION

The present invention provides thrombospondin fragments and analogs that mimic or inhibit the biological activity of intact thrombospondin and are, thus, useful in a variety of biological, prophylactic or therapeutic areas. These peptides are capable of modifying and inhibiting tumor cell metastasis, cell adhesion and platelet aggregation in mammals in vivo. The peptides are also useful in wound healing, for antimalarial activity, atherosclerosis, thrombotic, and thrombolytic conditions, angiogenesis, and as cell attachment promoters, complement modulators, and diagnostic reagents and in other related areas.

Analogs based on the type I repeat of thrombospondin described by Lawler et al., *Seminars in Thrombosis & Hemostasis*, 13:245–254 (1987), Robson et al., *Nature*, 335:79–82 (1988), and Groundis et al., *Nature*, 335:82–85 (1988) have been shown to have thrombospondin-like activity. Specifically, analogs based around and including at least a portion of the sequence motif Trp-Ser-Pro-Cys-Ser-Val-Thr-Cys-Gly (SEQ ID NO: 2) have been shown to have thrombospondin-like activity.

This invention is directed to polypeptide compounds of formula (I):

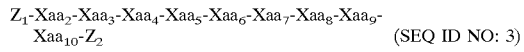

$Z_1$-$Xaa_2$-$Xaa_3$-$Xaa_4$-$Xaa_5$-$Xaa_6$-$Xaa_7$-$Xaa_8$-$Xaa_9$-$Xaa_{10}$-$Z_2$  (SEQ ID NO: 3)

wherein:

$Xaa_2$ is a neutral/non-polar/large/cyclic amino acid residue;

$Xaa_3$ is a neutral/polar/small or neutral/polar/large/non-cyclic or acidic amino acid residue;

$Xaa_4$ is a neutral/nonpolar/large/cyclic or neutral/non-polar/large/non-cyclic or neutral/polar/large/non-cyclic or neutral/polar/small amino acid residue;

$Xaa_5$ is a neutral/polar/small amino acid residue $Xaa_6$ is a neutral/polar/small or neutral/polar/large/non-cyclic amino acid residue;

$Xaa_7$ is a neutral/nonpolar/large/non-cyclic or neutral/polar/large/non -cyclic amino acid residue;

$Xaa_8$ is a neutral/polar/large/non-cyclic or neutral/polar/small amino acid residue;

$Xaa_9$ is a neutral/polar/small amino acid residue;

$Xaa_{10}$ is a neutral/polar/small amino acid residue;

$Z_1$ is hydrogen, amino, acetyl or at least one amino acid residue or the desamino form thereof;

$Z_2$ is hydroxyl, carboxyl, non-amino acids such as agmatine, or at least one amino acid residue, including carboxyamide or alkylamide forms thereof.

Preferably, the polypeptide compounds of this invention have formula (II):

$R_1$-Cys-Xaa$_{11}$-Xaa$_{12}$-Xaa$_{13}$-Cys-$R_2$ (SEQ ID NO: 4)

wherein:

$R_1$ is a protected or unprotected terminal amino group, including hydrogen, amino, acetyl or at least one amino acid residue or the desamino form thereof;

Xaa$_{11}$, Xaa$_{12}$, and Xaa$_{13}$ are the same or different neutral/non-polar/large/non-cyclic or neutral/polar/large/non-cyclic or neutral/polar/small or basic/non-cyclic amino acid residues, preferably selected from the group consisting of valine, threonine, serine, and arginine;

$R_2$ is a protected or unprotected terminal carboxyl group including hydroxyl, carboxyl, or at least one amino acid residue, including carboxyamide or alkylamide forms thereof, preferably selected from the group consisting of lysine, glycine, and arginine;

wherein the structure of the polypeptide is optionally cyclized through a bond between the cysteines, such as a disulfide bond, or a bond between $R_1$ and $R_2$.

This invention also includes polypeptides having the retroinverso form of L-amino acid polypeptides of formulae (I) and (II), i.e, polypeptides comprising D-amino acids in reverse order. In particular, retroinverso peptides of formula Cys-Ser-Val-Thr-Cys-Gly (SEQ ID NO: 1), i.e., d-Gly-Cys-Thr-Val-Ser-Cys (SEQ ID NO: 5) are preferred. Preferably, the cysteine residues are modified by a sulfhydral blocking group, such as —CH$_2$—NH—COCH$_3$, that is adhesive toward melanoma cells. Alternatively, the cysteine residues may be conservatively substituted with another amino acid, e.g., methionine.

Also provided in accordance with aspects of the invention are pharmaceutical compositions, which contain the above-recited polypeptide compounds together with a pharmaceutically acceptable liquid, gel or, solid carrier. Administration of therapeutically effective doses of these compositions can provide effective enhancement or inhibition of thrombospondin-like activity to animals, particularly vertebrates such as mammalian and avian hosts.

BRIEF DESCRIPTION OF THE DRAWINGS

FIG. 12 depicts the effect of synthetic peptides on melanoma tumor cell metastasis.

FIG. 14 depicts the effect of intraperitoneal administration of Cys-(Acm)-Ser-Val-Thr-Cys-(Acm)-Gly (SEQ ID NO: 6) on melanoma lung metastasis after three days of tumor implantation.

DETAILED DESCRIPTION OF THE INVENTION

Figure 1:
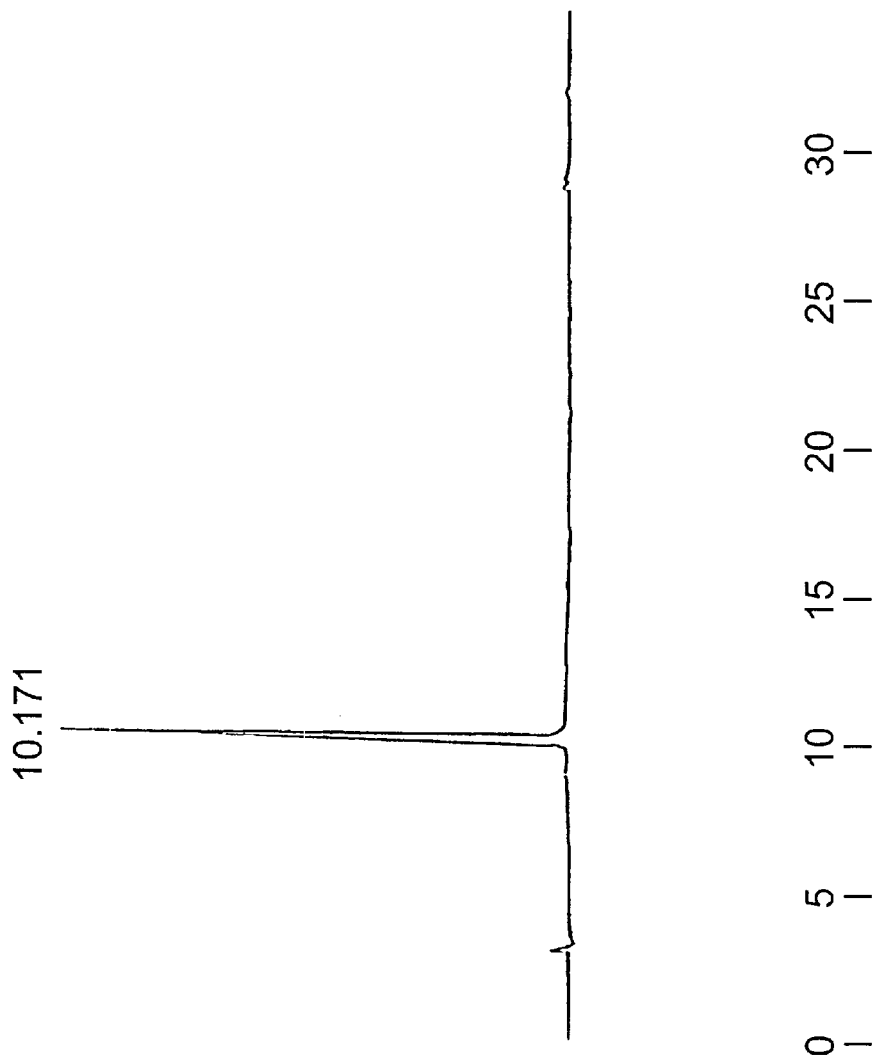
FIG. 1 shows the results of HPLC analysis on peptide Cys-Ser-Val-Thr-Cys-Gly-NH$_2$ (SEQ ID NO: 1).

In accordance with the present invention, fragments and analogs of thrombospondin are provided which are capable of inhibiting or mimicing the activity of thrombospondin in mammals in vivo.

"Thrombospondin-like activity" is defined herein as any activity that mimics or inhibits known biological activities of thrombospondin. These activities include cell-adhesion promoting activity, cell mitogenic activity, cell chemotactic activities, and hemostatic activities and any activities that derive from these activities such as tumor cell, microbial, or parasite metastasis activity, platelet aggregating activity, fibrinolytic activity and immune modulation.

"Antimetastatic activity" is defined herein as the ability to prevent or greatly reduce the extent or size of tumor cell metastasis, or inhibit or cause regression of primary solid tumors.

"Wound healing activity" is defined herein as the ability to increase the rate at which wounds heal or to improve the results of the healing process (i.e., less scarring, good response to tactile stimulus, etc.)

"Atherosclerosis activity" is defined herein as the capacity of thrombospondin to either promote or inhibit the atherosclerotic lesion formation. The atherosclerotic lesion is defined as the degenerative accumulation of lipid-containing materials, especially in arterial walls.

"Antimalaria activity" is defined herein as the ability to inhibit either the cytoadherence of malarial-infected red blood cells to endothelial cells, the malarial sporozoite recognition and entry into hepatocytes, or the malarial merozoite recognition and entry into red blood cells. Antimalarial activity can be demonstrated in the form of a vaccine or a therapeutic that blocks cytoadherence.

"Antithrombotic activity" is defined herein as the ability to either inhibit the aggregation of platelets or to antagonize the formation of a thrombus.

"Thrombolytic activity" is defined herein as the ability to disrupt the structure of a thrombus.

"Angiogenesis activity" is defined herein as the ability to inhibit or enhance the formation of blood vessels or lymph vessels.

"Growth factor activity" is defined herein as the ability to inhibit or promote cell proliferation.

"Cell adhesion activity" is defined herein as the ability to promote or inhibit the attachment of cells, preferably mammalian cells, to a substrate.

"Complement activity" is defined herein as the ability .to activate or block the Complement Cascade Pathway of the immune system.

"Antiviral activity" is defined herein as the ability to prevent or inhibit viral infection by interfering with the ability of the viral particle to bind to cells.

The sequence of amino acid residues of the present polypeptide compounds, the core pentapeptide or nonapeptide, and preferred embodiments thereof, are defined in terms of amino acids of certain characteristics of particular subclasses.

Amino acid residues can be generally subclassified into four major subclasses as follows:

Acidic—the residue has a negative charge due to loss of H ion at physiological pH and the residue is attracted by aqueous solution so as to seek the surface positions in the conformation of a peptide in which it is contained when the peptide is in aqueous medium.

Basic—the residue has a positive charge due to association with H ion at physiological pH and the residue is attracted by aqueous solution so as to seek the surface positions in the conformation of a peptide in which it is contained when the peptide is in aqueous medium.

Neutral/non-solar—the residues a re not charged at physiological pH and the residue is repelled by aqueous solution so as to seek the inner positions in the conformation of a peptide in which it is contained when the peptide is in aqueous medium.

Neutral/polar—the residues are not charged at physiological pH and the residue is attracted by aqueous solution so as to seek the outer positions in the conformation of a peptide in which it is contained when the peptide is in aqueous medium.

It is understood, of course, that in a statistical collection of individual residue molecules some molecules will be charged, and some not. To fit the definition of charged, a significant percentage (at least approximately 25%) of the individual molecules are charged at physiological pH.

Amino acid residues can be further subclassified as cyclic or non-cyclic, a self-explanatory classification with respect to the side chain substituent groups of the residues, and as small or large. The residue is considered small if it contains a total of three carbon atoms or less. Small residues are, of course, always non-cyclic.

For the naturally occurring protein amino acids, subclassification according to the foregoing scheme is as follows:

| | |
|---|---|
| Acidic | Aspartic acid and Glutamic acid |
| Basic/non-cyclic | Arginine and Lysine |
| Basic/cyclic | Histidine |
| Neutral/polar/small | Glycine, Serine, and Cysteine |
| Neutral/polar/large/non-cyclic | Threonine, Asparagine, and Glutamine |
| Neutral/polar/large/cyclic | Tyrosine |
| Neutral/non-polar/small | Alanine |
| Neutral/non-polar/large/non-cyclic | Valine, Isoleucine, Leucine, and Methionine |
| Neutral/non-polar/large/cyclic | Phenylalanine and Tryptophan |

The protein amino acid proline, although within the classification neutral/non-polar/large/cyclic, is not included as an alternative due to its known effects on the secondary conformation of peptide chains.

Certain commonly encountered non-natural amino acids, such as desamino Tyrosine (des Tyr), agmatine (Agm), n-formyl tryptophan (f-Trp), alpha-aminoisobutyric acid (Aib), and sarcosine (Sar), statine, ornithine (Orn), homolysine, homoserine, homoarginine, norleucine (Nle), norvaline may also be incorporated into the compounds of the invention. Desamino tyrosine is incorporated at the N-terminus. Agmatine and statine are incorporated at the C-terminus. Based on the above definition, n-formyl Trp is neutral/non-polar/large/cyclic, Sar is neutral/nonpolar/small, Aib is neutral/non-polar/non-cyclic, Orn is basic/non-cyclic, homolysine is basic/non-cyclic, homoserine is neutral/polar/small, homoarginine is basic/non-cyclic, norleucine is neutral/nonpolar/large/non-cyclic, and norvaline is neutral/nonpolar/large/non-cyclic.

The nomenclature used to describe polypeptide compounds of the present invention follows the conventional practice wherein the amino group is presented to the left and the carboxy group to the right of each amino acid residue. In the formulae representing selected specific embodiments of the present invention, the amino- and carboxy-terminal groups, although not specifically shown, will be understood to be in the form they would assume at physiologic pH values, unless otherwise specified. In the amino acid structure formulae, each residue is generally represented by a three letter designation, corresponding to the trivial name of the amino acid, in accordance with the following schedule:

| Amino Acid | Three-letter Symbol |
|---|---|
| Alanine | Ala |
| Arginine | Arg |
| Asparagine | Asn |
| Aspartic acid | Asp |
| Cysteine | Cys |
| Glutamine | Gln |
| Glutamic acid | Glu |
| Glycine | Gly |
| Histidine | His |
| Isoleucine | Ile |
| Leucine | Leu |
| Lysine | Lys |
| Methionine | Met |
| Phenylalanine | Phe |
| Proline | Pro |
| Serine | Ser |
| Threonine | Thr |

| Amino Acid | Three-letter Symbol |
|---|---|
| Tryptophan | Trp |
| Tyrosine | Tyr |
| Valine | Val |

In the present application, the L-form of any amino acid residue having an optical isomer is intended unless otherwise expressly indicated, e.g., by the symbol "[D-Xaa$_n$]."

Compounds within the scope of the present invention can be obtained by modifying the disclosed formulae in numerous ways, while preserving the activity of the polypeptide compounds thus obtained. For example, while the amino acids of these compounds are normally in the natural L optical isomer form, one or more, usually two or less and preferably one amino acid may be replaced with the optical isomer D form, or a D, L-racemic mixture can be provided in the molecules comprising the polypeptide compound. Also included within the scope of the invention are retro-inverso polypeptides comprising D-amino acids in reverse order from the corresponding L-amino acid counterpart of formula (I) or formula (II).

As one skilled in the art would recognize, branched or cyclical chains may be produced by the formation of a peptide bond with amino acid residues contained within the compounds, e.g., through the formation of a covalent disulfide bond between amino acid residues having sulfur-containing side groups, such as cysteine.

Amino acid residues contained within the compounds of this invention, and particularly at the carboxy- or amino-terminus, can also be modified by methylation, amidation, acetylation, sulfhydral groups, such as Acm (—CH$_2$—NH—COCH$_3$), or substitution with other chemical groups which can, for example, change the circulating half-life, resistance to proteases and solubility of the compounds without adversely effecting their activity.

The polypeptide compounds of this invention may also be modified by conservative substitution of selected amino acids, meaning that a given amino acid residue is replaced by a residue having similar physiochemical characteristics. Examples of conservative substitutions include substitution of one aliphatic residue for another, such as Ile, Val, Leu, or Ala for one another, or substitutions of one polar residue for another, such as between Lys and Arg; Glu and Asp; or Gln and Asn. Other such conservative substitutions, for example, substitutions of entire regions having similar hydrophobicity characteristics, are well known.

The compounds of the invention can also be linked to various drugs or isotopes for purposes of, for example, chemotherapeutics, cytotoxic agent delivery. (Editrice Kurtis s.r.l. (1985); T. A. Connors et al., *Prodrugs in Cancer Chemotherapy Stem Cells,* 13:501–511(1995)). Chemotherapeutic drugs with intracellular sites of action include, but are not limited to, doxorubicin, chlorambucil, adriamycin, dauomycin, methotrexate, vindescine, alpha-amanitin, purothionin, bleomycin, and phenylenediamine mustard. Radioisotopes include, but not limited to, high energy β-emitters, such as $^{131}$I or $^{32}$P, or low energy gamma emitters, such as technetium. Toxins include, but not limited to, ricin, abrin, or diphtheria toxin. The compounds of the claimed invention can also be linked to, for example, human serum albumin, dextran, covalently substituted poly-L-glutamic acid.

As used herein, "protected" terminal amino group, refers to a terminal amino group coupled with any of various amino-terminal protecting groups traditionally employed in peptide synthesis. Examples of suitable groups include acyl protecting groups, for example, formyl, acetyl, benzoyl, trifluoroacetyl, succinyl, and methoxysuccinyl; aromatic urethane protecting groups, for example, benzyloxycarbonyl; and aliphatic urethane protecting groups, for example, tert-butoxycarbonyl or adamantyloxycarbonyl. Gross and Mienhofer, eds., *The Peptides,* vol. 3, pp.3–88 (Academic Press, New York, 1981), disclose numerous suitable terminal amino protecting groups.

As used herein, "protected" terminal carboxyl group, refers to a terminal carboxyl group coupled with any of various carboxy-terminal protecting groups. As will be readily apparent to one skilled in the art, suitable groups include tert-butyl, benzyl or other acceptable groups linked to the terminal carboxyl group through an ester or ether bond.

In 1987, it was shown that TSP-1 functioned as a cell and platelet adhesive protein (Tuszynski et al., *Science,* 236: 1570–1573 (1987)) and that TSP-1 could promote metastasis formation in a murine model of experimental metastasis. Tuszynski et al., *Cancer Res.,* 47: 4130–4133 (1987). Since then structural domains have been identified within the TSP-1 molecule and a new TSP-1 receptor that may mediate cell-cell and cell-substratum interactions operative during the metastatic cascade and the process of angiogenesis. Tuszynski et al., *J. Cell Biol.,* 120: 513–521 (1993).

The CSVTCG-adhesive Domain of TSP-1 and its Role in Metastasis

To identify which TSP-1 sequences mediated the adhesive interactions that promote tumor cell implantation during metastasis, we theorized that TSP-1 or similar sequences might be functioning during the liver implantation of the malarial parasite. We hypothesized that implantation of this parasite occurred through an adhesive mechanism similar to that of TSP-mediated arrest of metastatic tumor cells. In fact, TSP-1 and the malarial circumsporozoite protein, which is believed to mediate the implantation of the malarial parasite, share sequence homologies. (Kobayashi et al., *Biochemistry,* 25: 8418–8425 (1986). The most significant homology is based around the consensus sequence Trp-Ser-Pro-Cys-Ser-Val-Thr-Cys-Gly (SEQ ID NO: 2), which is present in three homologous copies in TSP-1, six copies in properdin, and one copy each in all of the malarial circumsporozoite proteins. Therefore to test whether these TSP-1 sequences played any role in tumor cell metastasis, the cell adhesive activities of synthetic peptides corresponding to these sequences were evaluated in cell adhesion assays, platelet aggregation, and tumor cell lung colonization. Tuszynski et al. *J. Cell Biol.,* 116: 209–217 (1992). We found that a number of peptides homologous to Cys-Ser-Val-Thr-Cys-Gly (SEQ ID NO: ) promoted the adhesion of a variety of normal and tumor cells and inhibited platelet aggregation and tumor cell metastasis, whereas control peptides had no effect. Independently, Prater et al., *J. Cell Biol.,* 112: 1031–1040 (1991) and Rich et al., *Science,* 249: 1574–1577 (1990) also found that peptides containing the Val-Thr-Cys-Gly (SEQ ID NO: 8) sequence possessed cell adhesive activity. Our results further demonstrated that these peptides inhibited tumor lung metastases presumably by competing with endogenous TSP-1 for TSP-1 tumor cell receptor sites. This conclusion was further supported by the observation that anti-Cys-Ser-Thr-Ser-Cys-Gly (SEQ ID NO: 1), which specifically recognized TSP-1, inhibited TSP-dependent cell adhesion, platelet aggregation, and tumor cell metastasis, whereas control IgG had no effect. These results suggest that Cys-Ser-Val-Thr-Cys-Gly (SEQ ID NO: 1) and Cys-Ser-Thr-Ser-Cys-Gly (SEQ ID NO: 9) present in the type I repeats function in the adhesive interactions of TSP-1 that mediate platelet aggregation and tumor cell metastasis.

The Cys-Ser-Val-Thr-Cys-Gly (SEQ ID NO: 1)-Specific TSP-1 Receptor

The TSP-1 receptor specific for the Cys-Ser-Val-Thr-Cys-Gly (SEQ ID NO: 1) residues in the type 1 repeats of TSP-1 was isolated from lung carcinoma by Cys-Ser-Val-Thr-Cys-Gly (SEQ ID NO: 1)-Sepharose chromatography. Tuszynski et al. *J. Cell Biol.,* 120: 513–521 (1993). A single protein peak was isolated from either platelets or tumor cells which also analyzed as a single peak by anion exchange chromatography. The purified protein had a pI of 4.7 and analyzed on SDS-gels as a single 50 kD band under non-reducing conditions and as two protein bands of 50 kD, and 60 kD respectively under reducing conditions. The receptor was cell surface exposed on lung carcinoma cells and activated platelets. Anti-receptor IgG and anti-Cys-Ser-Val-Thr-Cys-Gly (SEQ ID NO: 1) peptide IgG inhibited lung carcinoma cell spreading and adhesion and platelet adhesion on TSP-1 but not on fibronectin and laminin. Tuszynski et al. *J. Cell Biol.,* 120: 513–521 (1993). The Cys-Ser-Val-Thr-Cys-Gly (SEQ ID NO: 1)-specific TSP-1 receptors selectively expressed on invasive cancer cells and capillary endothelial cells and therefore may function in mechanisms of metastasis and angiogenesis. The Cys-Ser-Val-Thr-Cys-Gly (SEQ ID NO: 1) sequence of TSP-1 has been reported to bind CD36 (Asch et al., *Biochem. Biophys. Res. Commun.,* 182: 1208–1217 (1992)), which is another TSP-1 receptor. However, CD36 is not expressed in invasive breast carcinoma. Clezardin et al., *Cancer Res.,* 53: 1421–1430, (1993).

Expression of TSP-1 and the Cys-Ser-Val-Thr-Cys-Gly (SEQ ID NO: 1)-specific Receptor in Human Breast Cancer and Other Neoplasms We investigated the pattern of distribution of the Cys-Ser-Val-Thr-Cys-Gly (SEQ ID NO: 1)-specific receptor and TSP-1 in 11 patients with primary breast ductal carcinoma, 14 patients with benign breast disease (Tuszynski and Nicosia, *Lab. Invest.,* 70: 228–233 (1994) and Roth et al., *Histology & Histopathology,* 12: 1013–1018 (1997), and six patients with primary squamous cell carcinomas of the head and neck. Arnoletti et al., *The American Journal of Surgery,* 168: 433–436 (1994). The pattern of TSP-1 staining was similar to that observed by Wong et al. *Am. J. Pathol.,* 140: 1473–1482 (1992) and Clezardin et al., *Cancer Res.,* 53: 1421–1430 (1993) showing strong localization to the desmoplastic stroma of the malignant tumors with little or no staining of benign breast tissue. The Cys-Ser-Val-Thr-Cys-Gly (SEQ ID NO: 1)-specific receptor was expressed in all the invasive breast ductal carcinomas and squamous cell carcinomas but was absent in normal epithelial cells. Capillary endothelium was focally positive for receptor in regions proximal to carcinoma. The same pattern of positive staining for TSP-1 and the Cys-Ser-Val-Thr-Cys-Gly (SEQ ID NO: 1)-specific receptor was also observed in prostatic cancer and hepatocellular carcinoma.

To determine if the presence or amount of the Cys-Ser-Val-Thr-Cys-Gly (SEQ ID NO: 1)-specific TSP-1 receptor correlated directly with the capacity of tumor cells to invade and metastasize, immunostained carcinoma specimens were subjected to computer-assisted image analysis with the purpose of quantifying the receptor density on the tumor cells. Arnoletti et al., *The American Journal of Surgery,* 168: 433–436 (1994). Our results indicated that those patients with a high positive stain score (77.5±6.3%) for the Cys-Ser-Val-Thr-Cys-Gly (SEQ ID NO: 1)-specific receptor had a decreased overall survival and developed metastatic disease within 16 months of initial treatment (100% correlation). Patients with a low positive stain score (9.3±4.5%) for the receptor were disease-free for at least 2 years. Therefore, the Cys-Ser-Val-Thr-Cys-Gly (SEQ ID NO: 1)-specific TSP-1 receptor, quantified through image analysis of immunohistochemically stained tissue sections, may be a predictive test of clinical outcome in cancer patients.

These studies suggest that the increased expression of TSP-1 and its Cys-Ser-Val-Thr-Cys-Gly (SEQ ID NO: 1)-specific receptor in cancer cells as well as in tumor-associated capillary endothelium correlates with neoplastic transformation. The TSP-rich matrix observed in breast carcinoma may promote tumor cell attachment, tumor cell migration, and angiogenesis, factors important in cancer progression. Taken together the results of our studies provide a rational basis for a role of TSP-1 in tumor angiogenesis and metastasis.

Effect of TSP-1 on Tumor Cell Invasion

Recent results in our laboratory have shown that the adhesion and invasion of carcinoma (Wang et al., *journal of Surgical Research,* 63: 39–43 (1996)) and endothelial cells is potentiated by TSP-1 through an indirect mechanism involving the up-regulation of the plasminogen activator system (Albo et al. *Surgery,* 122: 493–500 (1997)) and matrix metalloproteinases. Qian et al., *Exp. Cell Res.,* 235: 403–412, (1997). In addition, we have shown that an antibody against the Cys-Ser-Val-Thr-Cys-Gly (SEQ ID NO: 1)-specific TSP-1 receptor inhibited human breast tumor progression in athymic mice. Wang et al., *Surgery,* 120: 449–454 (1996).

TSP-1 Blood Levels in Cancer Patients

Because our previous studies demonstrated that TSP-1 injected into the circulation of mice promoted metastasis (Tuszynski et al., *Cancer Res.,* 47: 4130–4133 (1987)) and anti-TSP-1 antibodies inhibited metastasis in the same model (Tuszynski et al., *J. Cell Biol.,* 116:209–217 (1992)), we hypothesized that plasma levels of TSP-1 were elevated in cancer patients. Therefore, we measured TSP-1 plasma levels by indirect ELISA in 20 control subjects, 18 patients with breast cancer, 22 patients with gastrointestinal (GI) cancer, and 17 patients with lung cancer. Tuszynski et al., *Thromb. Haemost,* 67: 607–611 (1992). Control subjects consisted both of healthy individuals and patients with no malignancies. TSP-1 levels of control patients were found to range between 245–440 ng/ml. In contrast, significantly elevated levels of TSP-1 ranging between 590–3650 ng/ml were found in 13/18 (72%) patients with breast cancer, 20/22 (91%) patients with GI malignancies, and 15/17 (88%) with lung cancer. Mean TSP-1 levels in patients with cancer were 2 to 3 fold greater than controls. Increased plasma TSP-1 levels in patients were not due to an increase in the number of platelets since both control and patient groups had platelet counts within the normal range. We obtained similar results in patients with gyneocological (Nathan et al. *Cancer,* 73: 2853–2858 (1994))and colorectal cancers. Yamashita et al., *Cancer,* 82: 632–638 (1998). These results indicate that there is an association between TSP-1 and cancer progression and that TSP-1 may serve as a blood marker for active metastatic disease.

Modulation of Angiogenesis by the Extracellular Matrix: Role of TSP-1

To test the hypothesis that TSP-1 may mediate angiogenesis in vitro, we evaluated TSP-containing fibrin and collagen matrices for their capacity to support angiogenesis and cell growth from explants of rat aorta. Nicosia and Tuszynski, *J. Cell Biol.*, 124: 183–193 (1994). Using the serum-free rat aorta assay, we found that TSP-1 promoted the dose-dependent growth of microvessels and fibroblast-like cells. The effect was TSP-specific because TSP-1 preparations adsorbed with anti-TSP antibody showed no activity. TSP-1 directly stimulated the growth of aortic culture-derived myofibroblasts which in turn promoted microvessel formation when co-cultured with the aortic explants. These results indicate that matrix-bound TSP-1 can indirectly promote angiogenesis through growth promoting effects on myofibroblasts. It is also likely that TSP-1 modulates angiogenesis directly by regulating capillary tube morphogenesis and stabilization as suggested by our recent experiments with isolated endothelial cells. Qian et al., *Exp. Cell. Res.*, 235: 403–412 (1997). In these experiments TSP-1 could either inhibit or stimulate capillary tube formation which was dependent on the amount of metalloproteinase up-regulated by TSP-1. Our results indicate that matrix-bound TSP-1 may be an important stimulator of angiogenesis and wound healing in vivo.

The Role of TSP-1 in Tumor Progression

Accumulating evidence has implicated TSP-1 in tumor progression. Our laboratory first showed that tumor metastases in mice were promoted by TSP-1 and inhibited by anti-TSP-1 antibodies and peptides from the type 1 repeats of TSP-1 containing the sequences Cys-Ser-Val-Thr-Cys-Gly (SEQ ID NO: 1) and Cys-Ser-Thr-Ser-Cys-Gly (SEQ ID NO: 9). Tuszynski et al., *J. Cell Biol.*, 116: 209–217 91992). Recent studies showing increased expression of TSP-1 in the tumor stroma and increased expression of a newly identified human TSP-1 specific receptor in tumor cells suggest a role for TSP-1 and its receptor in tumor progression. Furthermore, the observation that the Cys-Ser-Val-Thr-Cys-Gly (SEQ ID NO: 1)-specific TSP-1 receptor also localizes in the endothelium of tumor capillaries in breast cancer strongly suggests the involvement of TSP-1 in tumor angiogenesis.

The polypeptide compounds of the invention contain the core nonapeptide sequence of formula (I):

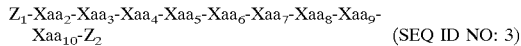

(SEQ ID NO: 3)

wherein:
- $Xaa_2$ is a neutral/nonpolar/large/cyclic amino acid residue;
- $Xaa_3$ is a neutral/polar/small or neutral/polar/large/non-cyclic or acidic amino acid residue;
- $Xaa_4$ is a neutral/nonpolar/large/cyclic or neutral/nonpolar/large/non-cyclic or neutral/polar/large/non-cyclic or neutral/polar/small amino acid residue;
- $Xaa_5$ is a neutral/polar/small amino acid residue;
- $Xaa_6$ is a neutral/polar/small or neutral/polar/large/non-cyclic amino acid residue;
- $Xaa_7$ is a neutral/nonpolar/large/non-cyclic neutral/polar/large/non-cyclic amino acid residue;
- $Xaa_8$ is a neutral/polar/large/non-cyclic or neutral/polar/small amino acid residue;
- $Xaa_9$ is a neutral/polar/small amino acid residue
- $Xaa_{10}$ is a neutral/polar/small amino acid residue;
- $Z_1$ is hydrogen, amino, acetyl or at least one amino acid residue or the desamino form thereof; and
- $Z_2$ is hydroxyl, carboxyl, non-amino acids such as agmatine, or at least one amino acid residue, including carboxyamide or alkylamide forms thereof.

The most preferred sequence of this core nonapeptide is Trp-Ser-Pro-Cys-Ser-Val-Thr-Cys-Gly (SEQ ID NO: 2). Other preferred embodiments include polypeptide compounds wherein:
- $Xaa_2$ is tryptophan or h-formyl-tryptophan;
- $Xaa_3$ is serine, threonine or aspartic acid;
- $Xaa_6$ is proline, glutamic acid, serine or isoleucine;
- $Xaa_5$ is cysteine;
- Xaa6 is serine or asparagine;
- $Xaa_7$ is valine or threonine;
- $Xaa_8$ is threonine or serine;
- $Xaa_9$ is cysteine;
- $Xaa_{10}$ is glycine or serine, including carboxyamide forms thereof.

Particularly preferred are those embodiments wherein the sequence is selected from the group consisting of:

| Compound | Structure | |
|---|---|---|
| p1 | Trp-Ser-Pro-Cys-Ser-Val-Thr-Cys-Gly | (SEQ ID NO:2) |
| p5 | fTrp-Ser-Pro-Cys-Ser-Val-Thr-Cys-Gly-NH₂ | (SEQ ID NO:2) |
| p6 | Trp-Ser-Pro-Cys-Ser-Val-Thr-Cys-Gly-NH₂ | (SEQ ID NO:2) |
| P18 | Trp-Asp-Ile-Cys-Ser-Val-Thr-Cys-Gly | (SEQ ID NO:10) |
| P19 | Trp-Ser-Ser-Cys-Ser-Val-Thr-Cys-Gly | (SEQ ID NO:11) |
| p20 | Trp-Thr-Ser-Cys-Ser-Thr-Ser-Cys-Gly | (SEQ ID NO:12) |
| P11 | Trp-Ser-Pro-Trp-Ser-Glu-Trp-Thr-ser-Cys-Ser-Thr-Ser-Cys-Gly-Asn-Gly-Ile-Gln-Gln-Arg-Gly-Arg | (SEQ ID NO:13) |
| p17 | Trp-Ser-His-Trp-Pro-Trp-Ser-Ser-Cys-Ser-Val-Thr-Cys-Gly-Asp-Gly-Val-Ile-Thr-Arg-Ile-Arg | (SEQ ID NO:14) |
| p12 | Trp-Gly-Pro-Trp-ser-Pro-Trp-Asp-Ile-Cys-Ser-Val-Thr-Cys-Gly-Gly-Gly-Val-Gln-Lys-Arg-Ser-Arg | (SEQ ID NO:15) |
| | Trp-Ser-Pro-Cys-Ser-Val-Thr-Cys-Ser | (SEQ ID NO:16) |
| | Trp-Ser-Gln-Cys-Ser-Val-Thr-Cys-Gly | (SEQ ID NO:17) |

-continued

| Compound | Structure | |
|---|---|---|
| | Trp-Ser-Gln-Cys-Asn-Val-Thr-Cys-Gly | (SEQ ID NO:18) |
| | Trp-Thr-Pro-Cys-Ser-Val-Thr-Cys-Gly | (SEQ ID NO:19) |
| p4 | Asp-Gly-Gly-Trp-Ser-His-Trp-Ser-Pro-Trp-Ser-Ser-Cys-Ser-Val-Thr-Cys-Gln-Asp-Gly-Val-Ile-Thr-Arg-Ile-Arg-Leu-Cys-Asn-Ser-Pro-Ser-Pro-Gln-Met-Asn-Gly-Lys-Pro-Cys-Glu-Gly-Glu-Ala-Arg-Glu-Thr-Lys-Ala-Cys-Lys-Lys-Asp-Ala-Cys-Pro-Ile-Asn-Gly-Gly | (SEQ ID NO:20) |

Also encompassed within the scope of this invention are polypeptides in the retroinverso form of the polypeptides of formula (I), including the retroinverso form of any of the formula (I) polypeptides recited above.

Preferably, the polypeptide compounds of the invention contain the core pentapeptide (d- or l-) sequence of formula (II):

$$R_1\text{-Cys-Xaa}_{11}\text{-Xaa}_{12}\text{-Xaa}_{13}\text{-Cys-}R_2 \quad \text{(SEQ ID NO: 4)}$$

wherein:

$R_1$ is a protected or unprotected terminal amino group, including hydrogen, amino, acetyl or at least one amino acid residue or the desamino form thereof;

$X_{11}$, $X_{12}$, and $X_{13}$ are the same or different neutral/non-polar/large/non-cyclic or neutral/polar/large/non-cyclic or neutral/polar/small or basic/non-cyclic amino acid residues, preferably selected from the group consisting of valine, threonine, serine, and arginine;

$R_2$ is a protected or unprotected terminal carboxyl group including hydroxyl, carboxyl, or at least one amino acid residue, including carboxyamide or alkylamide forms thereof, preferably selected from the group consisting of lysine, glycine, and arginine;

wherein the structure of the polypeptide is optionally cyclized through a bond between the cysteines, preferably a disulfide bond, or a bond between $R_1$ and $R_2$.

Particularly preferred are those embodiments wherein the sequence is selected from the group consisting of:

| | |
|---|---|
| Cys-Ser-Val-Thr-Cys-Gly | (SEQ ID NO: 1) |
| Cys-Ser-Val-Thr-Cys-Gly-NH$_2$ | (SEQ ID NO: 1) |
| Cys-Ser-Val-Thr-Cys-Gly (disulfide linked) | (SEQ ID NO: 21) |
| Cys-Ser-Thr-Ser-Cys-Gly | (SEQ ID NO: 9) |
| Cys-Ser-Thr-Ser-Cys-Gly-NH$_2$ | (SEQ ID NO: 9) |
| Cys-Ser-Thr-Ser-Cys-Gly (disulfide linked) | (SEQ ID NO: 22) |
| Cys-Ser-Thr-Ser-Cys-Gly-NH$_2$ (blocked Cys residues) | (SEQ ID NO: 23) |
| Cys-Arg-Val-Thr-Cys-Gly | (SEQ ID NO: 24) |
| Cys-Arg-Val-Thr-Cys-Gly (disulfide linked) | (SEQ ID NO: 25) |
| Cys-Arg-Val-Thr-Cys-Gly-NH$_2$ | (SEQ ID NO: 25) |
| Arg-Cys-Arg-Val-Thr-Cys-Gly (disulfide linked) | (SEQ ID NO: 26) |
| Cys-Ser-Val-Thr-Cys-Lys | (SEQ ID NO: 27) |
| Cys-Ser-Val-Thr-Cys-Arg-NH$_2$ | (SEQ ID NO: 28) |
| Cys-Ser-Arg-Thr-Cys-Gly | (SEQ ID NO: 29) |
| Cys-Arg-Val-Thr-Cys-Gly-NH$_2$ (disulfide linked) | (SEQ ID NO: 30) |
| Cys-Arg-Thr-Ser-Cys-Gly-NH$_2$ | (SEQ ID NO: 31) |
| Cys-Ser-Thr-Ser-Cys-Arg-NH$_2$ | (SEQ ID NO: 32) |
| Cys-Arg-Val-Thr-Cys-NH$_2$ | (SEQ ID NO: 33) |
| Cys-Ser-Thr-Ser-Cys | (SEQ ID NO: 34) |

Also encompassed within the scope of this invention are polypeptides in the retroinverso form of the polypeptides of formula (II), including the retroinverso form of any of the formula (II) polypeptides recited above.

One particularly preferred embodiment of this invention is a retroinverso peptide of Cys-Ser-Val-Thr-Cys-Gly (SEQ ID NO: 1) that has been modified by sulfhydral groups. This preferred peptide has the formula:

d-Gly-Cys-(Acm)-Thr-Val-Ser-Cys-(Acm)    (SEQ ID NO: 35)

wherein Acm is a sulfhydral blocking group (—CH$_2$—NH—COCH$_3$) that is adhesive toward melanoma cells. The retroinverso peptides of this invention mimic the biological activities of the Cys-Ser-Val-Thr-Cys-Gly (SEQ ID NO: 1) containing peptides which include adhesive, anti-metastatic, anti-invasive, and anti-angiogenic. The retroinverso peptide activity provides strong evidence that the anti-metastatic effects of Cys-Ser-Val-Thr-Cys-Gly (SEQ ID NO: 1) peptides is receptor driven and specific. The retroinverso peptides are stable to proteolytic degradation and metabolism and is orally active, and therefore it is more active in preventing metastasis since it cannot be metabolized.

Compounds within the scope of the present invention can be synthesized chemically by means well known in the art such as, e.g., solid phase peptide synthesis. The synthesis is commenced from the carboxy-terminal end of the peptide using an alpha-amino protected amino acid t-Butylocarbonyl (Boc) protective groups can be used for all amino groups even though other protective groups are suitable. See Stewart et al., *Solid-Phase Peptide Synthesis*, W. H. Freeman Co., San Francisco (1969); Merrifield, *J. Am. Chem. Soc.*, 85: 2149–2154 (1963); Vale et al., *Science*, 213, 1394–1397 (1981); and Marke et al., *J. Am. Chem. Sci.*, 103, 3178 (1981).

Other preparative methods which may be employed include the process of Hughton, *Proc. Natl. Acad. Sci.*, 82:5132 (1981), or another preferable synthesis procedure particularly for small branched or cyclic chain peptides which would include conventional liquid phase processes. The liquid phase process, as well as other synthesis methods are described in *Principle of Peptide Synthesis*, M. Bodansky Ed. (Spring-Verlag 1984). These and other methods of peptide synthesis are also exemplified by U.S. Pat. Nos. 3,862,925; 3,842,067; 3,972,859; 4,105,602; 4,683,291; 4,244,946; and 4,305,872.

Conveniently, compounds may be synthesized using manual techniques or automatically employing, for example, an Applied BioSystems 430A Peptide Synthesizer (Foster City, Calif.) or a Biosearch SAM II automatic peptide synthesizer (Biosearch, Inc., San Rafael, Calif.), following the instructions provided in the instruction manual supplied by the manufacturer.

Although a purity of greater than 95 percent for the synthesized peptide is preferred, lower purity may be acceptable. To obtain cyclic peptides, where for example the two cysteine amino acids are bonded or where the residues contain a disulfide bridge which may be formed by oxidizing of a dilute aqueous solution of the peptide with $K_3[Fe(CN)_6]$. Other means of cyclizing which are known in the art may also be utilized. The stabilized cyclized peptide of the present invention can also be prepared by forming a peptide bond between non-adjacent amino acid residue. A procedure for forming such peptide bond is provided in Schiller et al., *Int. J. Peptide Protein Res.,* 25:171 (1985).

It will be readily appreciated by those having ordinary skill in the art of peptide synthesis that the intermediates which are constructed in accordance with the present disclosure during the course of synthesizing the present compounds are themselves useful compounds and are thus within the scope of the invention.

Alternatively, selected compounds of the present invention can be produced by expression of recombinant DNA constructs prepared in accordance with well-known methods. Such production can be desirable to provide large quantities or alternative embodiments of such compounds.

Compounds of the present invention have thrombospondin-like activity in the intact animal. Compounds of the present invention and compositions containing them which are shown to have the physiological effect of inhibiting or mimicing the effect of intact thrombospondin find use in numerous therapeutic and prophylactic applications, such as cancer therapy, malaria treatment or prevention, wound healing, atherosclerosis, thrombotic or thrombolytic conditions, angiogenesis, complement activation, or cell attachment.

Thus the present invention also provides compositions containing an effective amount of compounds of the present invention, including the nontoxic addition salts, amides and esters thereof, which may, alone, serve to provide the above-recited therapeutic benefits. Such compositions can also be provided together with physiologically tolerable liquid, gel or solid diluents, adjuvants and excipients.

These compounds and compositions can be administered to animals for veterinary use, such as with domestic animals, and clinical use in humans in a manner similar to other therapeutic agents. In general, the dosage required for therapeutic efficacy will range from about 1 $\mu$g to 300 mg/kg, more usually 10 $\mu$g to 30 mg/kg of the host body weight. Alternatively, dosages within these ranges can be administered by constant infusion over an extended period of time, usually exceeding 24 hours, until the desired therapeutic benefits have been obtained.

Typically, such compositions are prepared as injectables, either as liquid solutions or suspensions; solid forms suitable for solution in, or suspension in, liquid prior to injection may also be prepared. The preparation may also be emulsified. The active ingredient is often mixed with diluents or excipients which are physiologically tolerable and compatible with the active ingredient. Suitable diluents and excipients are, for example, water, saline, dextrose, glycerol, or the like, and combinations thereof. In addition, if desired, the compositions may contain minor amounts of auxiliary substances such as wetting or emulsifying agents, stabilizing or pH buffering agents, and the like.

The compositions are conventionally administered parenterally, by injection, for example, either subcutaneously or intravenously. Additional formulations which are suitable for other modes of administration include suppositories, intranasal aerosols, and, in some cases, oral formulations. For suppositories, traditional binders and excipients may include, for example, polyalkylene glycols or triglycerides: such suppositories may be formed from mixtures containing the active ingredient in the range of 0.5% to 10%, preferably 1%–2%. Oral formulations include such normally employed excipients as, for example, pharmaceutical grades of mannitol, lactose, starch, magnesium stearate, sodium saccharin, cellulose, magnesium carbonate, and the like. These compositions take the form of solutions, suspensions, tablets, pills, capsules, sustained release formulations, or powders, and contain 10%–95% of active ingredient, preferably 25%–70%. These oral formulations include formulations designed to protect the peptide until it can be absorbed.

The peptide compounds may be formulated into the compositions as neutral or salt forms. Pharmaceutically acceptable non-toxic salts include the acid addition salts (formed with the free amino groups) and which are formed with inorganic acids such as, for example, hydrochloric or phosphoric acids, or such organic acids as acetic, oxalic, tartaric, mandelic, and the like. Salts formed with the free carboxyl groups may be derived from inorganic bases such as, for example, sodium, potassium, ammonium, calcium, or ferric hydroxides, and such organic bases as isopropylamine, trimethylamine, 2-ethylamino ethanol, histidine, procaine, and the like.

In addition to the compounds of the present invention which display thrombospondin-like activity, compounds of the present invention can also be employed as intermediates in the synthesis of such useful compounds.

The compounds of the invention can be homopolymerized to themselves (i.e., (peptide)$_n$) or, heteropolymerized to one another (i.e., (peptide 1-peptide 2). The compounds can also be cyclized through disulfide or other means. The compounds can also be conjugated to biocompatible polymeric compounds, such as BIOPOL™ (W. R. Grace & Co., Conn.)

While not wishing to be bound by any theory, it is believed that the compositions of the invention act as agonists or antagonists to native thrombospondin. These compounds are also believed to act as agonists or antagonists to circumsporozoite protein, thrombospondin related anonymous protein, antistasin, and properdin complement protein. Further, since the compounds of the invention are small in size (relative to intact thrombospondin) the properties which they exhibit are more likely to be specific in nature, as, opposed to the actions of other generally adhesive compounds such as Arg-Gly-Asp containing compounds (the sequence of which is found in over a hundred proteins) and fibronectin. The side effects of the peptide compounds of the invention are greatly reduced when compared with these broadly adhesive compounds.

As stated previously, the compounds of the invention can be used in a variety of biological, prophylactic or therapeutic areas. It is contemplated that these compounds are useful in prevention or treatment of any disease state or conditions wherein thrombospondin-like activity plays a role. These disease states and conditions include, but are not limited to, metastasis, wound healing, atherosclerosis, malaria, thrombotic conditions, thrombolytic conditions, angiogenesis, cell proliferation, and complement activation. Antibodies directed against the compounds of the invention are also useful as diagnostic reagents, therapeutics, or carriers of other compounds. The compounds can also be used in biomedical devices.

Numerous in vitro and in vivo assays can be used to demonstrate compounds having-thrombospondin-like activity. These assays include, but are not limited to, cell adhesion assays, platelet aggregation assays and cell proliferation assays.

Metastasis

Metastasis is the spread of disease from one part of the body to another unrelated to it, as in the transfer of the cells of a malignant tumor by way of the bloodstream or lymphatics. It is believed that metastasis is effected through a cascade mechanism which includes adhesion of tumor cells to endothelium, retraction of the endothelium, matrix degradation of the basement membrane and invasion of the tumor cells into the bloodstream. Intervention at any phase in this cascade could be beneficial to the treatment or prevention of metastatic cancers.

The native thrombospondin molecule has been shown to potentiate tumor cell metastasis. Tuszynski et al., *Cancer Research*, 47:4130–4133 (1987). The mechanisms by which the thrombospondin potentiation occurs are not presently well understood.

Antimetastasis activity is characterized by the ability of the compounds to bind to melanoma cells in vitro (Tuszynski et al., *Anal. Bio.*, 184:189–91 (1990)), and the ability to reduce the size and number of tumor colonies in vivo. Tuszynski et al. *Cancer Research,* 47:4130–4133 (1987).

The compounds of this invention are useful as antimetastatic agents, particularly useful as antipulmonary metastatic agents. These compounds inhibit the adhesion of metastatic tumor cells, particularly those which are responsive to thrombospondin. The compounds also reduce tumor colony number as well as tumor colony size.

There are a number of mechanisms by which such antimetastatic activity can be occurring. The peptides can be cytotoxic, or inhibit cell proliferation. As inhibitors of cell proliferation, the compounds can act to (1) inhibit mitogenesis, (2) inhibit angiogenesis, or (3) activate the complement pathway and the associated killer cells.

The compounds of the invention can also find use in biomedical devices. Since the compounds have the ability to promote the attachment of metastatic tumor cells, it is possible to coat a biomedical device with the compounds to effect the removal of circulating tumor cells from blood or lymph. The biomedical device is also useful to trap hepatomas.

Another use of the compounds is as a carrier to target toxins, drugs, hormones or imaging agents to metastatic tumor cells for diagnostic or therapeutic purposes. These carriers would also bind to hepatomas.

Wound Healing

Wound healing is the closure of wounds and can be divided into four essential components: inflammation, angiogenesis, collagen deposition and epithelialization. All four components play a role in the healing of wounds.

Wound healing activity is characterized by the ability of the compounds to show angiogenic activity, the ability of the compounds to stimulate collagen deposition and DNA synthesis in the in vivo sponge model or the ability of the compounds to improve wound healing or reduce healing time in an in vivo partial or full thickness wound model.

Atherosclerosis

Atherosclerosis is a disease state which is characterized by the deposition of small fatty nodules on the inner walls of the arteries, often accompanied by degeneration of the affected areas.

Atherosclerosis activity is characterized by the capacity of the compounds to inhibit the development of aortic lesions in rabbits fed a high cholesterol diet.

Malaria

Malaria is an infectious disease caused by any of various protozoans (genus Plasmodium) that are parasitic in the red blood corpuscles and are transmitted to mammals by the bite of an infected mosquito. The compounds of the invention can be used as antimalarial vaccines or as therapeutic agents to block cytoadherence. The peptide compounds of the present invention or cogeners including the peptides of the present invention coupled to the proper immunogenic carrier may function as a potential vaccine or treatment to prevent infection with the malarial organism.

Antimalarial activity is characterized by the ability to inhibit either the cytoadherence of malarial-infected red blood cells to endothelial cells, the malarial sporozoite recognition and entry into hepatocytes, or the malarial merozoite recognition and entry into red blood cells.

Anti-Platelet Aggregation

The compounds of this invention have the ability to specifically inhibit the second stage of platelet aggregation (i.e., the thrombospondin dependent stage of platelet aggregation). This activity allows the compounds to be useful in inhibiting thrombocytopenia caused as a result of disease state (e.g., Acquired Immune Deficiency Syndrome (AIDS), Gray Platelet Syndrome, Essential Thrombocythemia, and Myeloproliferative Syndrome), or that may be induced by therapy (e.g., cancer therapy) or autoimmune diseases. For example, in Thrombotic Thrombocytopenia Purpura (TTP), generally associated with HIV cases, platelets are activated and consumed while producing high serum levels of platelet products. This results in a reduction of platelets in the blood and widespread hemorrhaging. Attentuating platelet activation (i.e., inhibiting platelet aggregation) will effectively inhibit TTP.

Thrombotic Conditions

The compounds of this invention are useful in inhibiting thrombotic activity, and specifically inhibiting platelet aggregation activity. The use of the compounds of the present invention are also thereby useful in inhibiting TTP and thrombocytopenia. These compounds are further useful in preventing coronary artery reocculusion following balloon catheterization. The thrombotic activity associated with the compounds of the invention acts to inhibit platelet aggregation and platelet thrombus formation. Platelets participate in blood coagulation via binding fibrinogen, platelet aggregation and thrombus formation. As anti-thrombotics, these peptides can be useful in the following conditions: myocardial infarction, thromboembolic disease and thrombotic complications due to cancer and cardiovascular disease.

The compounds of this invention modulate the formation and structure of blood clots. Thrombospondin is incorporated into fibrin clots and serves as a substrate for blood clotting Factor XIIIa. An IQQ sequence motif in thrombospondin has been implicated in crosslinking to factor XIIIa. Peptides containing IQQ modulate structure and formation of clots.

Antithrombotic activity is characterized by a number of assays, including 1) inhibition of ADP or thrombin-induced platelet aggregation in washed platelets; 2) inhibition of platelet aggregation in platelet-rich plasma; 3) inhibition of collagen induced platelet aggregation measured in vivo; and 4) inhibition of induced thrombus formation in a carotid artery—in this assay the peptide would delay or prevent occlusion of the artery following thrombus induction.

Alternatively, the compounds of the present invention are useful as potent clotting agents. The effect can be localized and is long lasting. This activity is useful when clotting is necessary (i.e., surgery or in hemophilia).

Thrombolytic Conditions

The thrombolytic activity associated with the compounds of the invention act to alter the structure of a formed thrombus, i.e., dissolution of a blood clot. Thrombolytic activity is characterized as the ability to enhance the dissolution of fibrin in the presence of plasmin (i.e., standard clot lysis assay).

Angiogenesis

Angiogenesis is the formation of blood and lymph vessels. Angiogenesis is a complex process, requiring the sprouting and migration of endothelial cells, their proliferation and their differentiation into a tube like structure and the production of a basement membrane matrix around the vessel. (Herbert et al., *L. Cell Biol.,* 106, 1365–1373 (1988). Angiogenesis is also essential to tumor development and growth. Prevention of angiogenesis can inhibit solid tumor growth. The compounds of this invention are useful in the modulation of angiogenesis, particularly in enhancing wound healing, inhibiting or preventing tumor growth, diabetic retinopathy, and rheumatoid arthritis. Use of the compounds of this invention can inhibit one or more steps in the cascade process of angiogenesis and therefore such peptides can be useful clinically to inhibit metastasis. Standard angiogenesis assays are well known in the art.

Complement Activity

The complement activity associated with the compounds of the invention can play a role in a variety of disease states. The peptides enhance complement-mediated clearance and inactivation mechanisms in both natural and acquired resistance to infection. The complement activity of the peptides serves to promote tumoricidal activity of the complement protein C3b. Additionally, complement proteins are known to contribute to reperfusion injury following heart attacks, and the compounds of the invention can inhibit such activity and are thus useful to lessen heart tissue death and tissue injury during a heart attack.

Antiviral

Viral infections involve attachment to cells of viral particles. The peptides of this invention interfere with viral attachment and are thus useful as antiviral agents.

Antibodies

Compounds of the present invention can also be used for preparing antisera for use in immunoassays employing labeled reagents, usually antibodies. Conveniently, the polypeptides can be conjugated to an antigen by means of dialdehydes, particularly from 4 to 6 carbon atoms and aliphatic, or carbodimide. These compounds and immunologic reagents may be labeled with a variety of labels such as chromophores, fluorophores such as, e.g., fluorescein or rhodamine, radioisotopes such as $^{125}I$, $^{35}S$, $^{14}C$, or $^{3}H$, nonradioactive labeling such as chemiluminescent labeling, or magnetized particles, by means well known in the art.

These labeled compounds and reagents, or labeled reagents capable of recognizing and specifically binding to them, can find use as, e.g., diagnostic reagents. Samples derived from biological specimens can be assayed for the presence or amount of substances having a common antigenic determinant with compounds of the present invention.

Thrombospondin levels are elevated in the serum of patients with metastatic breast and colon cancer. Antibodies against the peptides of the invention can be useful as reagents in diagnostic/prognostic assays for various types of cancer, including but not limited to, gastrointestinal tract (gastric, colonic, and rectal) carcinomas, breast carcinomas and hepatic carcinomas.

In addition, monoclonal antibodies can be prepared by methods known in the art. The polyclonal and monoclonal antibodies can find therapeutic use in a number of cancer therapies. First, the antibodies can be used to sequester thrombospondin. This is useful since thrombospondin mediates tumor cell metastasis. Second, the antibodies can be used to block thrombospondin present on the tumor cell surface. Third, cytotoxic drugs, hormones, or imaging agents can be coupled to the antibodies for use in cancer therapy. Fourth, a biomedical device can be coated with the antibodies to remove excess thrombospondin from serum or to remove cells which bear thrombospondin on the cell surface.

The peptides of the invention can also be used to isolate thrombospondin cell surface receptors from extracts of cells or cell membranes. The thrombospondin cell surface receptors can be used to develop better thrombospondin analogs or to remove excess thrombospondin from serum.

Adhesion and Cell Attachment

The peptides of the present invention can be used for preparing a surface for optimal cell culture, and for prosthetic materials to promote bonding with surrounding tissue. These peptides can be useful as a cell attachment protein to provide a substrate to which cells will attach by treating a hydrophobic surface such as untreated synthetic plastic resin and especially materials which are used for different membrane applications, e.g., nitrocellulose or polysulfone or comparable material with the peptide. The cell attachment properties of the peptides can also be used to couple polypeptides covalently to a solid support such as gels or synthetic resins or long chain polysaccharide. This latter approach can be used for different affinity chromatography applications. Another important application of using such peptides are the use of the peptide in commercial cell attachment surfaces, wherein the particles are coated with gelatin, making it possible to grow the same adherent cells in a much smaller volume of media than would be possible in dishes. Medical devices can be designed for use with such peptides to attach cells to the surface in vivo, or even to promote the growth of a desired cell type on particular surfaces prior to grafting. An example of this is attachment of islet cells to a membrane or growth of endothelial cells on a prosthetic blood vessel or vascular graft. Such peptides can find uses in coating a patch graft or the like for aiding in wound healing.

As herein described, cell adhesion activity is defined as the ability to promote or inhibit the attachment of cells to a substrate. It is believed that this dual function is achieved because the peptides of the present invention bind to the cells, and occupy all of the binding sites available on the cells. Therefore, when used for substrates, the peptides of the present invention find use to promote adhesion to substrates. The peptides of the present invention are also useful in effectively inhibiting cell-to-cell adhesion because the peptides occupy all of the available binding sites on the cells, thereby blocking these cells from binding to one another.

For example, endothelial cells resident on a vessel wall may be considered as constituting a substrate to which sickled red blood cells adhere resulting in vaso-occlusive crisis in sickle cell disease. Compounds which bind to both the endothelial cells and the sickled red blood cells can serve to block this adherence.

Sickle cell disease may, accordingly, be treated with compounds of the present invention due to their ability to essentially inhibit cell adhesion/aggregation. This is supported by recent studies. Hebble has shown that the adherence of sickle erythrocytes to human endothelial cells in vitro correlated directly with the clinical severity of vasoocclusive morbidity in individual patients. *BMJ,* 302:1551 (1991). In addition, further studies directed to thrombospondin have shown that thrombospondin, and peptides of thrombospondin are effective in inhibiting cell adhesion, and may have therapeutic-use in sickle cell disease. *Blood,* 80(10):2634–2642 (1992).

Therefore, compounds such as those of the present invention, which inhibit the adherence of cells, would be useful in treating the sickle cell disease state, as well as other disease states that operate by cell adhesion.

The following examples are provided by way of illustration, rather than implying any limitation of the subject matter.

EXAMPLES

The peptides of this invention can be synthesized by conventional methods of peptide synthesis. A preferred method is the solid phase synthesis described in *Int. J. Pept. Proc. Res.* 21, 57–63 (1983). Also preferred is the solid phase synthesis of Merrified, *J. Amer. Chem. Soc.* 85, 2149–2154 (1963); *Science,* 150, 178–185 (1965). Solid phase synthesis is generally initiated from the C-terminal of the peptide by coupling a protected alpha amino acid to a suitable resin, e.g., phenylacetamidomethyl (PAM) polystyrene resin, or p-methylbenzhydrylamine (mBHA) resin when synthesizing a peptide with a C-terminal carboxyamide. In the present invention, the peptides were synthesized by solid-phase techniques performed on an Applied Biosystems 430A Peptide Synthesizer (Foster City, Calif.) using t-butyloxycarbonyl (t-Boc) alpha amino-group protected amino acids in accordance with the instructions of the manufacturer. During this synthesis, suitable amino acid side-chain protecting groups are used as needed. Thus, aspartic acid is protected on the beta-carboxyl group as the benzyl ester and arginine is protected on the guanidino group by tosyl. After the desired peptide has been synthesized, the peptide is cleaved from the resin and protecting groups are removed by treatment with a reagent such as hydrogen fluoride (HF). The peptide can then be purified by high performance liquid chromatography (HPLC) or other such methods of peptide purification. Background information on the established procedures for solid phase peptide synthesis can be found in Stewart and Young, *Solid Phase Peptide Synthesis,* W. H. Freeman & Co., San Francisco, (1969).

In accordance with the above description, the following procedures were used for the chemical synthesis of novel synthetic peptides:

Procedure A 0.1 mmole of selected Boc-$Xaa_n$-$OCH_2$-PAM Resin (0.2–0.8 mmole/g resin) (Applied Biosystems, Inc.) or p-mBHA Resin (0.2–0.7 mmole/g resin) (Applied Biosystems, Inc.) is treated according to Schedule A for the incorporation of the Boc-$Xaa_{n-1}$ or Boc-$Xaa_n$, respectively.

Schedule A. Small-scale Rapid Cycle Chemistry
1. 5-minute neat TFA (trifluoroacetic acid) wash
2. 40s DMF flow wash
3. 1-minute treatment with 20% DIEA (diisopropyl ethyl amine) in DMF (dimethyl formamide)
4. 40s DMF flow wash
5. Addition of 1–10 equivalents of preformed symmetric anhydride of a suitable protected t-boc amino acid dissolved in DMF
6. 10-minute coupling period
7. 40s DMF flow wash Procedure B 0.5 mmole of selected Boc-$Xaa_n$-$OCH_2$-PAM Resin (0.2–0.8 mmole/g resin) (Applied Biosystems, Inc.) or p-mBRA Resin (0.2–0.7 mmole/g resin) (Applied Biosystems.) is treated according to Schedule B for the incorporation of the Boc-$Xaa_{n-1}$ or BOC-$Xaa_n$, respectively.

Schedule B. Large-scale NMP (N-methylpyrrolidone)/HOBT (1-hydroxybenzotriazole) Chemistry
1. 3-minute wash with 30% TFA in DCM (dichloromethane).
2. 17-minute wash with 50% TFA in DCM.
3. Wash 5× with DCM.
4. 1-minute wash with 5% DIEA in DCM.
5. 1-minute wash with 5% DIEA in NMP.
6. Wash 5× with NMP.
7. Addition of 1–4 equivalents of HOBT-ester of a suitably protected t-boc amino acid dissolved in NMP.
8. 30-minute coupling period.
9. Addition of DMSO to 20%-and subsequent 16-minute coupling period.
10. Addition of 3.8 equivalents DIEA and subsequent 7-minute coupling period.
11. Wash 3× with DCM.
12. Wash with 10% acetic anhydride, 5% DIEA in DCM for 2 minutes.
13. Wash with 10% acetic anhydride in DCM for 4 minutes.
14. Wash 4× with DCM.

Example 1

Synthesis of the Peptide Sequence Cys-Ser-Val-Thr-Cys-Gly (SEQ ID NO: 1) with C-Terminal Amide An appropriate resin 4-methylbenzhydrylamine (MBHA) for C-terminal amide was sealed into polypropylene mesh packets (64$u$). All packets were placed into a common vessel with $CH_2Cl_2$ and vigorously shaken to wash and swell the resin. All subsequent steps involved vigorous shaking to ensure adequate solvent transfer. The N-α-butoxycarbonyl was then removed by acidolysis using 55% trifluoroacetic acid (TFA) /$CH_2Cl_2$ for 30 minutes leaving the a-amino acid group in the TFA salt form. The packets were then washed with $CH_2Cl_2$ (2×), IPA (2×), and $CH_2Cl_2$ (2×) to remove excess TFA and prepare for neutralization. The IFA salt was neutralized by washing the packets three times with 5% diisopropylethylamine in $CH_2Cl_2$ for 2 minutes each. This was followed by two washes with $CH_2Cl_2$ to remove excess base. Packets were then removed from the common vessel and added to their respective 0.2 M amino acid solutions which were prepared from computer generated information prior to neutralization. An equal volume of 0.2 M dipropylcarbodiimide was then added to activate the coupling reaction. After coupling at room temperature for 1 hour, the packets were washed with dimethylformamide and $CH_2Cl_2$ and returned to the common vessel. This process was repeated for each amino acid. Cleavage occurred by reacting the peptide with 92.5% hydrogen fluoride/7.5% anisole at −10° C. to 0° C. over 90 minutes. Anisole was used as a scavenger to react with carbocations produced as a result of the side chain protecting group removal. This solution was then removed using a strong flow of $N_2$ followed by the use of aspirator vacuum, while maintaining the temperature at 0° C. Residual anisole was removed with 2 ethyl ether washes. The peptide was then extracted using 10% acetic acid.

The purity of the crude peptide was checked by analytical RP-HPLC using a Beckman System Gold with a Vydac C-18 column at a flow rate of 1 ml/min. The solvent system used was 0.05% aqueous TFA(A) and 0.05% TFA in acetonitrile (B) with a gradient of 5–65% B in 30 minutes measuring the absorbance at 215 µm). Purification was performed on Waters delta prep. 3,000 preparative HPLC with a Waters prep. Pak Nodule Radial Compression C1 8 column (25 cm×5 cm, 10–20µ). The solvent system was 0.05% aqueous TFA (A) and 0.05% TFA in acetonitrile (B). Various linear gradients were used measuring the absorbance at 230 nm and collecting 40 ml fraction. The fractions were then analyzed on the Beckman analytical system. The desired fractions were pooled and lyophilized. The final dry product was analyzed one more time using analytical RP-HPLC. Typical HPLC chromatograms for this peptide after purification are shown in FIG. 1.

Example 2

Chemical Synthesis of the Peptide Sequence Cys-Ser-Val-Thr-Cys-Gly (SEQ ID NO: 1) Acid An appropriate resin phenylacetamidomethyl (PAM) for C-terminal acid was sealed into polypropylene mesh packets (64µ). All packets were placed into a common vessel with CH2C12 and vigorously shaken to wash and swell the resin. All subsequent steps involved vigorous shaking to ensure adequate solvent transfer. The N-α-butoxycarbonyl is then removed by acidolysis using 55% trifluoroacetic acid (TFA)/ $CH_2Cl_2$ for 30 minutes leaving the a-amino acid group in the TFA salt form. The packets were then washed with $CH_2Cl_2$ (2×), IPA (2×), and $CH_2Cl_2$ (2×) to remove excess TFA and prepare for neutralization. The TFA salt was neutralized by washing the packets three times with 5% diisopropylethylamine in $CH_2Cl_2$ for 2 minutes each. This was followed by two washes with $CH_2Cl_2$ to remove excess base. Packets were then removed from the common vessel and added to their respective 0.2 M amino acid solutions which were prepared from computer generated information prior to neutralization. An equal volume of 0.2 M diisopropylcarbodiimide was then added to activate the coupling reaction. After coupling at room temperature for 1 hour, the packets were washed with dimethylformamide and $CH_2Cl_2$, and returned to the common vessel. This process was repeated for each amino acid. Cleavage occurred by reacting the peptide with 91.5% hydrogen fluoride/7.5% anisole at −10° C. to 0° C. over 90 minutes. Anisole was used as a scavenger to react with carbocations produced as a result of the side chain protecting group removal. This solution was then removed using a strong flow of $N_2$ followed by the use of an aspirator vacuum, while maintaining the temperature at 0° C. Residual anisole is removed with two ethyl ether washes. The peptide is then extracted using 10% acetic acid.

Figure 2:
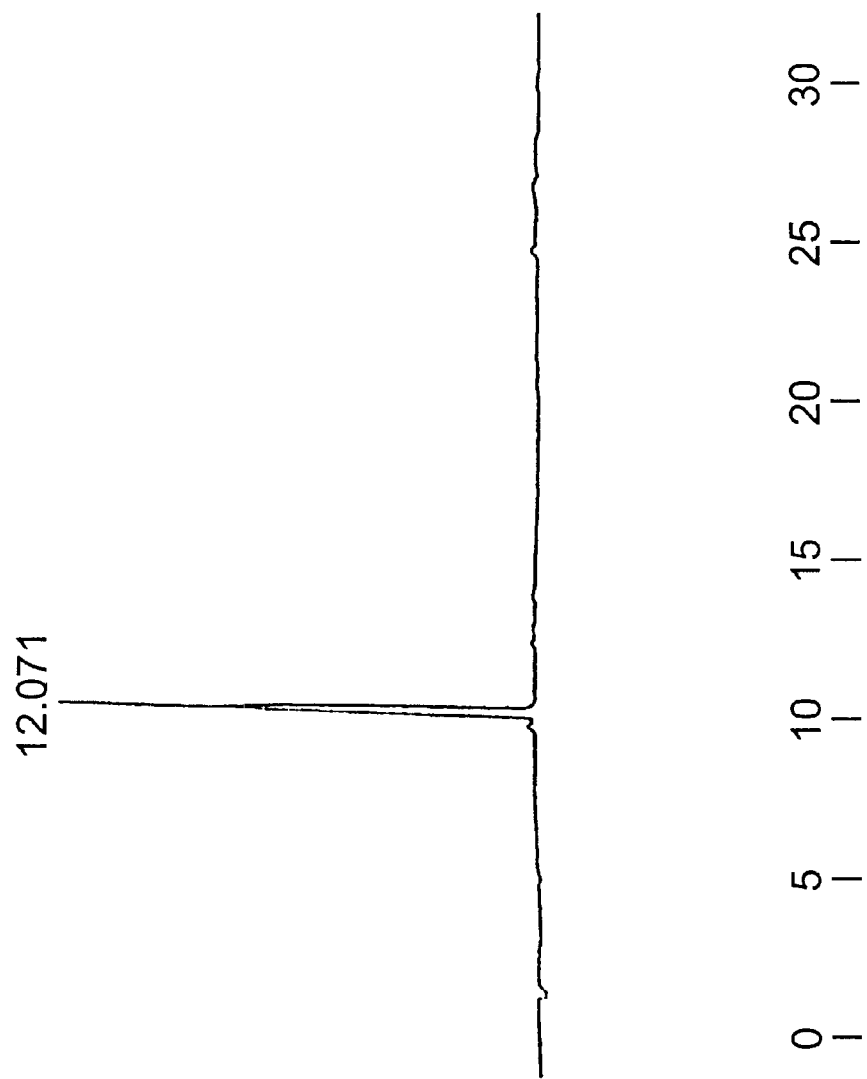
FIG. 2 depicts the results of HPLC analysis on peptide Cys-Ser-Val-Thr-Cys-Gly (SEQ ID NO: 1).

The purity of the crude peptide was checked by analytical RP-HPLC using a Beckman System Gold with a Vydac C-18 column at a flow rate of 1 ml/min. The solvent system used was 0.05% aqueous TFA(A) and 0.05% TFA in acetonitrile (B) with a gradient of 5–65% B in 30 minutes measuring the absorbance at 215 nm. Purification was performed on Waters delta prep. 3,000 preparative HPLC with a Waters prep. Pak Nodule Radial Compression C18 column (25 cm×5 cm, 10–20µ). The solvent system was 0.05% aqueous TFA (A) and 0.05% TFA in acetonitrile (B). Various linear gradients were used measuring the absorbance of 230 nm and collecting 40 ml fraction. The fractions were then analyzed on the Beckman analytical system. The desired fractions were pooled and lyophilized. The final dry product was analyzed one more time using analytical RP-HPLC. Typical HPLC chromatogram for this peptide after purification are shown in FIG. 2.

Example 3

Synthesis of Cyclic Cys-Ser-Val-Thr-Cys-Gly (SEQ ID NO: 1) Acid

Cyclization of Cys-Ser-Val-Thr-Cys-Gly (SEQ ID NO: 1) peptide was accomplished by dissolving the crude peptide of Example 2 (52 mg) in 500 ml deoxygenated water and the pH was adjusted to 8.5 with 28% $NH_4OH$ (solution A) $K_3Fe(CN)_6$ (1.75 g) was dissolved in 100 ml deoxygenated water and the pH was adjusted to 8.5 with 28% $NH_4OH$. This solution is called solution B.

Solution A was dropped into solution B in 2 hours and the mixture was allowed to stir 1 more hour. The pH was then adjusted to 4 with 10% AcOH and the solution was injected onto a prep-HPLC. After purification a 28 mg peptide of 95% purity has been recovered.

Figure 3:
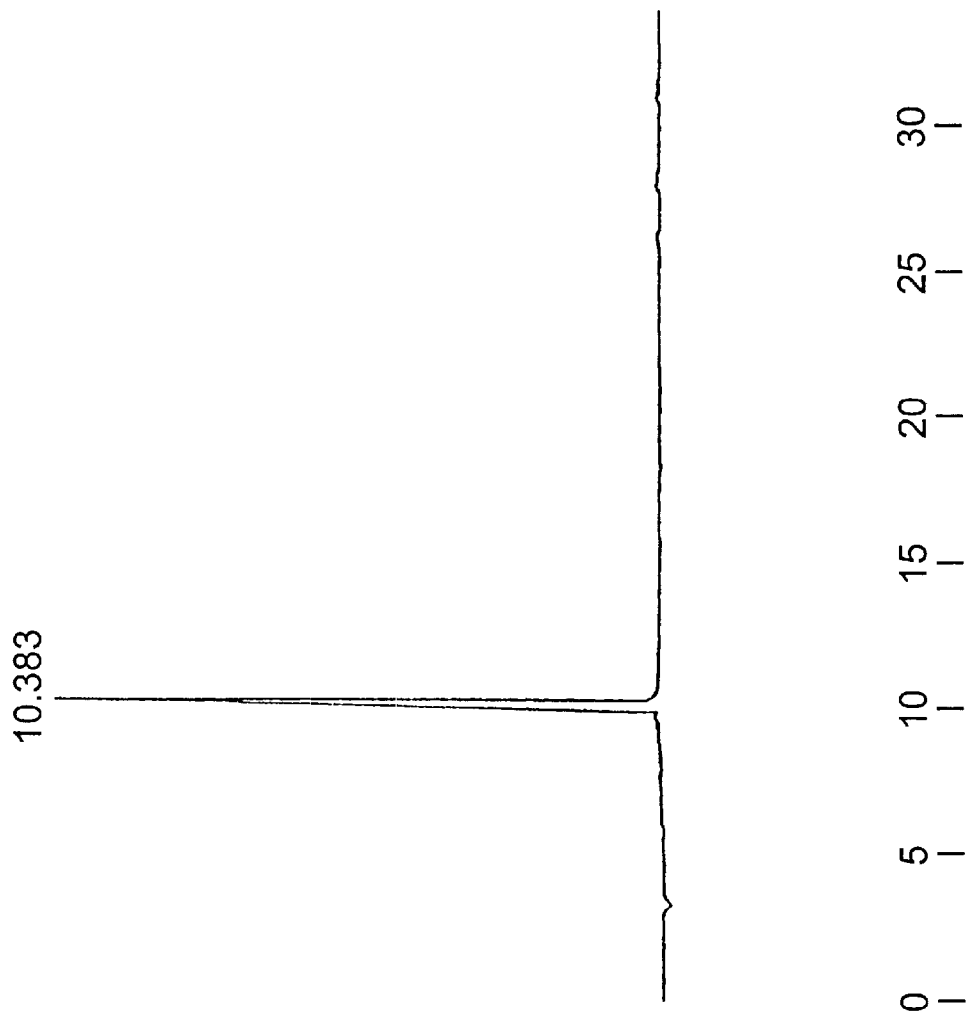
FIG. 3 shows the results of HPLC analysis on peptide Cys-Ser-Val-Thr-Cys-Gly (SEQ ID NO: 1) which is cyclized via a disulfide bond.

The composition of the cyclic material was confirmed by analytical reverse phase HPLC and by Feb-MS. Typical HPLC chromatography is presented in FIG. 3.

Example 4

Chemical Synthesis of Additional Peptides

Following the procedures outlined in Examples 1–3 and in *Int. J. Pept. Proc. Res.* 21, 57–65 (1983) with appropriate modification, the following peptides were synthesized. All peptides of the invention were tested for endotoxins using standard LAL assay procedures and found to be endotoxin free.

| | |
|---|---|
| Cys-Ser-Thr-Ser-Cys-Gly | (SEQ ID NO: 9) |
| Cys-Ser-Thr-Ser-Cys-Gly-NH$_2$ | (SEQ ID NO: 9) |
| Cys-Ser-Thr-Ser-Cys-Gly (disulfide linked) | (SEQ ID NO: 22) |
| Cys-Ser-Thr-Ser-Cys-Gly-NH$_2$ (blocked Cys residues) | (SEQ ID NO: 23) |
| Cys-Arg-Val-Thr-Cys-Gly | (SEQ ID NO: 24) |
| Cys-Arg-Val-Thr-Cys-Gly (disulfide linked) | (SEQ ID NO: 25) |
| Cys-Arg-Val-Thr-Cys-Gly-NH$_2$ | (SEQ ID NO: 25) |
| Arg-Cys-Arg-Val-Thr-Cys-Gly (disulfide linked) | (SEQ ID NO: 26) |
| Cys-Ser-Val-Thr-Cys-Lys | (SEQ ID NO: 27) |
| Cys-Ser-Val-Thr-Cys-Arg-NH$_2$ | (SEQ ID NO: 28) |
| Cys-Ser-Arg-Thr-Cys-Gly | (SEQ ID NO: 29) |
| Cys-Arg-Val-Thr-Cys-Gly-NH$_2$ (disulfide linked) | (SEQ ID NO: 30) |
| Cys-Arg-Thr-Ser-Cys-Gly-NH$_2$ | (SEQ ID NO: 31) |
| Cys-Ser-Thr-Ser-Cys-Arg-NH$_2$ | (SEQ ID NO: 32) |
| Cys-Arg-Val-Thr-Cys-NH$_2$ | (SEQ ID NO: 33) |
| Cys-Ser-Thr-Ser-Cys | (SEQ ID NO: 34) |

Example 5

Adhesion of $B_{16}F_{10}$ Melanoma Cells to TSP and Peptides

In this example a series of peptides were tested to determine the abilities of the peptides to bind $B_{16}F_{10}$ melanoma cells as compared to thrombospondin and fibronectin. It is believed that thrombospondin acts in metastasis through its adhesive properties. An assay was developed, generally in accordance with the disclosure of Tuszynski et al. *Anal. Bio.,* 84:189–91 (1990), which evaluates the ability of melanoma cells to adhere to the thrombospondin fragments or analogs of the invention. In this assay, thrombospondin (purified by the method of Tuszynski et al., *J. Biol. Chem.,* 260:12240–5 (1985) and fibronectin (Sigma Chemical Co., Missouri) served as positive controls, bovine serum albumin (BSA) (Sigma Chemical Co.) served as the negative control. Thrombospondin analogs of the invention were synthesized as described in Examples 1–4. Two micrograms of peptide or control proteins were air dried overnight on the wells of a 96-well microtiter plate. Wells were then washed with HEPES-buffered saline and blocked for 1 hour with 1% fatty acid free BSA in HEPES-buffered saline.

The mouse $B_{16}F_{10}$ melanoma cells were grown and harvested during log phase of growth using standard procedures. The harvested cells were washed two times in serum-free Dulbecco's minimum essential medium (DMEM) (Flow Laboratories) and suspended in HEPES-buffered saline, containing 5 mM glucose and 100 µM $MgCl_2$ at a final concentration of $4\times10^5$ cells/ml. Of the cell suspension 200,000 cells per well was added to each well of the microtiter dish containing the various ligands and the dish incubated at 37° C. in a $CO_2$ incubator for 30 minutes. Nonadherent cells were removed by aspiration and the wells washed three times with 200 µl of PBS (phosphate buffered saline). The total cell-associated protein was determined by dissolving the attached cells directly in the microtiter wells with 200 Al of the Pierce BCA (bicinchoninic acid) working solution (Pierce Chem. Co. Booklet No. 23225 (1987)). The plate was covered with an adhesive mylar sheet (Flow Labs) and incubated at 60° C. for 30 minutes. Plates were allowed to cool to room temperature, cover sheets were removed, and the absorbance of each well was determined at 562 nm with a microtiter plate reader (Biotek, Burlington, Vt.) Absorbances were converted to number of adherent cells by means of an empirically determined conversion factor.

Figure 4:
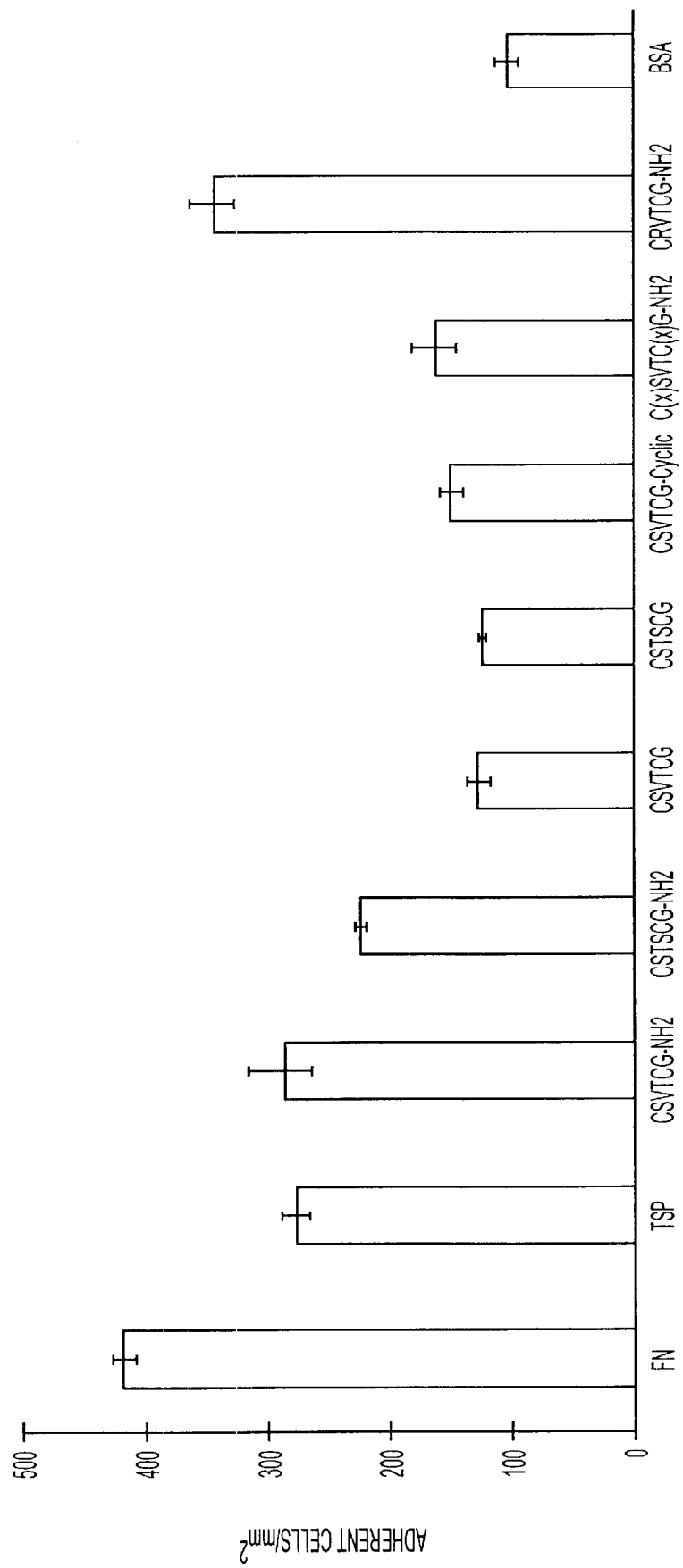
FIG. 4 depicts the ability of the peptides of the invention to inhibit adhesion of melanoma cells.

The results shown in FIG. 4 indicate that the peptides of the invention display adhesive properties.

Example 6

Figure 5:
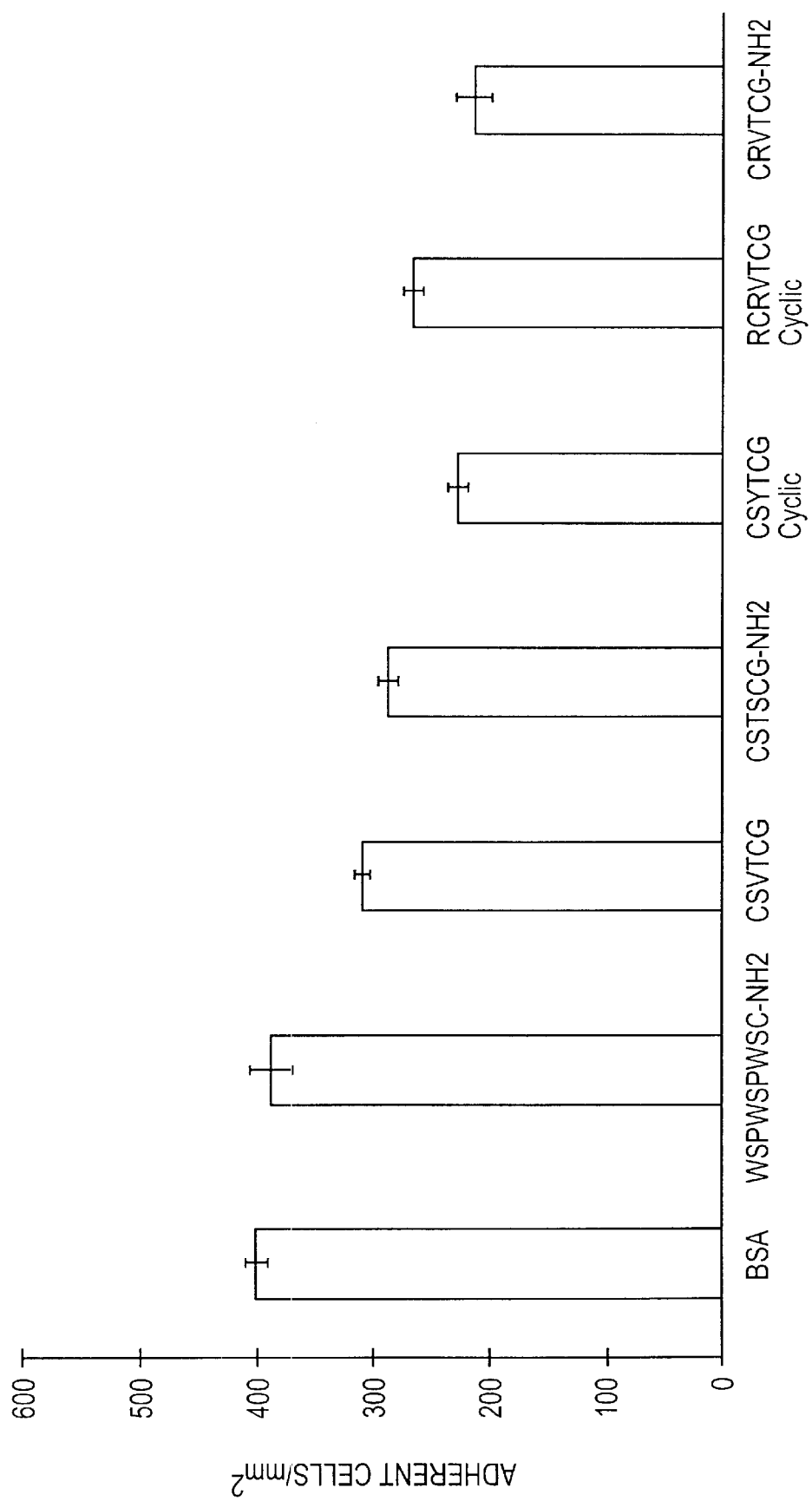
FIG. 5 depicts the ability of the peptides of the invention to act in collagen dependent melanoma cell adhesion.

The Effect of Peptides on Collagen Dependent Adhesion of $B_{10}F_{10}$ Melanoma Cells Two micrograms of collagen in 5 mM acetic acid were adsorbed to wells overnight at 4° C. Wells were then washed with HEPES-buffered saline and blocked for 1 hour with 1% fatty acid free bovine serum albumin (BSA) in HEPES buffered saline. A suspension of $B_{16}F_{10}$ cells in HEPES-buffered saline, containing 5 mM glucose (200,000 cells per well) and 100 µM $MnCl_2$ were preincubated for 15 minutes at 37° C. in either buffer or in buffer containing 100 µg/ml peptide or 100 µg/ml BSA. The cell suspensions were then added to collagen-coated wells and incubated for 30 minutes at room temperature. Non-adherent cells were removed by aspiration, and adherent cells determined by measurement of cell-associated protein as previously described in Example 5. The results shown in FIG. 5 indicate that the peptides of the invention inhibit the binding of the melanoma cell to collagen.

Example 7

The Effect of Peptides on $B_{16}F_{10}$ Lung Tumor Cell Metastasis

The in vivo model used to demonstrate the antimetastatic activity of the peptide compounds of the invention is described by Tuszynski et al. *Cancer Res.,* 47:4130–4133 (1987). Briefly, C57 black mice were intravenously injected with; $1\times10^5$ $B_{16}F_{10}$ mouse melanoma cells in the presence of either control buffer (Hepes buffered saline, pH 7.4), or 1 mg of the designated peptide compound of the invention. Five or six animals were used for each compound. Peptides tested in the assay had no effect on cell viability as measured by Trypan blue dye exclusion. In addition, the peptides at 1 mg/ml did not effect cell growth after 24 hours of co-culture. After 14 days, the mice were sacrificed and the number of lung tumors counted.

Figure 6:
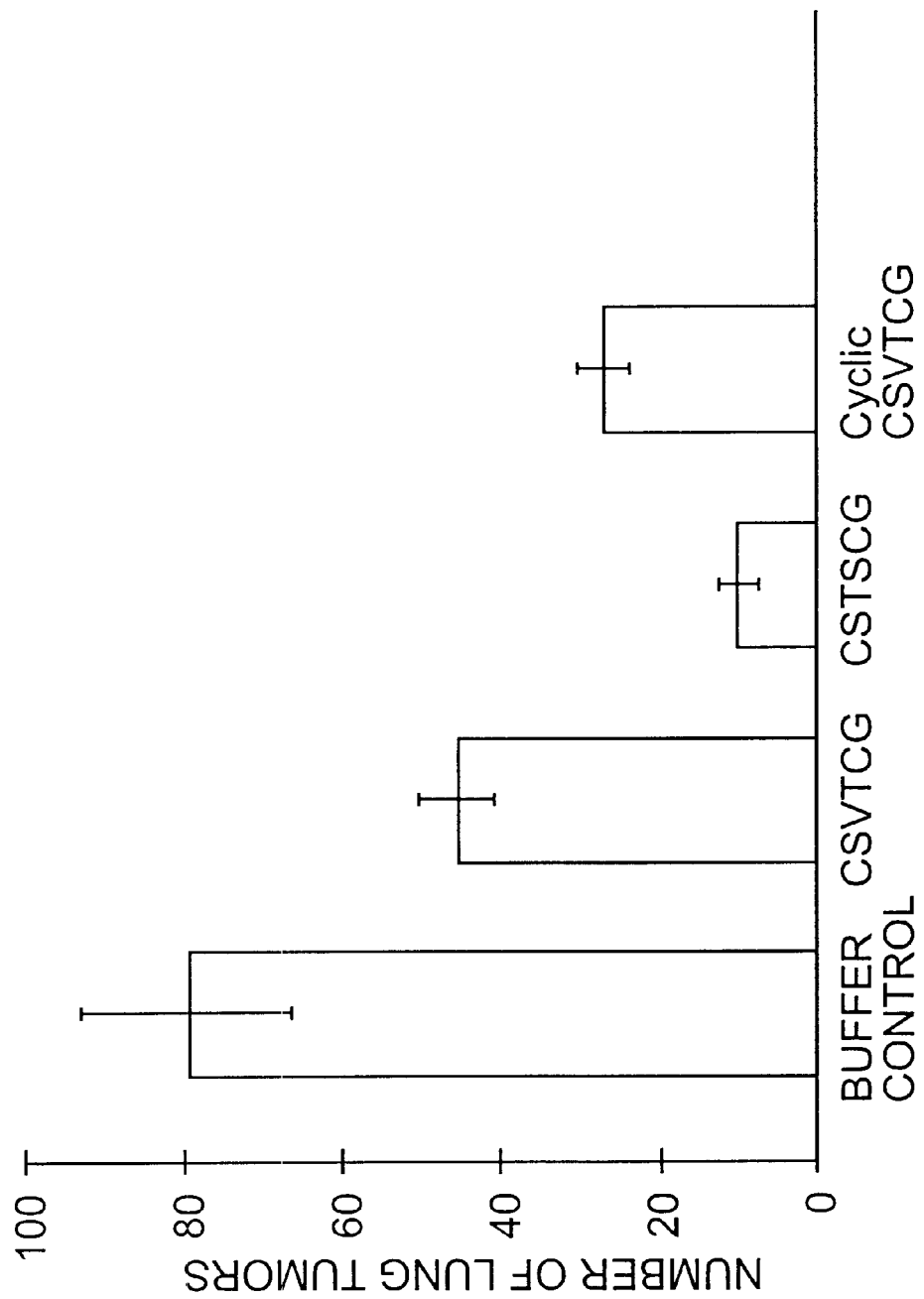
FIG. 6 demonstrates that in vivo the peptides of the invention have antimetastatic activity.
Figure 7:
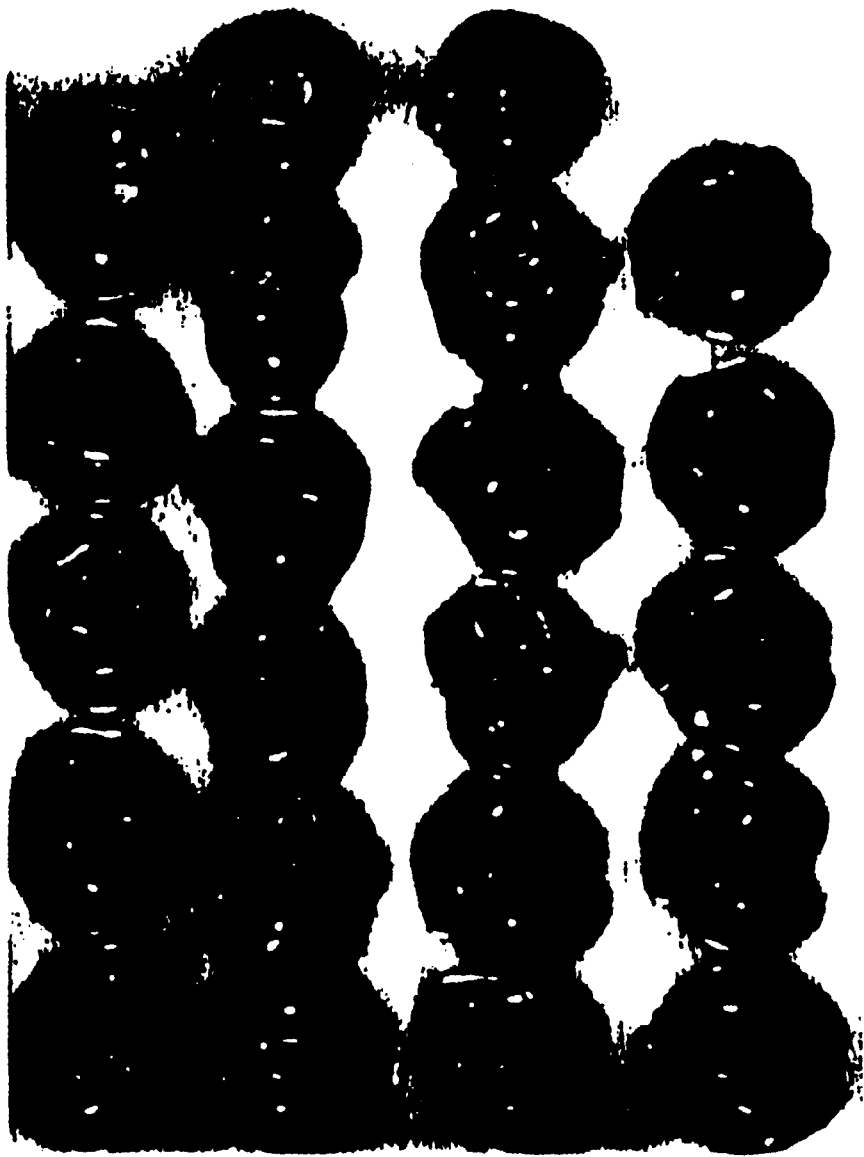
FIG. 7 compares the lungs of mice treated with and without the peptides of the invention in the presence of melanoma cells.

The results shown in FIG. 6 indicate the peptides of the invention have antimetastatic activity. The bar graphs show the mean number of lung tumors observed in the treatment groups and the error bars represent the standard error of the mean FIG. 7 shows representative lungs from each of the treatment groups.

Example 8

Platelet Aggregation Assay

Platelet aggregation was monitored on a single-channel aggregometer equipped to measure luminescence (Chromo-Log, Havertown, Pa.). Platelet-rich-plasma (PRP) was obtained from whole blood anticoagulated with 0.38% sodium citrate by centrifugation at 150×g for 20 minutes.

Figure 8:
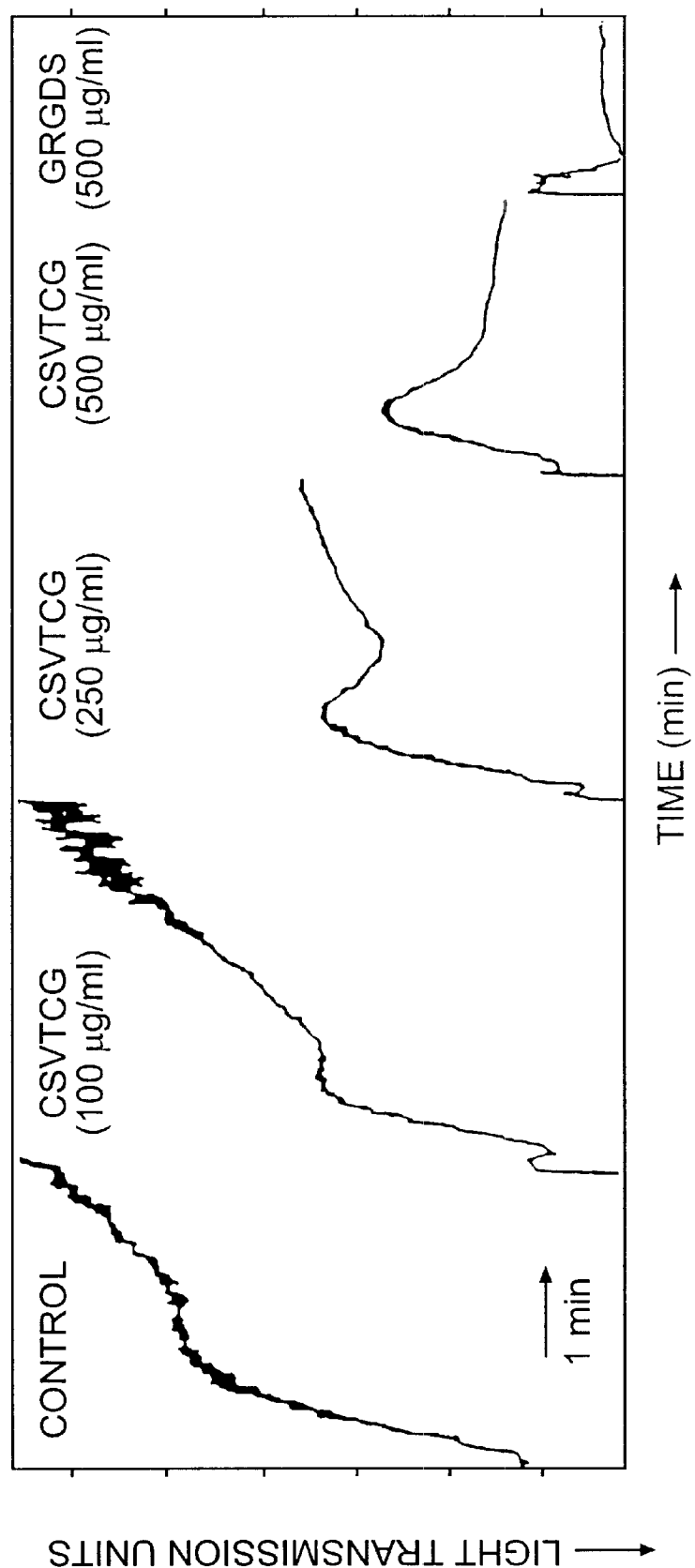
FIG. 8 shows the ability of the peptides of the invention to inhibit ADP-induced platelet aggregation.

The effect of peptides on ADP-induced platelet aggregation is shown in FIG. 8. 0.5 ml aliquots of platelet-rich-plasma were aggregated by stirring with 2 uM ADP in the presence of various concentrations of Cys-Ser-Val-Thr-Cys-Gly (SEQ ID NO: 21) and Gly-Arg-Gly-Asp-Ser (SEQ ID NO: 36). Aggregation was measured at 37° as decrease in optical absorbance vs. time in a chrono-log aggregometer and is shown in FIG. 8. Peptides designated in each panel are represented by their amino acid sequence using the one letter amino acid code.

Figure 22:
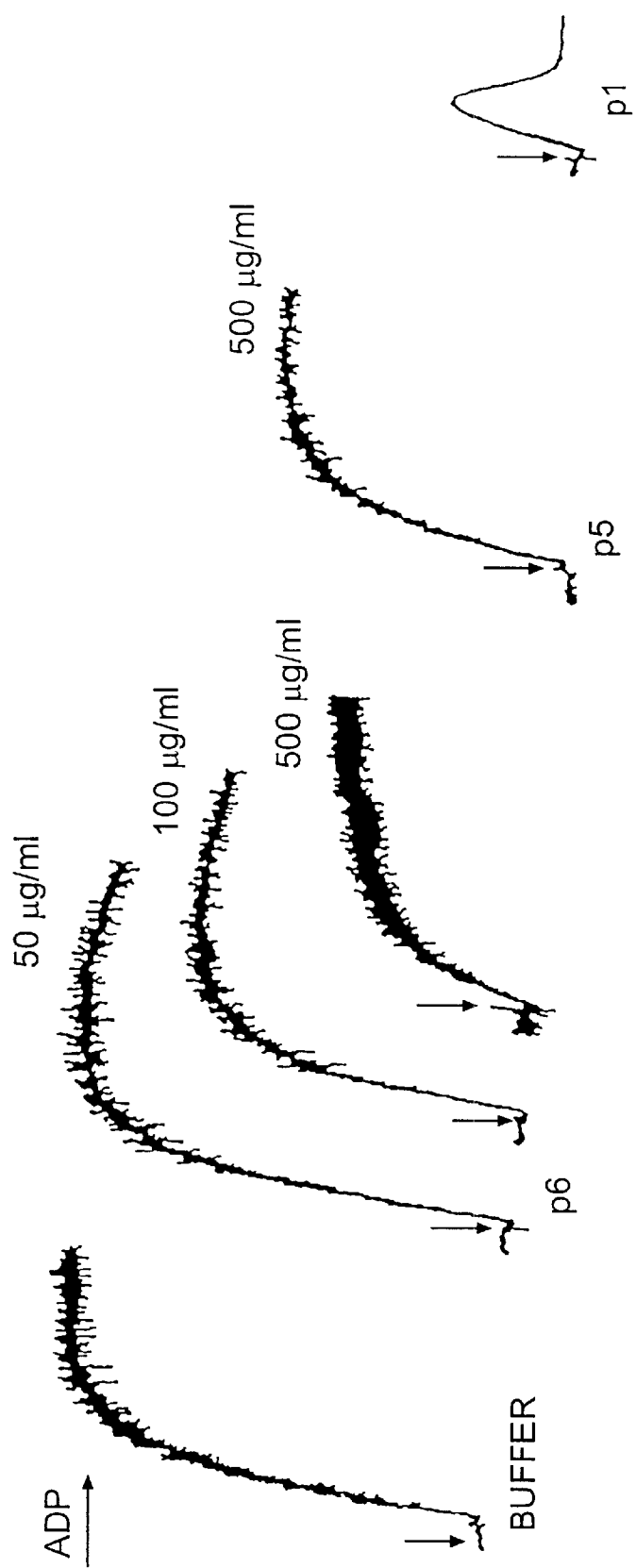
FIG. 22 depicts the in vitro ability of selected peptide compounds of the present invention to inhibit platelet aggregation.

The results shown in FIG. 22 indicate that p1, p5 and p6 inhibit platelet aggregation.

Example 9

The Effect of Peptides on Collagen-Induced Platelet Aggregation

Figure 9:
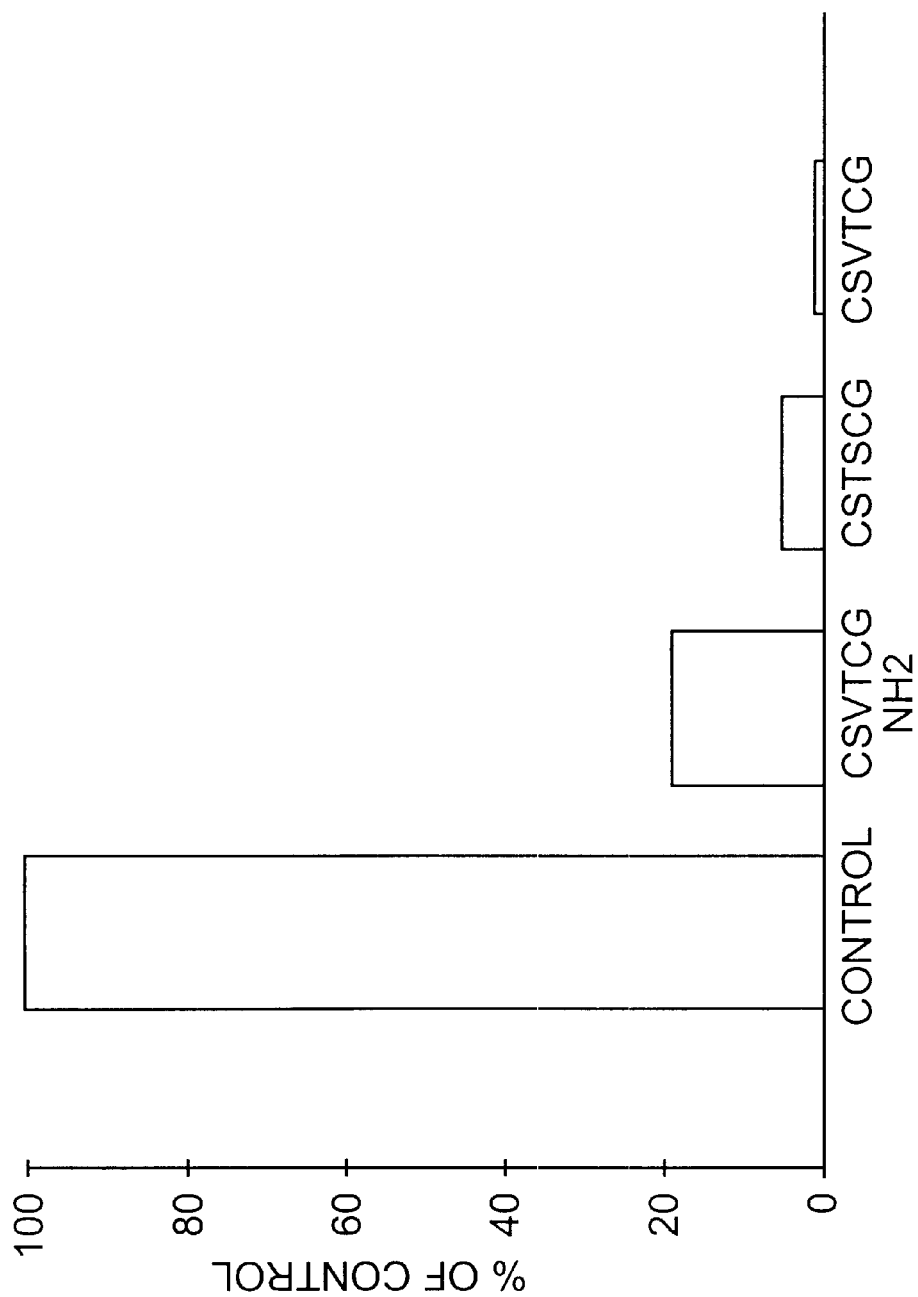
FIG. 9 shows the ability of the peptides of the invention to inhibit collagen-induced platelet aggregation.

Washed human platelets were suspended in HEPES-buffered saline, containing 5 mM glucose and 350 µg/ml BSA. 0.5 ml aliquots of platelets were aggregated by stirring with 5 µg/ml collagen in the presence of 500 µg/ml of various peptides. Aggregation was measured at 37° C. as decrease in optical absorbance vs. time in a Chrono-log aggregometer and is shown in FIG. 9. 100% aggregation was defined as the maximal decrease in absorbance measured in the absence of peptide. % of control was calculated as the decrease in absorbance measured in the presence of peptide divided by the decrease in absorbance measured in the absence of peptide times 100. Peptides are designated under each bar graph by their amino acid sequence represented using the one letter amino acid code.

Example 10

Figure 10:
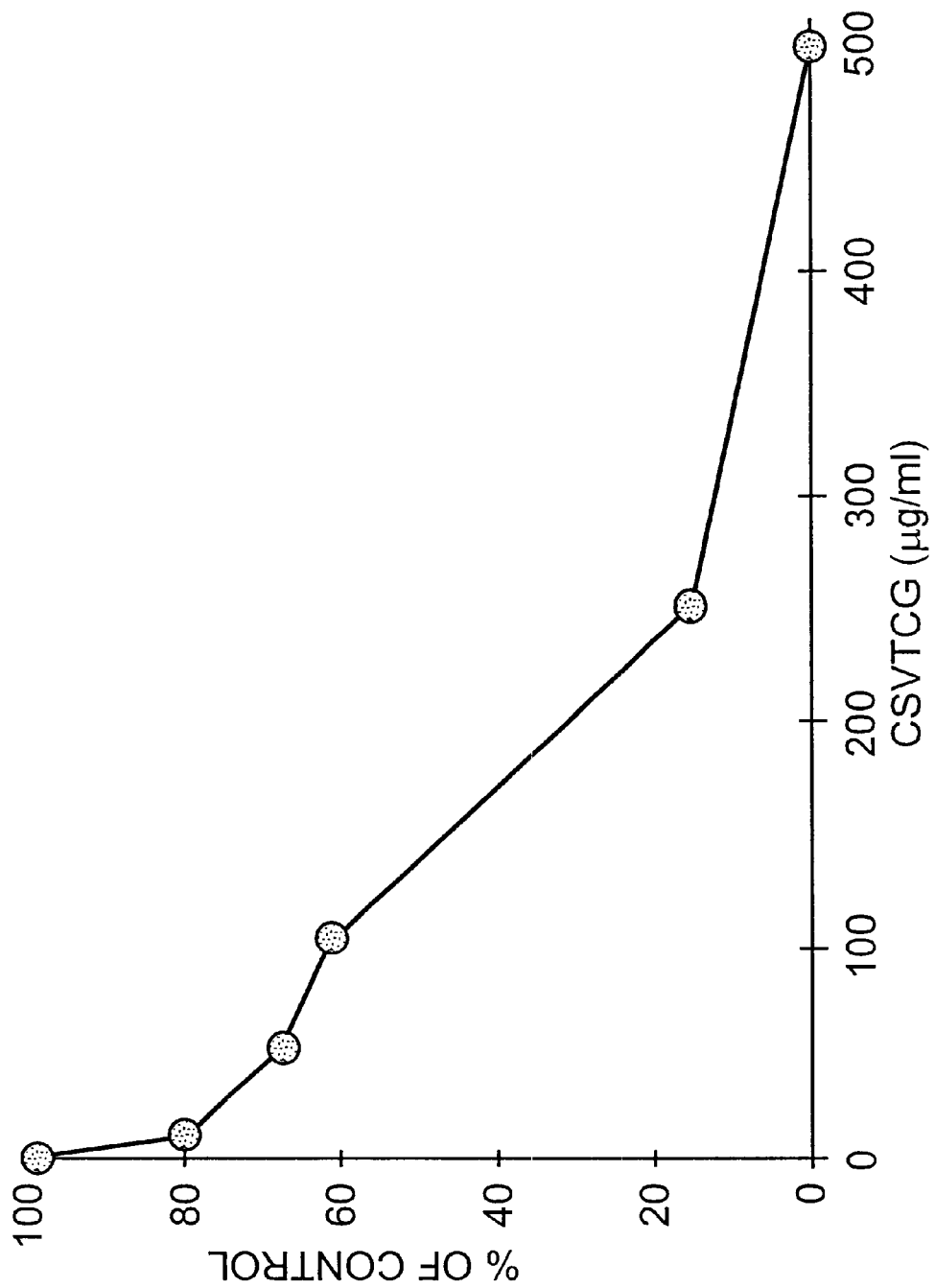
FIG. 10 depicts a dose response of the ability of peptide Cys-Ser-Val-Thr-Cys-Gly (SEQ ID NO: 1) to inhibit collagen-induced platelet aggregation.

Dose-Response of Cys-Ser-Val-Thr-Cys-Gly (SEQ ID NO: 1) on Collagen-Induced Platelet Aggregation Washed human platelets were suspended in HEPES-buffered saline, containing S mM glucose and 350 µg/ml BSA. 0.5 ml aliquots of platelets were aggregated by stirring with 5 μg/ml collagen in the presence of various concentrations of Cys-Ser-Val-Thr-Cys-Gly (SEQ ID NO: 1). Aggregation was measured at 37° C. as decrease in optical absorbance vs. time in a chrono-log aggregometer and is shown in FIG. 10. 100%; aggregation was defined as the maximal decrease in absorbance measured in the absence of peptide. % of control was calculated as the decrease in absorbance measured in the presence of peptide divided by the decrease in absorbance measured in the absence of peptide times 100.

Example 11

Adhesion of Human Platelets to TSP and Peptides

Figure 11:
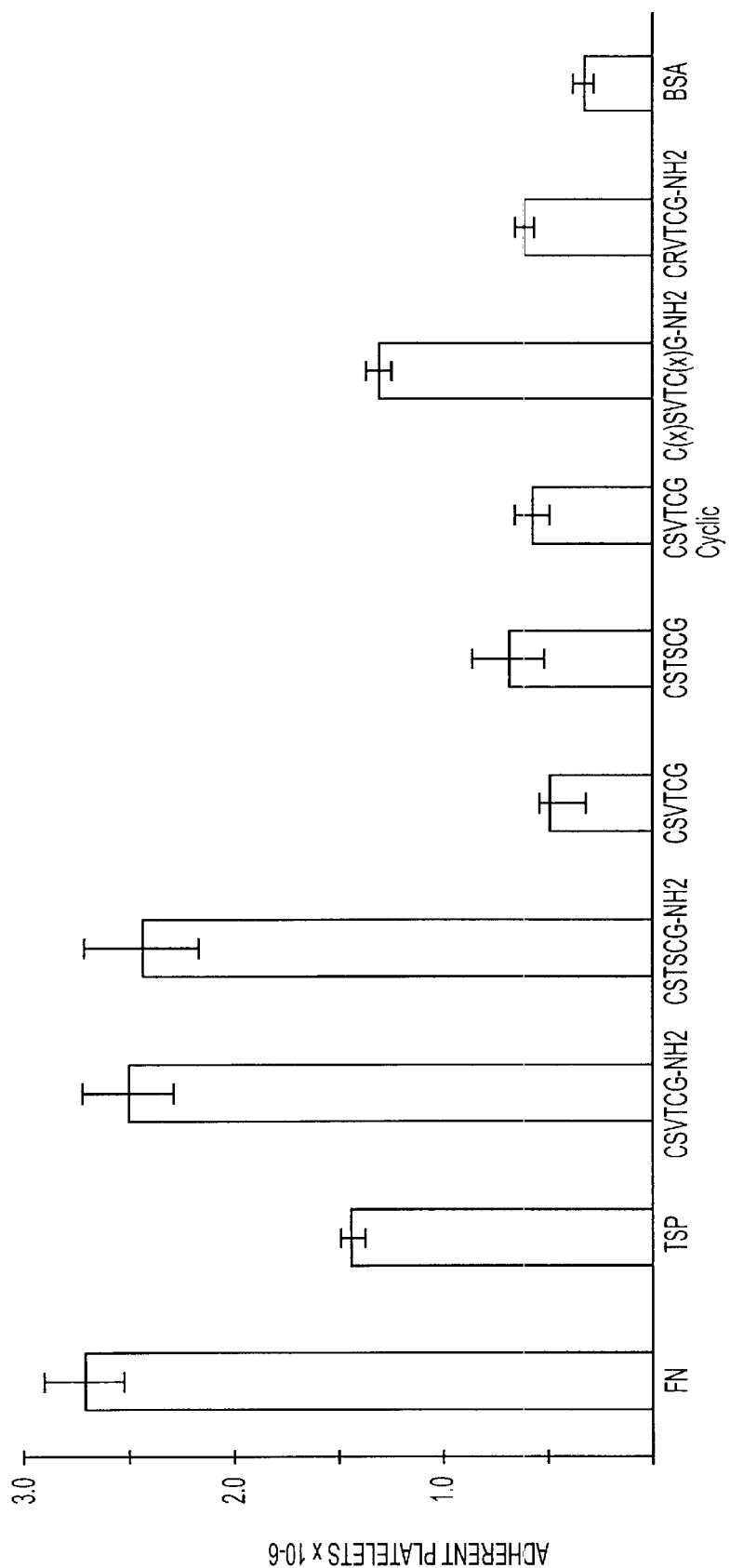
FIG. 11 shows the ability of the peptides of the invention to support the adhesion of human platelets.

The number of adherent platelets was essentially determined as previously described (Tuszynski et al., Anal. Bio., supra). Briefly, 100 μl of 5×10$^8$ platelets/ml washed as previously described (Tuszynski et al., Blood, 72:109–225 (1988)) were added to microtiter plates, the wells of which were treated with 2 μg of peptide or protein solution (HEPES buffered saline, pH 7.4). Solutions were dried at room temperature after incubation in a fume hood overnight. Wells were then washed with HEPES-buffered saline and blocked for 1 hour with 1% fatty acid free bovine serum albumin (BSA) in HEPES buffered saline. Platelets (100 μl) were incubated in the wells for 30 minutes and non-adherent platelets were removed by aspiration. Wells were washed 3× with 200 μl of Hepes buffered saline, pH 7.4. The number of adherent platelets was determined by measuring the platelet-derived protein using the DCA protein assay. The results are shown in FIG. 11. The label under each bar designates the protein or peptide used to coat the well. Proteins used were thrombospondin (TSP), fibronectin (FN), and bovine serum albumin (BSA). Peptides are designated under each bar graph by their amino acid sequence represented using the one letter amino acid code. The peptide having blocked cys residues is given as Cys-(x)-Ser-Val-Thr-Cys-(x)-Gly-NH$_2$ (SEQ ID NO: 6), where x represents the blocking group ACM. A suspension of platelets in Hepes-buffered saline, containing 5 mM glucose and 350 Ag/ml BSA (5×10$^7$ platelets per well) were incubated in each well for 30 minutes, nonadherent platelets removed by aspiration, and adherent cells determined by measurement of cell associated protein as previously described (Tuszynski et al., 184: 189–191(1990)). The data is a representative of 2–3 experiments and data points in each experiment are the mean of three determinations, and the error bars represent the standard error of the mean (SEM).

Example 12

Chemical Synthesis of Trp-Ser-Pro-Cys-Ser-Val-Thr-Cys-Gly (SEQ ID NO: 2) Compound p1

Briefly, 0.13 grams of t-boc-Gly-OCH$_2$ PAM resin (0.79 mmol/g) was subjected to the following sequential addition of suitably protected amino acids: t-boc-Cys(4—CH$_3$Bzl), t-boc-Thr(Bzl), t-boc-Val, t-boc-Ser(Bzl), t-boc-Cys(4-CH$_3$Bzl), t-boc-Pro, t-boc-Ser (Bzl), and t-boc-Trp. Resultant, dry, N-terminal protected peptidyl-resin was suspended in anhydrous hydrogen fluoride containing 5% anisole, 5% dimethyl sulfide, and 1% p-thiocresol for two hours at –5° C. HF and volatile scavengers were removed with nitrogen sparge and the peptide-resin mixture was suspended in cold diethyl ether. The peptide-resin mixture was washed three times with diethyl ether, then the peptide was extracted with 30% acetic acid. This solution was diluted 1:1 with H$_2$O and lyophilized to afford the crude peptide. Purification was achieved on an Amicon C$_{18}$ MC-250-10 column utilizing reverse phase chromatography employing 0.1% aqueous trifluoroacetic acid with gradient generation afforded by the addition of 0.1% TFA in 90% acetonitrile and 10% H$_2$O. Fractions were collected and pooled based on a purity of 90%, as judged by analytical reverse-phase HPLC. Pooled fractions were diluted with deoxygenated H$_2$O and lyophilized to afford the pure peptide as a trifluoroacetic acid salt.

Example 13

Chemical Synthesis of Trp-Ser-Pro-Cys-Ser-Val-Thr-Cys-Gly-NH$_2$ (SEQ ID NO: 2) Compound p6

Briefly, 0.17 g of p-methylbenzyhydrylamine resin (0.62 mmol/g) was subjected to the following sequential addition of suitably protected amino acids-t-boc-Gly, t-boc-Cys(4-CH$_3$ Bzl), t-boc-Thr(Bzl), t-boc-Val, t-boc-Ser(Bzl), t-boc-Cys(4-CH$_3$ Bzl), t-boc-Pro, t-boc-Ser(Bzl), t-boc-Trp (CHO). The resultant n-terminal deprotected, formylated peptidyl-resin was dried then suspended is anhydrous HF containing 8% anisole and 2% dimethyl sulfide. Treatment was for 0.5 hours at –20° C. and 2 hours at 0° C. The HF was removed with nitrogen sparge. The peptide-resin mixture was suspended in and washed 3 times with diethyl ether. The peptide was extracted with 25% acetic acid. The resin was washed with 50% acetic acid and with H$_2$O. The aqueous solutions were pooled, diluted 1:1 with deoxygenated H$_2$O and lyophilized to afford the formylated crude peptide. Deformylation was effected using the procedure described in Applied Biosystems 430A User Bulletin 18. (Apr. 28, 1987). The peptide (5mg/ml concentrate) in 6M guanidine-HCl was cooled to 0° C. and ethanolamine added to 1 M. The pH is lowered to 6 with concentrated hydrochloric acid.

Purification was on an Amicon C$_{18}$ MC-250-10 column using reserve-phase chromatography. The ratio of acetonitrile to H$_2$O was increased maintaining 0.1% TFA to achieve gradient elution. Collected fractions with a purity of 90%, as determined by analytical reverse-phase PHLC, were pooled, diluted with deoxygenated H$_2$O and lyophilized to afford pure peptide as a trifluoroacetic acid salt.

Example 14

Chemical Synthesis of fTrp-Ser-Pro-Cys-Ser-Val-Thr-Cys-Gly-NH2 (SEQ ID NO: 2) Compound p5

Briefly, procedure was same as for Example 13 except the deformylation step is not performed. The afforded crude peptide obtained past HF cleavage and subsequent lyophilization was purified as the formylated, C-terminal amide species.

Example 15

Other Thrombospondin Fragments or Analogs

Following the procedures outlined in Examples 12, 13, and 14 with appropriate modification, the following thrombospondin fragments or analogs were synthesized:

| Compound | Structure | |
|---|---|---|
| p18 | Trp-Asp-Ile-Cys-Ser-Val-Thr-Cys-Gly | (SEQ ID NO:10) |
| P19 | Trp-Ser-Ser-Cys-Ser-Val-Thr-Cys-Gly | (SEQ ID NO:11) |
| p20 | Trp-Thr-Ser-Cys-Ser-Thr-Ser-Cys-Gly | (SEQ ID NO:12) |
| P11 | Trp-Ser-Pro-Trp-Ser-Trp-Thr-Ser-Cys-Ser-Thr-Ser-Cys-Gly-Asn-Gly-Ile-Gln-Gln-Arg-Gly-Arg | (SEQ ID NO:13) |
| p17 | Trp-Ser-His-Trp-Ser-Pro-Trp-Ser-Ser-Cys-Ser-Val-Thr-Cys-Gly-Asp-Gly-Val-Ile-Thr-Arg-Ile-Arg | (SEQ ID NO:14) |
| p12 | Trp-Gly-Pro-Trp-Ser-Pro-Trp-Asp-Ile-Cys-Ser-Val-Thr-Cys-Gly-Gly-Gly-Val-Gln-Lys-Arg-Ser-Arg | (SEQ ID NO:15) |
|  | Trp-Ser-Pro-Cys-Ser-Val-Thr-Cys-Ser | (SEQ ID NO:16) |
|  | Trp-Ser-Gln-Cys-Ser-Val-Thr-Cys-Gly | (SEQ ID NO:17) |
|  | Trp-Ser-Gln-Cys-Asn-Val-Thr-Cys-Gly | (SEQ ID NO:18) |
|  | Trp-Thr-Pro-Cys-Ser-Val-Thr-Cys-Gly | (SEQ ID NO:19) |
| p4 | Asp-Gly-Gly-Trp-Ser-His-Trp-Ser-Pro-Trp-Ser-Ser-Cys-Val-Thr-Cys-Gly-Asp-Gly-Val-Ile-Thr-Arg-Ile-Arg-Leu-Cys-Asn-Ser-Pro-Ser-Pro-Gln-Met-Asn-Gly-Lys-Pro-Cys-Glu-Gly-Glu-Ala-Arg-Glu-Thr-Lys-Ala-Cys-Lys-Lys-Asp-Ala-Cys-Pro-Ile-Asn-Gly-Gly | (SEQ ID NO:20) |

Example 16

Direct Adhesion Assay

It is believed that thrombospondin acts in metastasis through its adhesive properties. An assay was developed, generally in accordance with the disclosure of Tuszynski et al., *Anal. Bio.*, 184:189–91 (1990), which evaluates the ability of melanoma cells to adhere to the thrombospondin fragments or analogs of the invention. In this assay, wells of a 96-well microtiter dish (Costar, Cambridge, Mass.) were incubated for two to three hours with 50 P1 of a 40 vg/ml solution of various ligands in 20 mM NaCl, pH 7.3. Thrombospondin (purified by the method of Tuszynski et al., *J. Biol. Chem.*, 260:12240–5 (1985), fibronectin (Sigma Chemical Co., Missouri) served as the positive control. Bovine serum albumin (BSA) (Sigma Chemical Co.) served as the negative control. Thrombospondin analogs of the invention p1, p5 and p6 were synthesized as described in Examples 1 through 3. Following peptide adhesion to the microtiter dish, the wells were aspirated, treated with 200 µl phosphate buffered saline (PBS) containing 1% BSA for 1 hour and then washed three more times with 200 µl PBS.

Mouse $B_{16}F_{10}$ melanoma cells were grown and harvested during log phase of growth using standard procedures. The harvested cells were washed two times in serum-free Dulbecco's minimum essential medium (DMEM) (Flow Laboratories) and suspended in DMEM at a final concentration of $4\times10^5$ cells/ml. Of the cell suspension 100 µl was added to each well of the microtiter dish containing the various ligands and the dish incubated at 37° C. in a $CO_2$ incubator for 1 hour. Nonadherent cells were removed by aspiration and the wells washed three times with 200 µl of PBS. The total cell-associated protein was determined by dissolving the attached cells directly in the microtiter wells with 200 µl of the Pierce BCA working solution (Pierce Chem. Co. Booklet No. 23225 (1987)). The plate was covered with an adhesive mylar sheet (Flow Labs) and incubated at 60° C. for 30 minutes. Plates were allowed to cool to room temperature, cover sheets were removed, and the absorbance of each well was determined at 562 nm with a microtiter plate reader (Biotek, Burlington, Vt.)

The results shown in Table II indicate that the peptides of the inventions p1, p5, and p6 display adhesive properties.

TABLE II

| Absorbed Compound (2 µg) | Adhesion as % Thrombospondin |
|---|---|
| Thrombospondin | 100 |
| p1 | 98 |
| P5 | 79 |
| p6 | 70 |
| BSA | 13 |

Example 17

Competitive Assay to Measure Thrombospondin Specific Adhesion to Melanoma Cells The direct adhesion assay of Example 16 was modified to measure the ability of the peptide compounds of the invention to compete with intact thrombospondin for adhesion to melanoma cells.

In this assay, intact thrombospondin is absorbed onto microtiter dishes as described in Example 16. The assay is similar to Example 16 except that before the melanoma cells are added to the microtiter dishes they are preincubated for 15 minutes with 100 µg/ml of various ligands.

The results shown in Table III indicate that peptide p1 is able to effectively compete with thrombospondin for adhesion of melanoma cells. Peptides p5 and p6 compete to a lesser degree at this concentration.

TABLE III

| Compound | Concentration (µg/ml) | % of Buffer Control |
|---|---|---|
| buffer | — | 100 |
| p1 | 100 | 20 |
|  | 100 | 42 |
|  | 50 | 40 |
|  | 10 | 49 |
| p5 | 100 | 62 |
|  | 100 | 108 |
|  | 50 | 104 |
|  | 10 | 99 |
|  | 100 | 83 |
|  | 200 | 89 |
|  | 300 | 83 |
| p6 | 100 | 89 |
|  | 200 | 74 |
|  | 300 | 74 |

Example 18

Direct Platelet Adhesion Assay

The number of adherent platelets was essentially determined as previously described (Tuszynski et al., *Anal. Bio.*, supra). Briefly, 100 µl of $5 \times 10^8$ platelets/ml washed as previously described (Tuszynski, et al., *Blood,* 72:109–225 (1988)) were added to microtiter plates, the wells of which were treated with 50 µl of a 40 µg/ml peptide or protein solution (Hepes buffered saline, pH 7.4). Solutions were dried at room temperature after incubation in a fume hood for two hours. Wells were blocked for one hour with 1% BSA. Platelets (100 µl) were incubated in the wells for 30 minutes and non-adherent platelets were removed by aspiration. Wells were washed 3× with 200 µl of Hepes buffered saline, pH 7.4. The number of adherent platelets was determined by measuring the platelet-derived protein using the BCA protein assay.

The results shown in Table IV indicate that at this concentration p1, p6, and to a lesser degree, p5 adhere to platelets.

TABLE IV

| Compound | Adherence as % Control |
|---|---|
| Thrombospondin | 100 |
| BSA | 0.7 |
| P1 | 39 |
| p5 | 2.1 |
| p6 | 38 |
| fibronectin | 83 |

Example 19

Competitive Assay to Measure Thrombospondin Specific Adhesion to Platelets

The direct adhesion assay of Example 18 was modified to measure the ability of the peptide compounds of the invention to compete with intact thrombospindin or fibronectin for adhesion of platelets.

In this assay, thrombospondin (TSP) or fibronectin (FN) was absorbed onto microtiter dish as described in Example 18. The assay was similar to Example 18 except that before platelets were added to the microtiter dishes they were preincubated with 250 µg/ml of various ligands.

The results shown in Table V indicate that peptide p1 effectively competed with thrombospondin for platelet adhesion, but did not compete with fibronectin.

TABLE V

| Compound | Concentration (µg/ml) | Absorbed Protein | % Buffer Control |
|---|---|---|---|
| buffer | — | TSP | 100 |
| p1 | 250 | TSP | 71 |
| p5 | 250 | TSP | 107 |
| p6 | 250 | TSP | 98 |
| buffer | — | FN | 100 |
| p1 | 250 | FN | 108 |
| p5 | 250 | FN | 109 |
| p6 | 250 | FN | 96 |

Example 20

Antimetastatic Activity In Vivo

The in vivo model used to demonstrate the antimetastatic activity of the peptide compounds of the invention is described by Tuszynski et al. (*Cancer Res.* 47:4130–4133 (1987). Briefly, C57 black mice were intravenously injected with $5 \times 10^5$ $B_{16}$ $F_{10}$ mouse melanoma cells in the presence of either control buffer (Hepes buffered saline, pH 7.4), or the indicated amount of peptide compound of the invention p1, p5 or p6. After 16 days, the mice were sacrificed and the number of lung tumors counted.

The results shown in Table VI indicate the peptides of the invention have antimetastatic activity. The p1-, p5- and p6-treated animals developed statistically fewer tumors than controls. Additionally, the lung tumors were smaller in size in the p1- and p6-treated animals.

TABLE VI

| Compound | Concentration µg/mouse | % buffer control |
|---|---|---|
| buffer | — | 100 |
| p1 | 30 | 49 |
| p5 | 30 | 87 |
| p6 | 30 | 91 |
| p6 | 100 | 102 |
| p6 | 300 | 50 |

Example 21

Effect of Synthetic Peptides on Melanoma Tumor Cell Metastasis

To demonstrate the effect of the peptides of the present invention on tumor cell metastasis, 1 mg of peptide was injected into one lateral tail vein of mice, followed immediately by injection of mouse B16-F10 melanoma cells (100,000) into the second lateral tail vein. Mice were sacrificed two weeks later and lung tumors counted. Treatment groups consisted of five animals. The photograph of FIG. 12 depicts three lungs from each treatment group. The black spots are melanoma tumors. All metastasis experiments were repeated 2–3 times showing qualitatively similar results depicted in the bar graph of FIG. 12. The peptide Cys-Ser-Val-Thr-Cys-Gly (SEQ ID NO: 1), cyclic Cys-Ser-Val-Thr-Cys-Gly (SEQ ID NO: 1), a peptide in which one cysteine residue was disulfide linked to the other, and Cys-Ser-Thr-Ser-Cys-Gly (SEQ ID NO: 9), a related sequence found in TSP-1, significantly blocked mouse B16-F10 melanoma cell metastasis when injected intravenously shortly before or after tumor implantation (FIG. 12 and Tuszynski, G. et al., *J. Cell Biol.,* 116: 209–217 (1992)).

Example 22

Figure 13A:
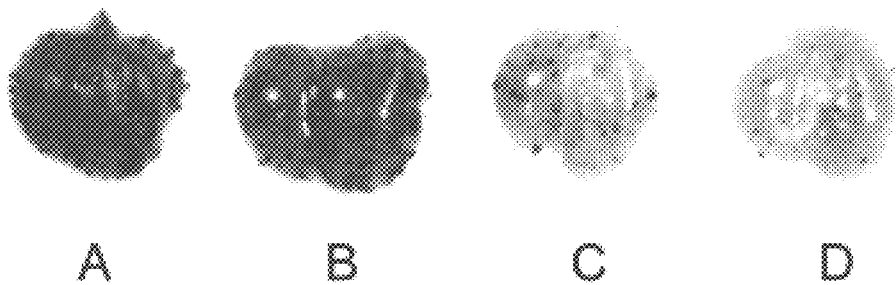
FIGS. 13A and 13B depict the effect of intravenous and intraperitoneal administration of Cys-(Acm)-Ser-Val-Thr-Cys-(Acm)-Gly (SEQ ID NO: 6) on melanoma lung metastasis. Acm represents the sulfhydral blocking group —CH$_2$—NH—COCH$_3$.
Figure 13B:
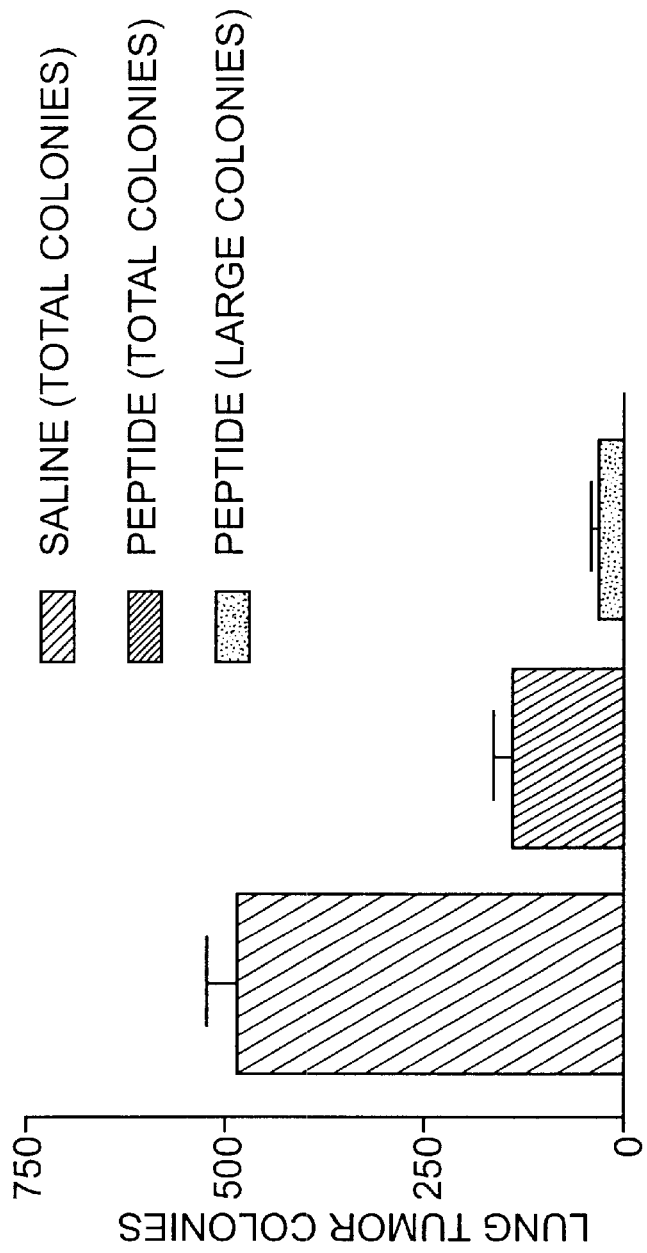

Effect of Intravenous and Intraperitoneal Administration of Cys-(Acm)-Ser-Val-Thr-Cys-(Acm)-Gly (SEQ ID NO: 6) on Melanoma Lung Metastasis One bolus injection of Cys-(Acm)-Ser-Val-Thr-Cys-(Acm)-Gly (SEQ ID NO: 6) peptide (1 mg/mouse intravenously or 5 mg/mouse intraperitoneally ) was administered followed by intravenous injection of mouse B16-F10 melanoma cells (100,000). Each treatment group consisted of 5 animals. After 10 days animals were sacrificed and lung tumors counted. FIG. 13A shows representative lungs from peptide-treated and control animals. FIG. 13B shows the number of lung colonies in control and peptide animals treated with an intraperitoneal injection of 5 mg peptide. Error bars represent the standard error of the mean. P values between control and peptide-treated groups <0.001.

The blocked Cys-Ser-Val-Thr-Cys-Gly (SEQ ID NO: 1), i.e., Cys-(Acm)-Ser-Val-Thr-Cys-(Acm)-Gly (SEQ ID NO: 6), is more stable toward oxidation. Both the Cys-Ser-Val-Thr-Cys-Gly (SEQ ID NO: 1) peptide and the blocked analogue have identical blocking activity in metastasis and the other assays described below.

We found that the blocked Cys-Ser-Val-Thr-Cys-Gly (SEQ ID NO: 1) peptide effectively blocked melanoma lung colonization. The peptide treated animals developed 80 % fewer lung metastasis as compared to saline or scrambled peptide controls (Val-Cys-(Acm)-Thr-Gly-Ser-Cys-(Acm)-Gly (SEQ ID NO: 37)). Remarkably, the peptide treated animals developed few large lung metastases, suggesting the compound may not be inhibiting the implantation of tumor but also the development.

Example 23

Effect of Intraperitoneal Administration of Cys-(Acm)-Ser-Val-Thr-Cys-(Acm)-Gly (SEQ ID NO: 6) on Melanoma Lung Metastasis Mice were intravenously injected with mouse B16-F10 melanoma cells (75,000). After 3 days, each mouse was treated daily by intraperitoneal injection with either PBS, 0.01 mg, or 1 mg of peptide for 10 days. Treatment groups consisted of 5 mice. After 10 days animals were sacrificed and lung tumors counted. Error bars represent the standard error of the mean. p<0.001 between control- and peptide-treated groups.

As shown in FIG. 14, melanoma colonies were markedly suppressed by more than 80% in the 1 mg/ml treated animals. Even the 0.01 mg/ml-treated animals showed a satistically significant 27 % reduction in lung colonies with respect to buffer-treated. These results indicate that the Cys-(Acm)-Ser-Val-Thr-Cys-(Acm)-Gly (SEQ ID NO: 6) peptide, in addition to being able to inhibit tumor implantation, can also inhibit tumor progression of three day old lung tumors.

Example 24

To further evaluate the anti-metastatic properties of the Cys-Ser-Val-Thr-Cys-Gly (SEQ ID NO: 1) peptide, we measured the effect of peptide and antibody against the Cys-Ser-Val-Thr-Cys-Gly (SEQ ID NO: 1) receptor in an athymic model of human tumor progression. In this model, human MDA-MB-231 breast carcinoma cells were injected intraperitoneally in athymic mice. Animals were then treated with either peptide or receptor IgG for three weeks after which the extent of lung and liver metastasis is determined.

For the peptide experiments, eighteen mice were inoculated with MDA-MB-231 human breast cancer cells. After 72 hours, mice were randomized to treatment with every-other-day intraperitoneal injections of saline, scrambled peptide, or a Cys-Ser-Val-Thr-Cys-Gly (SEQ ID NO: 1) peptide for 20 days. One mouse treated with the Cys-Ser-Val-Thr-Cys-Gly (SEQ ID NO: 1) peptide expired after traumatic injection. Mice were sacrificed at 21 days. The peritoneal cavity was examined grossly for primary tumor implantation. The liver and lungs were examined histologically for micrometastases. Statistical analysis was performed by Chi-square analysis.

For the antibody experiments, eighteen mice were inoculated intraperitoneally with $5 \times 10^6$ exponentially growing MDA-MB-231 cells. Mice were then randomized to treatment with saline, control antibody, or a polyclonal anti-TSP receptor antibody. Treatment began one day after intraperitoneal inoculation with tumor cells. Mice were given an intraperitoneal injection every other day for 20 days with the control antibody or anti-TSP-1 receptor antibody or HBSS alone in 0.2 ml volume. Mice were sacrificed at 21 days. The peritoneal cavity was examined grossly for evidence of primary tumor implantation. Liver and lungs were examined histologically for micrometastases. Statistical analysis was performed by Chi-square analysis. The Cys-Ser-Val-Thr-Cys-Gly (SEQ ID NO: 1) peptide inhibited in vivo breast cancer progression. All of the mice exhibited evidence of intraperitoneal seeding of tumor. The mice treated with the Cys-Ser-Vla-Thr-Cys-Gly (SEQ ID NO: 1) peptide, however, exhibited fewer and smaller intraperitoneal tumors. Treatment with the Cys-Ser-Val-Thr-Cys-Gly (SEQ ID NO: 1) peptide significantly decreased metastases in the two organs examined when compared with the saline or scrambled peptide treatment groups (see Table VII below).

TABLE VII

| Treatment | Liver | Lungs |
| --- | --- | --- |
| Saline alone | 6/6 | 3/6 |
| Scrambled peptide | 5/6 | 4/6 |
| Cys-Ser-Val-Thr-Cys-Gly (SEQ ID NO:1) | 1/5* | 0/5 |

Numbers represent the no. of animals with metastases/total no. of animals in each group. * $p<0.01$, †$p=0.07$.

The Cys-Ser-Val-Thr-Cys-Gly (SEQ ID NO: 1)-specific TSP-1 receptor antibody totally prevented intraperitoneal tumor development as well as subsequent metastasis formation. The results are summarized in Table VIII below.

TABLE VIII

| Treatment | Peritoneal Tumor | Liver | Lungs |
| --- | --- | --- | --- |
| Saline | 6/6 | 4/6 | 3/6 |
| Control IgG | 6/6 | 5/6 | 3/6 |
| Anti-Receptor IgG | 1/6* | 0/6* | 0/6 |

Numbers represent the no. of animals with metastases/total no. of animals in each group. * $p<0.01$. These data show that Cys-Ser-Val-Thr-Cys-Gly (SEQ ID NO: 1) peptide and TSP-1 through its Cys-Ser-Val-Thr-Cys-Gly (SEQ ID NO: 1)-specific receptor mediate breast tumor progression and metastasis.

Example 25

Figure 15:
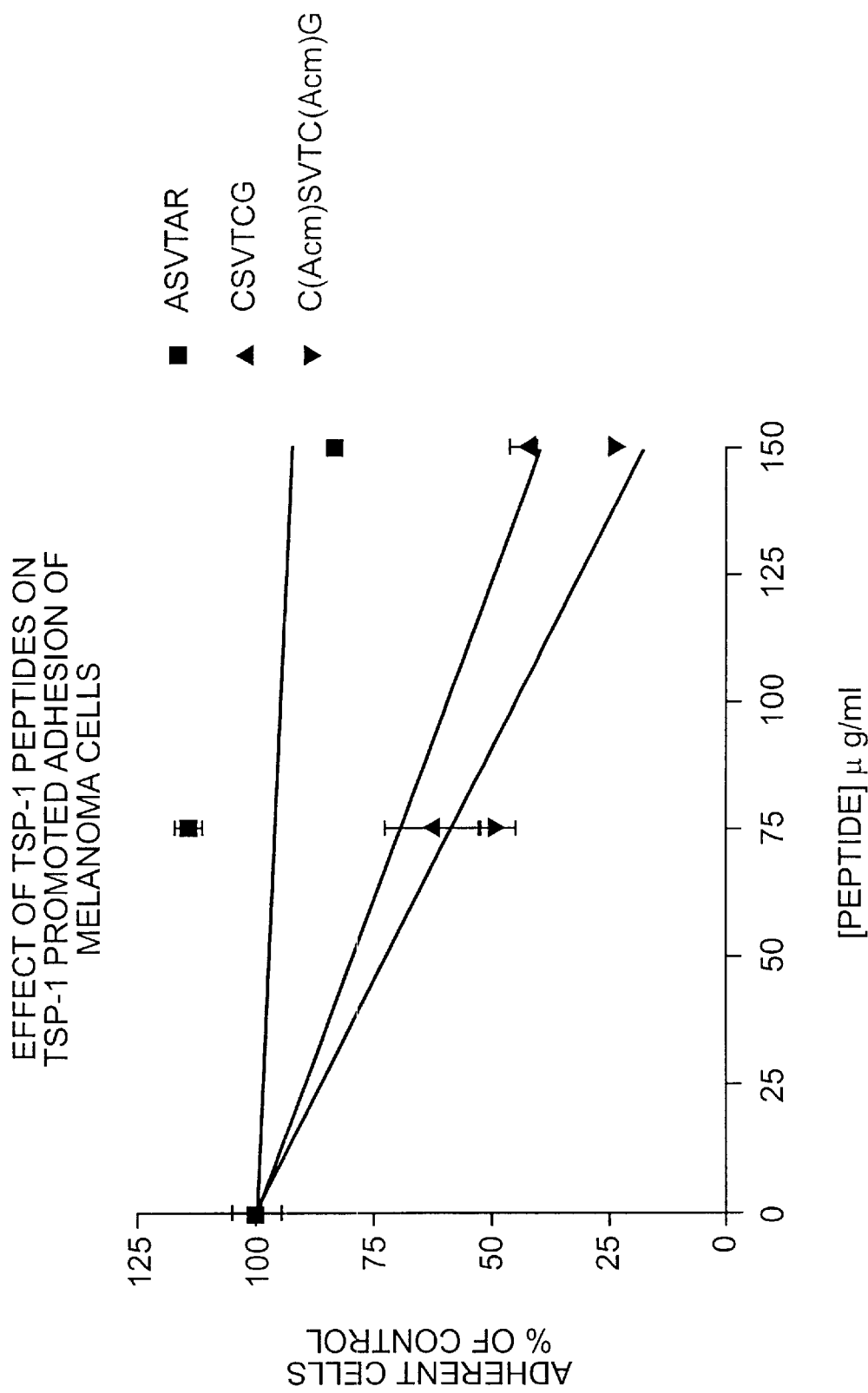
FIG. 15 depicts the effect of TSP-1 peptides on TSP-1 mediated adhesion of melanoma cells.

Effect of TSP-1 Peptides on TSP-1 Mediated Adhesion of Melanoma Cells 50,000 melanoma cells per well of a microtiter plate coated with 2 mg/well of TSP were plated in the presence and absence of peptide. Cells were incubated for 30 minutes and non-adherent cells were removed by aspiration and washing with PBS. Adherent cells were counted in 5 representative high power fields. The results are depicted in FIG. 15. Error bars represent the standard error of the mean. p<0.001 between control and peptide-treated groups.

Example 26

Effect of TSP-1 Peptides on TSP-1 Mediated Invasion of Melanoma Cells

Figure 16:
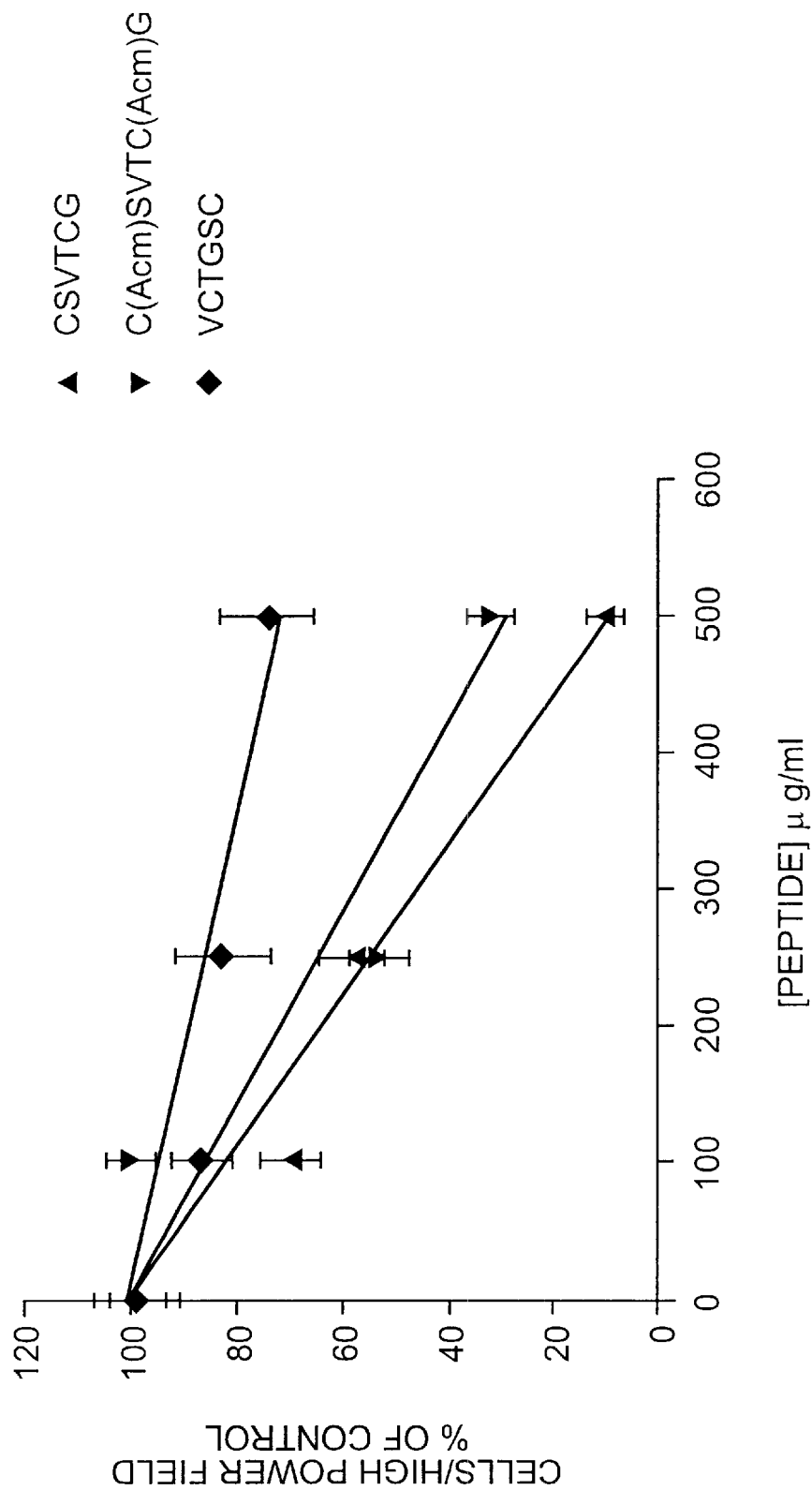
FIG. 16 shows the effect of TSP-1 peptides on TSP-1 mediated invasion of melanoma cells.

We have previously shown that TSP-1 in a dose-dependent manner promotes breast and oral squamous and breast carcinoma invasion of collagen. T. Wang et al., *J. Surgical Res.*, 63: 39–43 (1996). Similarly TSP-1 promotes the dose-dependent collagen invasion of melanoma cells. In this experiment we evaluated the effect of various concentrations of TSP-1 peptide on invasion promoted by 20 μg/ml of TSP-1 placed in the bottom chamber of a Boyden apparatus. 50,000 cells were plated in serum-free medium in the presence of various concentrations of peptide placed in the top chamber of the Boyden apparatus. After 6 hours, cells traversing the collagen-coated membrane were counted in 5 representative high power fields as previously described by Wang et al., *J. Surgical Res.*, 63: 39–43 (1969). The results are presented in FIG. 16. Error bars represent the standard error of the mean. p<0.001 between control and peptide-treated groups.

Example 27

Effect of TSP-1 Peptides on TSP-1-stimulated Endothelial MMP-9 Production

Previous data suggested that TSP-1 mediates angiogenesis through the up-regulation of MMP-9, we hypothesized that these angiogenesis inhibiting peptides could also modulate endothelial MMP-9 production. To test this hypothesis, we evaluated the effect of these peptides, as well as other molecules, such as heparin and Arg-Gly-Asp peptides, which have also been shown to mediate TSP-1 cell interactions, on TSP-1-stimulated endothelial MMP-9 production (Table IX). We found that Cys-Ser-Val-Thr-Cys-Gly (SEQ ID NO: 1) peptide and heparin at high doses inhibited MMP-9 production by 86% and 50%, respectively, whereas an irrelevant peptide, Ala-Ser-Thr-Ala-Arg (SEQ ID NO. 38), and,Arg-Gly-Asp had no effects. These results suggest that the Cys-Ser-Val-Thr-Cys-Gly (SEQ ID NO: 1) domain as well as heparin binding domains of TSP-1 may mediate MMP-9 production by endothelial cells.

The data in Table IX shows the effect of various treatments on TSP-1 promoted MMP-9 production in BAE cells. BAE cells were treated with TSP-1 as described in Example 27. MMP-9 levels were quantitated from densitometry of the zymograms prepared from the BAE cell conditioned media. The control was 15 μg/ml TSP-1. All other treatments were performed in the presence of 15 μg/ml TSP-1.

TABLE IX

| Treatment | Concentration | Relative MMP-9 Levels | % inhibition |
|---|---|---|---|
| Control | — | 1.0 | 0 |
| Cys-Ser-Val-Thr-Cys-Gly (SEQ ID NO:1) | 0.20 mM | 0.14 | 86 |

TABLE IX-continued

| Treatment | Concentration | Relative MMP-9 Levels | % inhibition |
|---|---|---|---|
| Ala-Ser-Val-Thr-Ala-Arg (SEQ ID NO:39) | 0.20 mM | 0.78 | 12 |
| Arg-Gly-Asp | 0.50 mM | 1.03 | 0 |
| Heparin | 50 μg/ml | 0.94 | 6 |
| Heparin | 500 μg/ml | 0.45 | 55 |
| Heparin | 1000 μg/ml | 0.50 | 50 |

Example 28

Figure 17A:
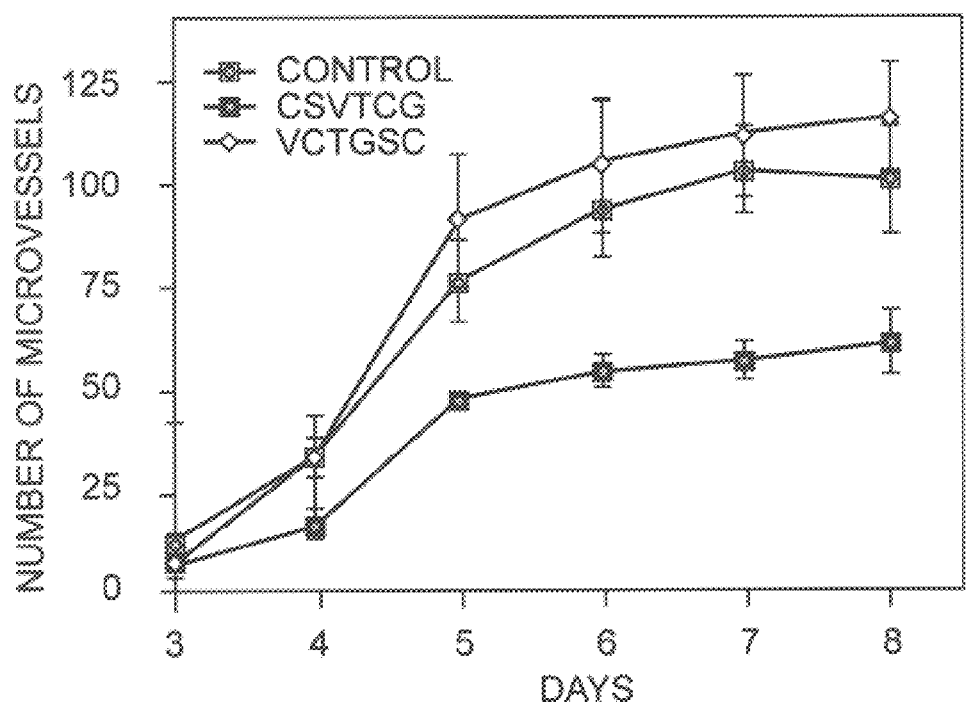
FIGS. 17A and 17B depict the effect of peptide Cys-Ser-Val-Thr-Cys-Gly (SEQ ID NO: 1) and its scrambled Val-Cys-Thr-Gly-Ser-Cys (SEQ ID NO: 7) control on angiogenesis in serum-free collagen gel culture of rat aorta.
Figure 17B:
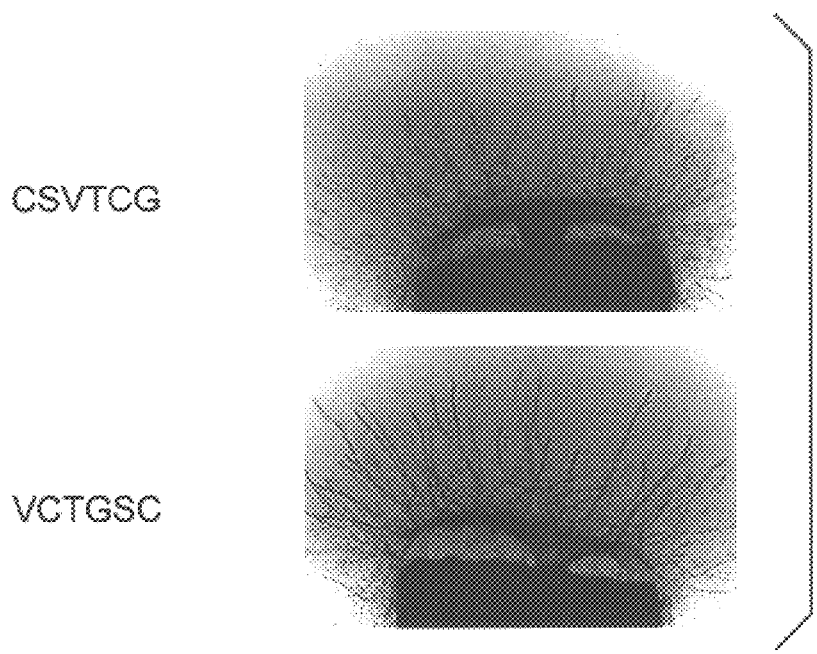

Effect of Cys-Ser-Val-Thr-Cys-Gly (SEQ ID NO: 1) Peptide and its Scrambled Val-Cys-Thr-Gly-Ser-Cys (SEQ ID NO: 7) Control on Angiogenesis In serum-free collagen gel culture of rat aorta, the Cys-Ser-Val-Thr-Cys-Gly (SEQ ID NO: 1) peptide significantly (p=0.0003, N=6) inhibited angiogenesis as compared to the untreated control or the control treated with the scrambled peptide. Error bars=SEM. Photo-micrograph (4× magnification) of a representative aortic ring culture treated either with Cys-Ser-Val-Thr-Cys-Gly (SEQ ID NO: 1) or Val-Cys-Thr-Gly-Ser-Cys (SEQ ID NO: 7) (FIG. 17B). The Cys-Ser-Val-Thr-Cys-Gly (SEQ ID NO: 1)-treated culture has fewer capillary outgrowths than the Val-Cys-Thr-Gly-Ser-Cys (SEQ ID NO: 7) scrambled peptide control.

Example 29

Effect of TSP-1 Derived Peptides on TSP-1 Mediated Invasion of Collagen

Cell invasion was investigated by the Boyden Chamber Invasion Assay using the modified Boyden chamber. T. Frandsen et al., *Fibrinolysis*, 6: 71–76 (1992). Polycarbonate filters, 12 μm pore size, e.g., Millicell, Millipore Corporation, Bedford, Ma, were coated with 100 μg Type IV collagen (1 mg/ml 60% EtOH) and dried overnight at 25° C. Blind-well Boyden chambers are filled with 600 μl of serum-free media containing 0.1% BSA in the lower compartment, and the coated filters will be mounted in the chamber. Approximately 50,000 cells (tested to be greater than 95% viable) suspended in 400 μl of the same media will be placed in the upper chamber of the apparatus and allowed to settle onto the collagen-coated membrane. Varying concentrations of TSP-1 (0–150 nM) will be placed in the lower compartment and any neutralizing antibodies as well as peptides will be placed in the upper chamber. After an incubation period of about 3 to 6 hours at 37° C., the cells on the upper surface of the filter will be removed with a cotton swab. The filters are then fixed in 3% glutaraldehyde solution and stained with 0.5% crystal violet solution. Invasive cells adhering to the under-surface of the filter are counted using a phase contrast microscope (400×).

Figure 18:
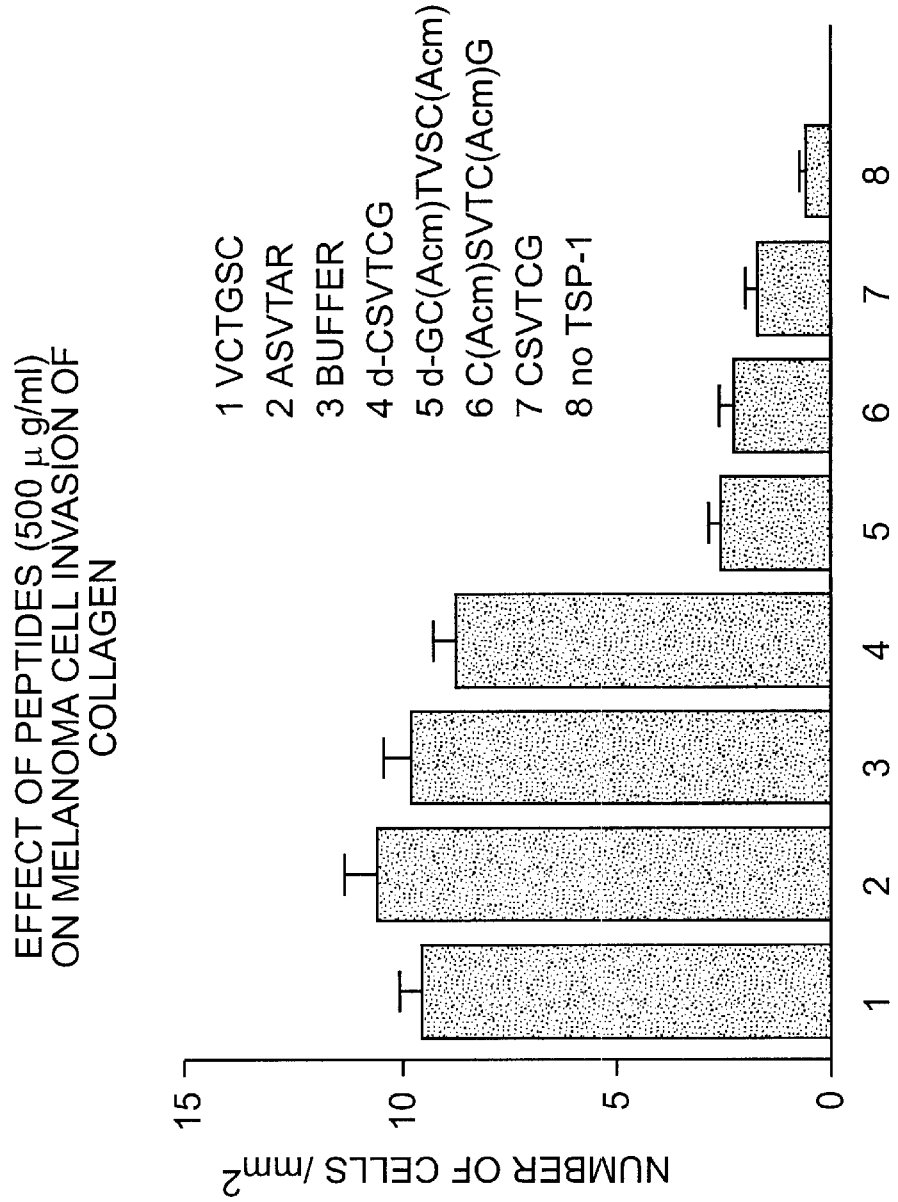
FIG. 18 depicts the effect of various TSP-1 derived peptides on TSP-1 mediated invasion of collagen.

Using this assay, mouse B16-F10 melanoma cells (50, 000) were plated on the collagen-coated disk of the Boyden chamber apparatus. The top chamber contained melanoma cells in the presence of 500 μg/ml of the TSP-1 derived peptide and the bottom chamber contained 20 μg/ml TSP-1. After 6 hours, cells traversing the collagen were counted as cells attached to the underside of the collagen-coated disk. Five representative fields per chamber in duplicate were counted. The data shown in FIG. 18 represents the average per field and the error bars represent the standard deviation. The scrambled peptide, Val-Cys-Thr-Gly-Ser-Cys (SEQ ID NO: 7), the irrelevant peptide, Ala-Ser-Val-Thr-Ala-Arg (SEQ ID NO: 38), buffer, and the d-amino acid Cys-Ser-Val-Thr-Cys-Gly (SEQ ID NO: 40) had no effect on invasion. In contrast, d-Gly-Cys-(Acm)-Thr-Val-Ser-Cys-(Acm) (SEQ ID NO: 35) (retroinverso), Cys-(Acm)-Ser-Val-Thr-Cys-(Acm)-Gly (SEQ ID NO: 6), and Cys-Ser-Val-Thr-Cys-Gly (SEQ ID NO: 1) peptides inhibited invasion by more than 90% and produced invasion comparable to that obtained in the absence of TSP-1 in the lower chamber (bar 8).

Example 30

Dose-dependent Effect of TSP-1 Peptides on Tumor Invasion

Figure 19:
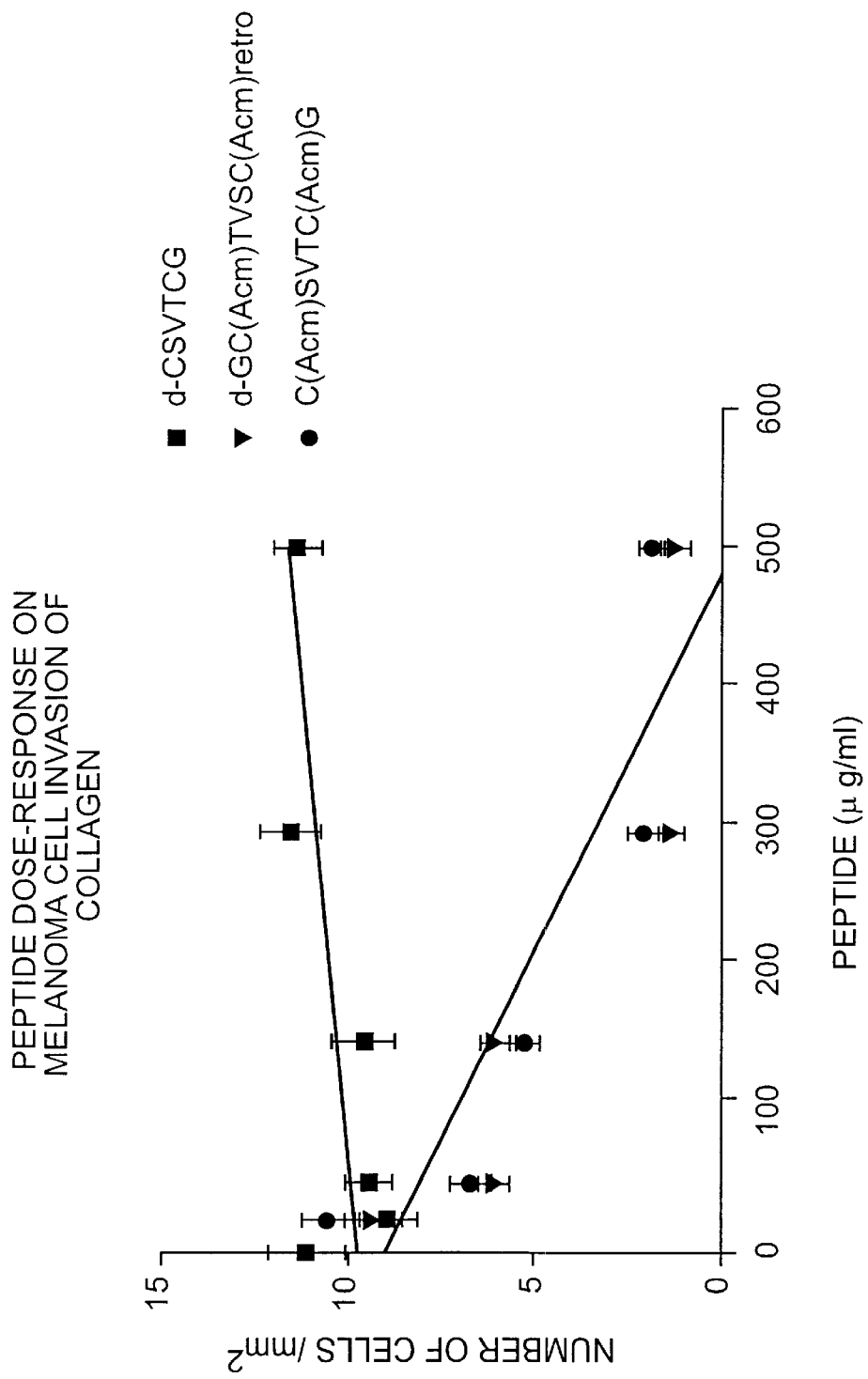
FIG. 19 depicts the dose-dependent effect of TSP-1 peptides on tumor invasion.

The experiments were performed as described for Example 29. The data presented in FIG. 19 shows that Cys-(Acm)-Ser-Val-Thr-Cys-(Acm)-Gly (SEQ ID NO: 6) and its retroinverso analogue produced the same dose-dependent inhibition of melanoma cell invasion. In contrast, d-Cys-Ser-Val-Thr-Cys-Gly (SEQ ID NO: 40) had no effect.

Example 31

Effect of TSP-1 Peptides on Direct Adhesion

Figure 20:
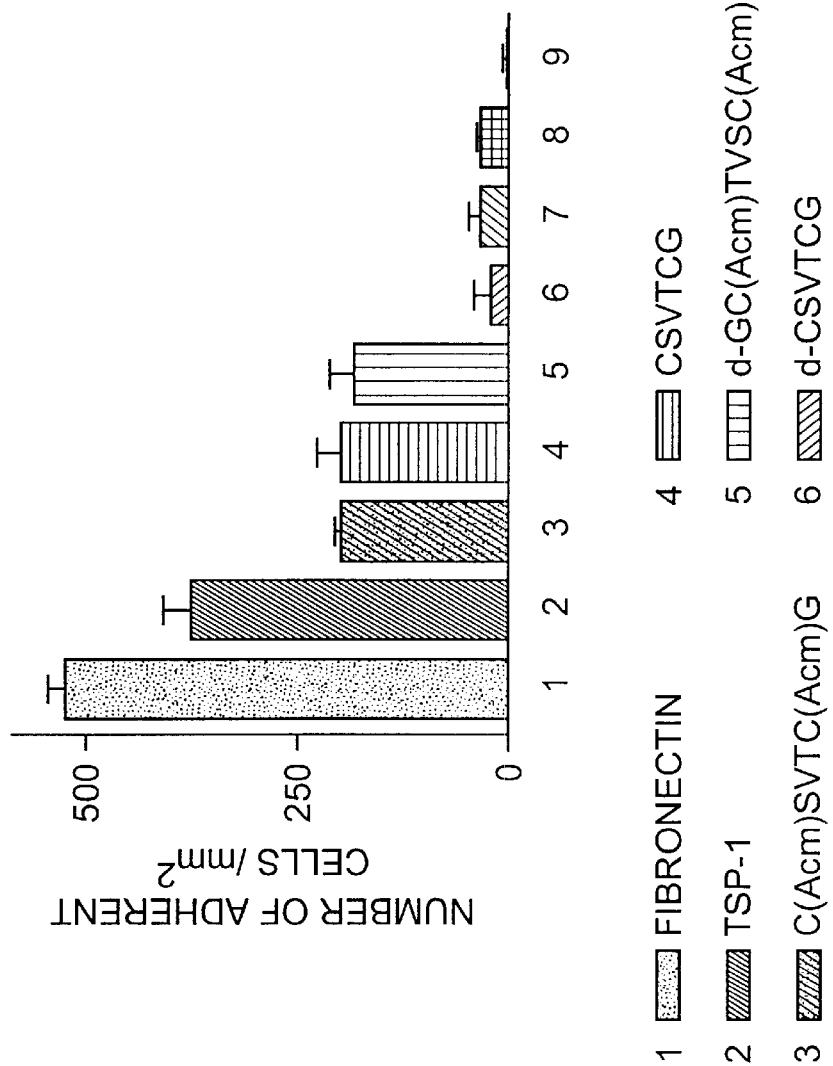
FIG. 20 depicts the effect of TSP-1 peptides on direct adhesion of B16-F10 melanoma cells.

Peptide effect on direct adhesion was tested by drying 10 μg of each peptide on the bottom of a 96well microtiter plate. Plates were blocked with BSA. Mouse B16-F10 melanoma cells (50,000) were plated in each well and allowed to attach for one hour. Non-adherent cells were aspirated out, plates rinsed, and adherent cells were fixed, stained, and counted. For each peptide the average of three wells is shown in FIG. 20. The error bars represent the standard deviation. The peptides, d-Gly-Cys-(Acm)-Thr-Val-Ser-Cys-(Acm) (retroinverso) (SEQ ID NO: 35), Cys-(Acm)-Ser-Val-Thr-Cys-(Acm)-Gly (SEQ ID NO: 6), and Cys-Ser-Val-Thr-Cys-Gly (SEQ ID NO: 1) promoted adhesion of cells half as well as fibronectin and TSP-1. In contrast, the scrambled peptide, Val-Cys-Thr-Gly-Ser-Cys (SEQ ID NO: 7), the irrelevant peptide, Ala-Ser-Val-Thr-Ala-Arg (SEQ ID NO: 39), and the d-amino acid Cys-Ser-Val-Thr-Cys-Gly (SEQ ID NO: 40 ) peptides, as well as BSA, did not promote adhesion.

Example 32

Effect of TSP-1 Peptides on Tumor Cell Metastasis

Figure 21:
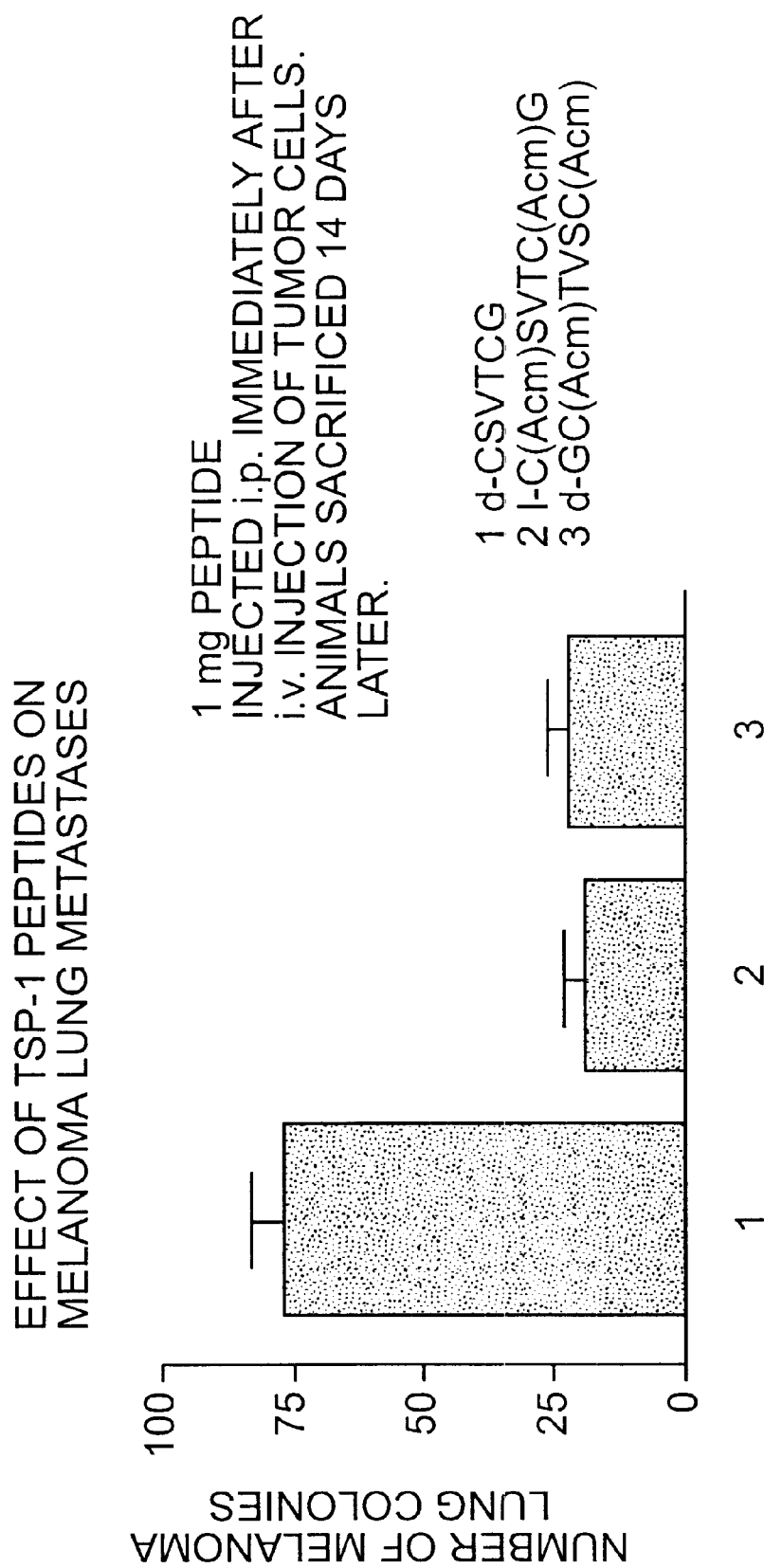
FIG. 21 depicts the effect of TSP-1 peptides on tumor cell metastasis.

Mouse B16-F10 melanoma cells (75,000) were injected intravenously and was immediately followed by one intraperitoneal injection of 1 mg of peptide. Six animals were treated with each peptide. Animals were sacrificed 14 days later and lung colonies counted. The data shown in FIG. 21 represents the mean of lung colonies and the error bars represent the standard error of the mean. The peptides, d-Gly-Cys-(Acm)-Thr-Val-Ser-Cys-(Acm) (retroinverso) (SEQ ID NO: 35), and l-Cys-(Acm)-Ser-Val-Thr-Cys-(Acm)-Gly (SEQ ID NO: 6) inhibited metastasis by more than 80%, whereas d-Cys-Ser-Val-Thr-Cys-Gly (SEQ ID NO: 40) had no effect.

We claim:

1. A polypeptide having the retroinverso form of a polypeptide of formula (I)

$$Z_1\text{-}Xaa_2\text{-}Xaa_3\text{-}Xaa_4\text{-}Xaa_5\text{-}Xaa_6\text{-}Xaa_7\text{-}Xaa_8\text{-}Xaa_9\text{-}Xaa_{10}\text{-}Z_2$$ (SEQ ID NO: 3)

wherein:

$Xaa_2$ is a neutral/non-polar/large/cyclic amino acid residue;

$Xaa_3$ is a neutral/polar/small or neutral/polar/large/non-cyclic or acidic amino acid residue;

$Xaa_4$ is a neutral/nonpolar/large/cyclic or neutral/nonpolar/large/non-cyclic or neutral/polar/large/non-cyclic or neutral/polar/small amino acid residue;

$Xaa_5$ is a neutral/polar/small amino acid residue $Xaa_6$ is a neutral/polar/small or neutral/polar/large/non-cyclic amino acid residue;

$Xaa_7$ is a neutral/nonpolar/large/non-cyclic or neutral/polar/large/non-cyclic amino acid residue;

$Xaa_8$ is a neutral/polar/large/non-cyclic or neutral/polar/small amino acid residue;

$Xaa_9$ is a neutral/polar/small amino acid residue;

$Xaa_{10}$ is a neutral/polar/small amino acid residue;

$Z_1$ is hydrogen, amino, acetyl or at least one amino acid residue or the desamino form thereof;

$Z_2$ is hydroxyl, carboxyl, non-amino acids such as agmatine, or at least one amino acid residue, including carboxyamide or alkylamide forms thereof; and wherein said polypeptide mimics or inhibits the biological activity of thrombospondin.

2. A polypeptide having the retroinverso form of a polypeptide of formula (II):

$$R_1\text{-}Cys\text{-}Xaa_{11}\text{-}Xaa_{12}\text{-}Xaa_{13}\text{-}Cys\text{-}R_2$$ (SEQ ID NO: 4)

wherein:

R₁ is a protected or unprotected terminal amino group, including hydrogen, amino, acetyl or at least one amino acid residue or the desamino form thereof;

Xaa₁₁, Xaa₁₂, and Xaa₁₃ are the same or different neutral/non-polar/large/non-cyclic or neutral/polar/large/non-cyclic or neutral/polar/small or basic/non-cyclic amino acid residues, preferably selected from the group consisting of valine, threonine, serine, and arginine;

R₂ is a protected or unprotected terminal carboxyl group including hydroxyl, carboxyl, or at least one amino acid residue, including carboxyamide or alkylamide forms thereof, preferably selected from the group consisting of lysine, glycine, and arginine;

wherein the structure of the polypeptide is optionally cyclized through a bond between the cysteines, such as a disulfide bond, or a bond between R₁ and R₂; and wherein said polypeptide mimics or inhibits the biological activity of thrombospondin.

3. The retroinverso polypeptide according to claim 2, wherein the cysteine residues are modified by a sulfhydral blocking group.

4. A retroinverso polypeptide having the formula d-Gly-Cys-Thr-Val-Ser-Cys (SEQ ID NO: 5), wherein the cysteine residues are modified with a sulfhydral blocking group.

5. The retroinverso polypeptide according to claim 4, wherein the sulfhydral blocking group is —CH₂—NH—COCH₃.

6. The retroinverso polypeptide according to any one of the claims 1, 2, 3, 4, or 5, wherein said polypeptide is linked to a chemotherapeutic drug.

7. The polypeptide according to claim 6, wherein the chemotherapeutic drug is selected from the group consisting of doxorubicin, chlorambucil, adriamycin, dauomycin, methotrexate, vindescine, alpha-amanitin, purothionin, bleomycin, and phenylenediamine mustard.

8. The polypeptide according to any one of the claims 1, 2, 3, 4, or 5, wherein the polypeptide is linked to an radioisotope.

9. The polypeptide according to any one of the claims 1, 2, 3, 4, or 5, wherein the polypeptide is linked to a cytotoxic agent.

10. The polypeptide according to claim 9, wherein the cytotoxic agent is selected from the group consisting of ricin, abrin, and diptheria toxin.

11. The polypeptide according to any one of the claims 1, 2, 3, 4, or 5, wherein the polypeptide is linked to a compound selected from the group consisting of human serum albumin, dextran, and covalently substituted poly-L-glutamic acid.

12. A method for inhibiting tumor cell metastasis comprising administering to a host in need of such inhibition an effective amount of a retroinverso polypeptide compound according to any one of the claims 1, 2, 3, 4, or 5.

13. A method for inhibiting tumor cell invasion comprising administering to a host in need of such inhibition an effective amount of a retroinverso polypeptide compound according to any one of the claims 1, 2, 3, 4, or 5.

14. A method for inhibiting tumor cell adhesion comprising administering to a host in need of such inhibition an effective amount of a retroinverso polypeptide according to any one of the claims 1, 2, 3, 4, or 5.

* * * * *

UNITED STATES PATENT AND TRADEMARK OFFICE
CERTIFICATE OF CORRECTION

PATENT NO.    : 6,339,062 B1                                         Page 1 of 1
DATED         : January 15, 2002
INVENTOR(S)   : Taffy Williams, George Tuszynski and Paul Actor It is certified that error appears in the above-identified patent and that said Letters Patent is hereby corrected as shown below:

Column 53,
Lines 29 and 30, "any one of the" should be deleted.
Line 30, "claims" should read -- claim --.

Column 54,
Lines 6, 9, 15, 22, 26 and 30 "any one of the" should be deleted.
Lines 6, 9, 15, 22, 26 and 30 "claims" should read -- claim --.

Signed and Sealed this

Twenty-first Day of January, 2003

JAMES E. ROGAN
*Director of the United States Patent and Trademark Office*

UNITED STATES PATENT AND TRADEMARK OFFICE
CERTIFICATE OF CORRECTION

PATENT NO. : 6,339,062 B1
DATED : January 15, 2002
INVENTOR(S) : Taffy Williams et al.

It is certified that error appears in the above-identified patent and that said Letters Patent is hereby corrected as shown below:

<u>Title page,</u>
Item [73], Assignee, please add -- MCP Hahnemann, Philadelphia, PA --

Signed and Sealed this

Nineteenth Day of July, 2005

JON W. DUDAS
*Director of the United States Patent and Trademark Office*

SEQUENCE LISTING

```
<160> NUMBER OF SEQ ID NOS: 38

<210> SEQ ID NO 1
<211> LENGTH: 6
<212> TYPE: PRT
<213> ORGANISM: Artificial Sequence
<220> FEATURE:
<223> OTHER INFORMATION: Description of Artificial Sequence: synthetic
      or human fragment/ analog of thrombospondin

<400> SEQUENCE: 1

Cys Ser Val Thr Cys Gly
 1               5

<210> SEQ ID NO 2
<211> LENGTH: 9
<212> TYPE: PRT
<213> ORGANISM: Artificial Sequence
<220> FEATURE:
<223> OTHER INFORMATION: Description of Artificial Sequence: synthetic
      fragment/ analog of thrombospondin

<400> SEQUENCE: 2

Trp Ser Pro Cys Ser Val Thr Cys Gly
 1               5

<210> SEQ ID NO 3
<211> LENGTH: 6
<212> TYPE: PRT
<213> ORGANISM: Artificial Sequence
<220> FEATURE:
<223> OTHER INFORMATION: Description of Artificial Sequence: synthetic
      fragment/ analog of thrombospondin
```

```
<400> SEQUENCE: 3

Gly Cys Thr Val Ser Cys
  1               5

<210> SEQ ID NO 4
<211> LENGTH: 6
<212> TYPE: PRT
<213> ORGANISM: Artificial Sequence
<220> FEATURE:
<223> OTHER INFORMATION: Description of Artificial Sequence: synthetic
      fragment/ analog of thrombospondin
<220> FEATURE:
<223> OTHER INFORMATION: Cys at positions 1 & 5 are blocked with (ACM)

<400> SEQUENCE: 4

Cys Ser Val Thr Cys Gly
  1               5

<210> SEQ ID NO 5
<211> LENGTH: 6
<212> TYPE: PRT
<213> ORGANISM: Artificial Sequence
<220> FEATURE:
<223> OTHER INFORMATION: Description of Artificial Sequence: synthetic
      fragment/ analog of thrombospondin

<400> SEQUENCE: 5

Val Cys Thr Gly Ser Cys
  1               5

<210> SEQ ID NO 6
<211> LENGTH: 4
<212> TYPE: PRT
<213> ORGANISM: Artificial Sequence
<220> FEATURE:
<223> OTHER INFORMATION: Description of Artificial Sequence: synthetic
      fragment/ analog of thrombospondin

<400> SEQUENCE: 6

Val Thr Cys Gly
  1

<210> SEQ ID NO 7
<211> LENGTH: 6
<212> TYPE: PRT
<213> ORGANISM: Artificial Sequence
<220> FEATURE:
<223> OTHER INFORMATION: Description of Artificial Sequence: synthetic
      fragment/ analog of thrombospondin

<400> SEQUENCE: 7

Cys Ser Thr Ser Cys Gly
  1               5

<210> SEQ ID NO 8
<211> LENGTH: 9
<212> TYPE: PRT
<213> ORGANISM: Artificial Sequence
<220> FEATURE:
<223> OTHER INFORMATION: Description of Artificial Sequence: synthetic
      fragment/ analog of thrombospondin

<400> SEQUENCE: 8

Trp Asp Ile Cys Ser Val Thr Cys Gly
  1               5

<210> SEQ ID NO 9
```

<210> SEQ ID NO 9
<211> LENGTH: 9
<212> TYPE: PRT
<213> ORGANISM: Artificial Sequence
<220> FEATURE:
<223> OTHER INFORMATION: Description of Artificial Sequence: synthetic fragment/ analog of thrombospondin

<400> SEQUENCE: 9

Trp Ser Ser Cys Ser Val Thr Cys Gly
 1               5

<210> SEQ ID NO 10
<211> LENGTH: 9
<212> TYPE: PRT
<213> ORGANISM: Artificial Sequence
<220> FEATURE:
<223> OTHER INFORMATION: Description of Artificial Sequence: synthetic fragment/ analog of thrombospondin

<400> SEQUENCE: 10

Trp Thr Ser Cys Ser Thr Ser Cys Gly
 1               5

<210> SEQ ID NO 11
<211> LENGTH: 23
<212> TYPE: PRT
<213> ORGANISM: Artificial Sequence
<220> FEATURE:
<223> OTHER INFORMATION: Description of Artificial Sequence: synthetic fragment/ analog of thrombospondin

<400> SEQUENCE: 11

Trp Ser Pro Trp Ser Glu Trp Thr Ser Cys Ser Thr Ser Cys Gly Asn
 1               5                  10                  15

Gly Ile Gln Gln Arg Gly Arg
            20

<210> SEQ ID NO 12
<211> LENGTH: 23
<212> TYPE: PRT
<213> ORGANISM: Artificial Sequence
<220> FEATURE:
<223> OTHER INFORMATION: Description of Artificial Sequence: synthetic fragment/ analog of thrombospondin

<400> SEQUENCE: 12

Trp Ser His Trp Ser Pro Trp Ser Ser Cys Ser Val Thr Cys Gly Asp
 1               5                  10                  15

Gly Val Ile Thr Arg Ile Arg
            20

<210> SEQ ID NO 13
<211> LENGTH: 23
<212> TYPE: PRT
<213> ORGANISM: Artificial Sequence
<220> FEATURE:
<223> OTHER INFORMATION: Description of Artificial Sequence: synthetic fragment/ analog of thrombospondin

<400> SEQUENCE: 13

Trp Gly Pro Trp Ser Pro Trp Asp Ile Cys Ser Val Thr Cys Gly Gly
 1               5                  10                  15

Gly Val Gln Lys Arg Ser Arg
            20

<210> SEQ ID NO 14

```
<211> LENGTH: 9
<212> TYPE: PRT
<213> ORGANISM: Artificial Sequence
<220> FEATURE:
<223> OTHER INFORMATION: Description of Artificial Sequence: synthetic
      fragment/ analog of thrombospondin

<400> SEQUENCE: 14

Trp Ser Pro Cys Ser Val Thr Cys Ser
 1               5

<210> SEQ ID NO 15
<211> LENGTH: 9
<212> TYPE: PRT
<213> ORGANISM: Artificial Sequence
<220> FEATURE:
<223> OTHER INFORMATION: Description of Artificial Sequence: synthetic
      fragment/ analog of thrombospondin

<400> SEQUENCE: 15

Trp Ser Gln Cys Ser Val Thr Cys Gly
 1               5

<210> SEQ ID NO 16
<211> LENGTH: 9
<212> TYPE: PRT
<213> ORGANISM: Artificial Sequence
<220> FEATURE:
<223> OTHER INFORMATION: Description of Artificial Sequence: synthetic
      fragment/ analog of thrombospondin

<400> SEQUENCE: 16

Trp Ser Gln Cys Asn Val Thr Cys Gly
 1               5

<210> SEQ ID NO 17
<211> LENGTH: 9
<212> TYPE: PRT
<213> ORGANISM: Artificial Sequence
<220> FEATURE:
<223> OTHER INFORMATION: Description of Artificial Sequence: synthetic
      fragment/ analog of thrombospondin

<400> SEQUENCE: 17

Trp Thr Pro Cys Ser Val Thr Cys Gly
 1               5

<210> SEQ ID NO 18
<211> LENGTH: 59
<212> TYPE: PRT
<213> ORGANISM: Artificial Sequence
<220> FEATURE:
<223> OTHER INFORMATION: Description of Artificial Sequence: synthetic
      fragment/ analog of thrombospondin

<400> SEQUENCE: 18

Asp Gly Gly Trp Ser His Trp Ser Pro Trp Ser Ser Val Thr Cys
 1               5                  10                  15

Gly Asp Gly Val Ile Thr Arg Ile Arg Leu Cys Asn Ser Pro Ser Pro
                20                  25                  30

Gln Met Asn Gly Lys Pro Cys Glu Gly Glu Ala Arg Glu Thr Lys Ala
                35                  40                  45

Cys Lys Lys Asp Ala Cys Pro Ile Asn Gly Gly
                50                  55

<210> SEQ ID NO 19
```

```
<211> LENGTH: 6
<212> TYPE: PRT
<213> ORGANISM: Artificial Sequence
<220> FEATURE:
<223> OTHER INFORMATION: Description of Artificial Sequence: synthetic
      fragment/ analog of thrombospondin
<220> FEATURE:
<223> OTHER INFORMATION: disulfide linked

<400> SEQUENCE: 19

Cys Ser Val Thr Cys Gly
 1               5

<210> SEQ ID NO 20
<211> LENGTH: 6
<212> TYPE: PRT
<213> ORGANISM: Artificial Sequence
<220> FEATURE:
<223> OTHER INFORMATION: Description of Artificial Sequence: synthetic
      fragment/ analog of thrombospondin
<220> FEATURE:
<223> OTHER INFORMATION: disulfide linked

<400> SEQUENCE: 20

Cys Ser Thr Ser Cys Gly
 1               5

<210> SEQ ID NO 21
<211> LENGTH: 6
<212> TYPE: PRT
<213> ORGANISM: Artificial Sequence
<220> FEATURE:
<223> OTHER INFORMATION: Description of Artificial Sequence: synthetic
      fragment/ analog of thrombospondin
<220> FEATURE:
<223> OTHER INFORMATION: blocked Cys residues

<400> SEQUENCE: 21

Cys Ser Thr Ser Cys Gly
 1               5

<210> SEQ ID NO 22
<211> LENGTH: 6
<212> TYPE: PRT
<213> ORGANISM: Artificial Sequence
<220> FEATURE:
<223> OTHER INFORMATION: Description of Artificial Sequence: synthetic
      fragment/ analog of thrombospondin

<400> SEQUENCE: 22

Cys Arg Val Thr Cys Gly
 1               5

<210> SEQ ID NO 23
<211> LENGTH: 6
<212> TYPE: PRT
<213> ORGANISM: Artificial Sequence
<220> FEATURE:
<223> OTHER INFORMATION: Description of Artificial Sequence: synthetic
      fragment/ analog of thrombospondin
<220> FEATURE:
<223> OTHER INFORMATION: disulfide linked

<400> SEQUENCE: 23

Cys Arg Val Thr Cys Gly
 1               5

<210> SEQ ID NO 24
<211> LENGTH: 7
```

```
<212> TYPE: PRT
<213> ORGANISM: Artificial Sequence
<220> FEATURE:
<223> OTHER INFORMATION: Description of Artificial Sequence: synthetic
      fragment/ analog of thrombospondin
<220> FEATURE:
<223> OTHER INFORMATION: disulfide linked

<400> SEQUENCE: 24

Arg Cys Arg Val Thr Cys Gly
 1               5

<210> SEQ ID NO 25
<211> LENGTH: 6
<212> TYPE: PRT
<213> ORGANISM: Artificial Sequence
<220> FEATURE:
<223> OTHER INFORMATION: Description of Artificial Sequence: synthetic
      fragment/ analog of thrombospondin

<400> SEQUENCE: 25

Cys Ser Val Thr Cys Lys
 1               5

<210> SEQ ID NO 26
<211> LENGTH: 6
<212> TYPE: PRT
<213> ORGANISM: Artificial Sequence
<220> FEATURE:
<223> OTHER INFORMATION: Description of Artificial Sequence: synthetic
      fragment/ analog of thrombospondin

<400> SEQUENCE: 26

Cys Ser Val Thr Cys Arg
 1               5

<210> SEQ ID NO 27
<211> LENGTH: 6
<212> TYPE: PRT
<213> ORGANISM: Artificial Sequence
<220> FEATURE:
<223> OTHER INFORMATION: Description of Artificial Sequence: synthetic
      fragment/ analog of thrombospondin

<400> SEQUENCE: 27

Cys Ser Arg Thr Cys Gly
 1               5

<210> SEQ ID NO 28
<211> LENGTH: 6
<212> TYPE: PRT
<213> ORGANISM: Artificial Sequence
<220> FEATURE:
<223> OTHER INFORMATION: Description of Artificial Sequence: synthetic
      fragment/ analog of thrombospondin
<220> FEATURE:
<223> OTHER INFORMATION: disulfide linked

<400> SEQUENCE: 28

Cys Arg Val Thr Cys Gly
 1               5

<210> SEQ ID NO 29
<211> LENGTH: 6
<212> TYPE: PRT
<213> ORGANISM: Artificial Sequence
<220> FEATURE:
<223> OTHER INFORMATION: Description of Artificial Sequence: synthetic
      fragment/ analog of thrombospondin
```

```
<400> SEQUENCE: 29

Cys Arg Thr Ser Cys Gly
 1               5

<210> SEQ ID NO 30
<211> LENGTH: 6
<212> TYPE: PRT
<213> ORGANISM: Artificial Sequence
<220> FEATURE:
<223> OTHER INFORMATION: Description of Artificial Sequence: synthetic
      fragment/ analog of thrombospondin

<400> SEQUENCE: 30

Cys Ser Thr Ser Cys Arg
 1               5

<210> SEQ ID NO 31
<211> LENGTH: 5
<212> TYPE: PRT
<213> ORGANISM: Artificial Sequence
<220> FEATURE:
<223> OTHER INFORMATION: Description of Artificial Sequence: synthetic
      fragment/ analog of thrombospondin

<400> SEQUENCE: 31

Cys Arg Val Thr Cys
 1               5

<210> SEQ ID NO 32
<211> LENGTH: 5
<212> TYPE: PRT
<213> ORGANISM: Artificial Sequence
<220> FEATURE:
<223> OTHER INFORMATION: Description of Artificial Sequence: synthetic
      fragment/ analog of thrombospondin

<400> SEQUENCE: 32

Cys Ser Thr Ser Cys
 1               5

<210> SEQ ID NO 33
<211> LENGTH: 6
<212> TYPE: PRT
<213> ORGANISM: Artificial Sequence
<220> FEATURE:
<223> OTHER INFORMATION: Description of Artificial Sequence: synthetic
      fragment/ analog of thrombospondin
<220> FEATURE:
<223> OTHER INFORMATION: Cys at positions 2 & 6 are blocked with (ACM)

<400> SEQUENCE: 33

Gly Cys Thr Val Ser Cys
 1               5

<210> SEQ ID NO 34
<211> LENGTH: 5
<212> TYPE: PRT
<213> ORGANISM: Artificial Sequence
<220> FEATURE:
<223> OTHER INFORMATION: Description of Artificial Sequence: synthetic
      fragment/ analog of thrombospondin

<400> SEQUENCE: 34

Gly Arg Gly Asp Ser
 1               5
```

```
<210> SEQ ID NO 35
<211> LENGTH: 7
<212> TYPE: PRT
<213> ORGANISM: Artificial Sequence
<220> FEATURE:
<223> OTHER INFORMATION: Description of Artificial Sequence: synthetic
      fragment/ analog of thrombospondin
<220> FEATURE:
<223> OTHER INFORMATION: Cys at positions 2 & 6 are blocked with (ACM)

<400> SEQUENCE: 35

Val Cys Thr Gly Ser Cys Gly
 1               5

<210> SEQ ID NO 36
<211> LENGTH: 5
<212> TYPE: PRT
<213> ORGANISM: Artificial Sequence
<220> FEATURE:
<223> OTHER INFORMATION: Description of Artificial Sequence: synthetic
      fragment/ analog of thrombospondin

<400> SEQUENCE: 36

Ala Ser Thr Ala Arg
 1               5

<210> SEQ ID NO 37
<211> LENGTH: 6
<212> TYPE: PRT
<213> ORGANISM: Artificial Sequence
<220> FEATURE:
<223> OTHER INFORMATION: Description of Artificial Sequence: synthetic
      fragment/ analog of thrombospondin

<400> SEQUENCE: 37

Ala Ser Val Thr Ala Arg
 1               5

<210> SEQ ID NO 38
<211> LENGTH: 6
<212> TYPE: PRT
<213> ORGANISM: Artificial Sequence
<220> FEATURE:
<223> OTHER INFORMATION: Description of Artificial Sequence: synthetic
      fragment/ analog of thrombospondin

<400> SEQUENCE: 38

Cys Ser Val Thr Cys Gly
 1               5
```